(12) United States Patent
Hammock et al.

(10) Patent No.: US 10,813,894 B2
(45) Date of Patent: Oct. 27, 2020

(54) METHODS OF INHIBITING PAIN

(71) Applicant: The Regents of the University of California, Oakland, CA (US)

(72) Inventors: Bruce D. Hammock, Davis, CA (US); Ahmet Bora Inceoglu, Davis, CA (US); Fawaz G. Haj, Davis, CA (US); Ahmed Bettaieb, Knoxville, TN (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/551,833

(22) PCT Filed: Feb. 11, 2016

(86) PCT No.: PCT/US2016/017613
§ 371 (c)(1),
(2) Date: Dec. 18, 2017

(87) PCT Pub. No.: WO2016/133788
PCT Pub. Date: Aug. 25, 2016

(65) Prior Publication Data
US 2018/0125803 A1 May 10, 2018

Related U.S. Application Data

(60) Provisional application No. 62/118,468, filed on Feb. 20, 2015.

(51) Int. Cl.
| | |
|---|---|
| *A61K 31/192* | (2006.01) |
| *A61P 25/02* | (2006.01) |
| *G01N 33/50* | (2006.01) |
| *A61K 31/4468* | (2006.01) |
| *A61K 45/06* | (2006.01) |

(52) U.S. Cl.
CPC ........ *A61K 31/192* (2013.01); *A61K 31/4468* (2013.01); *A61K 45/06* (2013.01); *A61P 25/02* (2018.01); *G01N 33/5008* (2013.01)

(58) Field of Classification Search
CPC .. A61K 31/192; A61K 31/4468; A61K 45/06; G01N 33/5008; A61P 25/02
See application file for complete search history.

(56) References Cited

U.S. PATENT DOCUMENTS

| | | |
|---|---|---|
| 4,310,525 A | 1/1982 | Nelson |
| 5,445,956 A | 8/1995 | Hammock et al. |
| 5,505,949 A | 4/1996 | Benitez |
| 5,955,496 A | 9/1999 | Hammock et al. |
| 5,962,455 A | 10/1999 | Blum et al. |
| 6,136,839 A | 10/2000 | Isakson et al. |
| 6,150,415 A | 11/2000 | Hammock et al. |
| 6,174,695 B1 | 1/2001 | Hammock et al. |
| 6,200,993 B1 | 3/2001 | Cote et al. |
| 6,531,506 B1 | 3/2003 | Kroetz et al. |
| 6,630,602 B1 | 10/2003 | Bialer et al. |
| 6,693,130 B2 | 2/2004 | Kroetz et al. |
| 6,756,210 B2 | 6/2004 | Hammock et al. |
| 6,831,082 B2 | 12/2004 | Ingraham et al. |
| 7,396,831 B2 | 7/2008 | Doherty et al. |
| 7,662,910 B2 | 2/2010 | Hammock et al. |
| 7,951,831 B2 | 5/2011 | Hammock et al. |
| 8,188,289 B2 | 5/2012 | Hammock et al. |
| 8,242,170 B2 | 8/2012 | Chiamvimonvat et al. |
| 8,263,651 B2 | 9/2012 | Hammock et al. |
| 8,399,425 B2 | 3/2013 | Hammock et al. |
| 8,455,652 B2 | 6/2013 | Hammock et al. |
| 8,476,043 B2 | 7/2013 | Hammock et al. |
| 8,501,783 B2 | 8/2013 | Hammock et al. |
| 8,513,302 B2 | 8/2013 | Hammock et al. |
| 8,815,951 B2 | 8/2014 | Hammock et al. |
| 9,029,401 B2 | 5/2015 | Hammock et al. |
| 9,029,550 B2 | 5/2015 | Hammock et al. |
| 9,034,903 B2 | 5/2015 | Hammock et al. |
| 9,096,532 B2 | 8/2015 | Hammock et al. |
| 9,119,837 B2 | 9/2015 | Hammock et al. |
| 2001/0016584 A1 | 8/2001 | Camborde et al. |
| 2002/0077355 A1 | 6/2002 | Liao et al. |
| 2003/0077342 A1 | 4/2003 | Maffetone |
| 2003/0113824 A1 | 6/2003 | Hammock et al. |
| 2003/0119900 A1 | 6/2003 | Kroetz et al. |

(Continued)

FOREIGN PATENT DOCUMENTS

| | | |
|---|---|---|
| CA | 2619768 A1 | 2/2007 |
| EP | 1 129 706 A2 | 9/2001 |

(Continued)

OTHER PUBLICATIONS

Sergey Lupachyk, Pierre Watcho, Roman Stavniichuk, Hanna Shevalye, and Irina G. Obrosova, Endoplasmic Reticulum Stress Plays a Key Role in the Pathogenesis of Diabetic Peripheral Neuropathy, Diabetes, vol. 62, Mar. 2013, 944-951 (Year: 2013).*

Analgesic Combinations webpage (Year: 2019).*

US Decision on Appeal Before the Board of Patent Appeals and Interferences [Affirmed] dated Jun. 22, 2010 issued in U.S. Appl. No. 10/694,641.

European Search Report for PCT/US2007/000373 dated Dec. 2, 2010.

Ahlgren, et al. (1993) "Mechanical Hyperalgesia in Streptozotocin-Diabetic Rats," Neuroscience, vol. 52, No. 4, pp. 1049-1055.

Aley, et al. "Rapid Onset Pain Induced by Intravenous Streptozotocin in the Rat," The Journal of Pain, vol. 2, No. 3, Jun. 2001, pp. 146-150.

(Continued)

*Primary Examiner* — Sarah Pihonak
*Assistant Examiner* — Jason Deck
(74) *Attorney, Agent, or Firm* — Mintz, Levin, Cohn, Ferris, Glovsky & Popeo, P.C.

(57) ABSTRACT

Provided are methods and compositions for preventing, reducing, mitigating and treating pain, particularly neuropathic pain by the combined administration of an agent that increases EETs and an agent that reduces/inhibits endoplasmic reticulum (ER) stress.

11 Claims, 18 Drawing Sheets
Specification includes a Sequence Listing.

(56) References Cited

U.S. PATENT DOCUMENTS

| | | |
|---|---|---|
| 2003/0139469 A1 | 7/2003 | Weiss et al. |
| 2003/0207845 A1 | 11/2003 | Keating et al. |
| 2004/0038917 A1 | 2/2004 | Orntoft et al. |
| 2004/0092487 A1 | 5/2004 | Kroetz et al. |
| 2004/0092567 A1 | 5/2004 | Ingraham et al. |
| 2004/0242595 A1 | 12/2004 | Eggenweiler et al. |
| 2005/0026844 A1 | 2/2005 | Hammock et al. |
| 2005/0107405 A1 | 5/2005 | Takasaka |
| 2005/0164951 A1 | 7/2005 | Hammock et al. |
| 2005/0222252 A1 | 10/2005 | Hammock et al. |
| 2005/0261255 A1 | 11/2005 | Serhan et al. |
| 2005/0282767 A1 | 12/2005 | Kroetz et al. |
| 2006/0035869 A1 | 2/2006 | Hammock et al. |
| 2006/0099269 A1 | 5/2006 | Cheatham et al. |
| 2006/0148744 A1 | 7/2006 | Hammock et al. |
| 2006/0178347 A1 | 8/2006 | Hammock et al. |
| 2006/0270609 A1 | 11/2006 | Hammock et al. |
| 2007/0117782 A1 | 5/2007 | Hammock et al. |
| 2007/0225283 A1 | 9/2007 | Hammock et al. |
| 2008/0188554 A1 | 8/2008 | Hammock et al. |
| 2008/0249055 A1 | 10/2008 | Hammock et al. |
| 2008/0279912 A1 | 11/2008 | Hammock et al. |
| 2009/0018092 A1 | 1/2009 | Hammock et al. |
| 2009/0042951 A1 | 2/2009 | Danziger |
| 2009/0215894 A1 | 8/2009 | Hammock et al. |
| 2009/0216318 A1 | 8/2009 | Chiamvimonvat et al. |
| 2009/0326039 A1 | 12/2009 | Hammock et al. |
| 2010/0074852 A1 | 3/2010 | Hammock et al. |
| 2010/0267807 A1 | 10/2010 | Hammock et al. |
| 2010/0286222 A1 | 11/2010 | Hammock et al. |
| 2010/0317733 A1 | 12/2010 | Hammock et al. |
| 2011/0021448 A1 | 1/2011 | Hammock et al. |
| 2011/0065756 A1 | 3/2011 | De Taeye et al. |
| 2011/0098322 A1 | 4/2011 | Sanborn et al. |
| 2011/0230504 A1 | 9/2011 | Hammock et al. |
| 2011/0245331 A1 | 10/2011 | Kroetz et al. |
| 2011/0269831 A1 | 11/2011 | Hammock et al. |
| 2012/0046251 A1 | 2/2012 | Schaefer et al. |
| 2013/0045172 A1 | 2/2013 | Hammock et al. |
| 2013/0065936 A1 | 3/2013 | Hammock et al. |
| 2013/0137726 A1 | 5/2013 | Hammock et al. |
| 2013/0143925 A1 | 6/2013 | Hammock et al. |
| 2013/0274476 A1 | 10/2013 | Hammock et al. |
| 2014/0038923 A1 | 2/2014 | Hammock et al. |
| 2014/0088156 A1 | 3/2014 | Hammock et al. |
| 2015/0011586 A1 | 1/2015 | Hammock et al. |
| 2015/0017267 A1 | 1/2015 | Guedes et al. |
| 2015/0065540 A1 | 3/2015 | Hammock et al. |
| 2016/0008342 A1 | 1/2016 | Chiamvimonvat et al. |

FOREIGN PATENT DOCUMENTS

| | | | |
|---|---|---|---|
| EP | 1845976 A2 | 10/2007 | |
| EP | 1931201 B1 | 5/2012 | |
| JP | 5059032 A | 3/1993 | |
| JP | 2009-504785 | 2/2009 | |
| WO | WO 1996/41626 | 12/1996 | |
| WO | WO 99/54282 A1 | 10/1999 | |
| WO | WO 00/23060 A2 | 4/2000 | |
| WO | WO 2001/10438 A1 | 2/2001 | |
| WO | WO 2002/089787 A1 | 11/2002 | |
| WO | WO 2004/089296 A2 | 10/2004 | |
| WO | WO 2005/089380 A2 | 9/2005 | |
| WO | WO 2006/086108 A2 | 8/2006 | |
| WO | WO 2006/133257 A2 | 12/2006 | |
| WO | WO 2007/022509 A2 | 2/2007 | |
| WO | WO 2007/106525 A1 | 9/2007 | |
| WO | WO 2008/016884 A2 | 2/2008 | |
| WO | WO 2008/073130 A1 | 6/2008 | |
| WO | WO 2009/062073 A1 | 5/2009 | |
| WO | WO 2010/030851 A1 | 3/2010 | |
| WO | WO 2011/143607 A1 | 11/2011 | |
| WO | WO-2013116713 A1 * | 8/2013 | ......... A61K 31/4468 |
| WO | WO-2013138118 A1 * | 9/2013 | |

OTHER PUBLICATIONS

Arner, et al. "Lack of analgesic effect of opioids on neuropathic and idiopathic forms of pain," Pain,vol. 33, No. 1, Apr. 1988, pp. 11-23.

Attal, N. et al., "EFNS guidelines on the pharmacological treatment of neuropathic pain: 2010 revision," EurJ Neural. Sep. 2010;17(9):1113-e88, PubMed abstract No. 20402746.

Attal, N. et al., "Pharmacotherapy of neuropathic pain: which drugs, which treatment algorithms?" Pain. Apr. 2015;156 Suppl1:S104-14, PubMed abstract No. 25789426.

Baron, R. (2009) "Neuropathic Pain: A Clinical Perspective," In: Canning B., Spina D. (eds) Sensory Nerves, Handbook of Experimental Pharmacology, vol. 194, Springer, Berlin, Heidelberg, pp. 3-30.

Basbaum, Allan I. et al., (Oct. 16, 2009) "Cellular and Molecular Mechanisms of Pain," *Cell*, 139:267-284.

Basbaum, et al. (1999) "Pain," Current Biology, vol. 9, No. 12, pp. R429-R431.

Bettaieb et al. (2013) "Soluble epoxide hydrolase deficiency or inhibition attenuates diet-induced endoplasmic reticulum stress in liver and adipose tissue," *J Biol Chem*, 288:14189-14199.

Boada et al. (2015) "Nerve injury induces a new profile of tactile and mechanical nociceptor input from undamaged peripheral afferents," *J Neurophysiol*, 113:100-109 [First published Oct. 1, 2014; doi:10.1152/jn 00506 02014].

Boulton, A. (2005) "Management of Diabetic Peripheral Neuropathy," Clinical Diabetes,vol. 23, pp. 9-15.

Capdevila et al. (Aug. 31, 1981) "The oxidative metabolism of arachidonic acid by purified cytochromes P-450," *Biochem Biophys Res Comm*, 101(4):1357-1363.

Chacos et al. (1983) "The reaction of arachidonic acid epoxides (epoxyeicosatrienoic acids) with a cytosolic epoxide hydrolase," *Arch Biochem Biophys*, 223(2):639-648.

Chang, I. J. et al. (Dec. 27, 2004) "Are all COX-2 inhibitors created equal?" *Hyperension*, 45(2):178-180.

Chen, et al. (2002) Hypersensitivity of Spinothalamic Tract Neurons Associated With Diabetic Neuropathic Pain in Rats, J Neurophysiol., 87, pp. 2726-2733.

Chiamvimonvat, N., et al., "The Soluble Epoxide Hydrolase as a Pharmaceutical Target for Hypertension," Cardiovasc Pharmacol, vol. 50, No. 3, Sep. 2007, pp. 225-237.

Chiang, et al., "Aspirin triggers anti-inflammatory 15-epi-lipoxin $A_4$, and inhibits thromboxane in a randomized human trial," Proc. Natl. Acad. Sci.,vol. 101, No. 42, Oct. 19, 2004, pp. 15178-15183.

Chou, (2006) "Theoretical basis, experimental design, and computerized simulation of synergism and antagonism in drug combination studies," *Pharmacol Rev*, 58(3):621-681.

Courteix et al. (1994) Research Reports: "Study of the sensitivity of the diabetes-induced pain model in rats to a range of analgesics," *Pain*, 57:153-160.

Crain et al. (2008) "Low doses of cyclic AMP-phosphodiesterase inhibitors rapidly evoke opioid receptor-mediated thermal hyperalgesia in naive mice which is converted to prominent analgesia by cotreatment with ultra-low-dose naltrexone" *Brain Research* 1231: 16-24.

Cunha et al. (1999) "Pharmacological modulation of secondary mediator systems—cyclic AMP and cyclic GMP—on inflammatory hyperalgesia" *British Journal of Pharmacology* 127:671-678.

Cunningham, et al. [Abstract Only] "Valproate modifies spontaneous excitation and inhibition at cortical synapses in vitro," Neuropharmacology, vol. 45, No. 7, Dec. 2003, pp. 907-917.

Da Cunha et al. (2004) "Endothelins induce $ET_B$ receptor-mediated mechanical hypernociception in rat hindpaw: roles of cAMP and protein kinase C," *European Journal of Pharmacology*, 501:87-94.

Datta, K. et al. (1999) The 5-lipoxygenase-activating protein (FLAP) inhibitor, MK886, induces apoptosis independently of FLAP, *Biochem J*, 340(Pt 2):371-375.

De Taeye et al. (Mar. 2010) "Expression and regulation of soluble epoxide hydrolase in adipose tissue," *Obesity*, 18(3):489-498.

De Visser et al. (2008) "Phosphodiesterase-4 inhibition attenuates pulmonary inflammation in neonatal lung injury," European Respiratory Journal, vol. 31, No. 3, pp. 633-644.

(56) References Cited

OTHER PUBLICATIONS

Dewachter et al. (2010) [Abstract Only] "New therapies for pulmonary arterial hypertension: an update on current bench to bedside translation," Expert Opin Investig Drugs, 19(4):469-88 (1 page).
Dewey et al. (2013) "Proteomic analysis of hearts from Akita mice suggests that increases in soluble epoxide hydrolase and antioxidative programming are key changes in early stages of diabetic cardiomyopathy," *J Proteome Res*, 12:3920-3933.
Djouhri et al. (2012) "Partial nerve injury induces electrophysiological changes in conducting (uninjured) nociceptive and nonnociceptive DRG neurons: Possible relationships to aspects of peripheral neuropathic pain and paresthesias," *Pain*, 153:1824-1836.
Doyle et al. (2011) "Unfolded proteins and endoplasmic reticulum stress in neurodegenerative disorders," *J Cell Mol Med*, 15(10):2025-2039.
Dworkin, Robert H. et al. (2007) "Pharmacologic management of neuropathic pain: Evidence-based recommendations," *Pain*, 132:237-251.
Eickholt, et al. "Effects of Valproic Acid Derivatives on Inositol Trisphosphate Depletion, Teratogenicity, Glycogen Synthase Kinase-3β Inhibition, and Viral Replication: A Screening Approach for New Bipolar Disorder Drugs Derived from the Valproic Acid Core Structure," Molecular Pharmacology, vol. 67, No. 5, May 2005, pp. 1426-1433.
Enna et al. (2006) [Abstract Only] "The role of GABA in the mediation and perception of pain," Adv Pharmacol, 54:1-27 (3pp).
Enoch, et al. "Problem Drinking and Alcoholism: Diagnosis and Treatment," American Family Physician, vol. 65, No. 3, Feb. 1, 2002, pp. 441-448 and 449-450.
Fang, X. (2006) "Soluble Epoxide Hydrolase: A Novel Target for the Treatment of Hypertension," Recent Patents on Cardiovascular Drug Discovery, vol. 1, No. 1, pp. 67-72.
Finley, et al. (1988) "Increased cholesterol epoxide hydrolase activity in clofibrate-fed animals," Biochemical Pharmacology, vol. 37, No. 16, pp. 3169-3175.
Finnerup, N.B. et al., "Pharmacotherapy for neuropathic pain in adults: a systematic review and meta-analysis," Lancet Neural. Feb. 2015;14(2): 162-73.
Finnerup, N.B. et al., "Pharmacotherapy for neuropathic pain in adults: systematic review, meta-analysis and updated NeuPSIG recommendations," Lancet Neural. Feb. 2015; 14(2): 162-173.
Fiset et al. (2003) "Human Neutrophils as a Source of Nociceptin: A Novel Link between Pain and Inflammation," *Biochemistry*, 42(35):10498-10505.
Fisher et al. (2003) "Sodium valproate or valproate semi sodium: is there a difference in the treatment of bipolar disorder?" Psychiatric Bulletin, vol. 27, pp. 446-448.
Fitzgerald, G.A., "COX-2 in play at the AHA and the FDA," Trends in Pharmacological Sciences, vol. 28, No. 7, Jul. 2007, pp. 303-307. <URL: https://doi.org/10.1016/j.tips.2007.05.007>.
Gately, S., et al., [Abstract-Only]"Therapeutic potential of selective cyclooxygenase-2 inhibitors in the management of tumor angiogenesis," Prog. Exp. Tumor Res. (2003), vol. 37, pp. 179-192.
Gilron, I. et al., "Neuropathic pain: principles of diagnosis and treatment," Mayo Clin. Prac., Apr. 2015, vol. 90, No. 4, pp. 532-545.
Gilroy, et al. (2001) "COX-2 expression and cell cycle progression in human fibroblasts," Am. J. Physiol. Cell Physiol., vol. 281, pp. C188-C194.
Gilroy, et al. (Feb. 2001) "Cell cycle-dependent expression of cyclooxygenase-2 in human fibroblasts," The FASEB Journal, vol. 15, pp. 288-290.
Goodman & Gilman's (2001) "The Pharmacological Basis of Therapeutics," 2001, *Tenth Edition*, Table 27-3, p. 710.
Gregor et al. (Mar. 2009) "Endoplasmic reticulum stress is reduced in tissues of obese subjects after weight loss," *Diabetes*, 58:693-700.
Griswold et al. (1993) "Effect of Selective Phosphodiesterase Type IV Inhibitor, Rolipram, on Fluid and Cellular Phases of Inflammatory Response," *Inflammation*, 17(3):333-344.
Guedes et al. (2013) "Use of a soluble epoxide hydrolase inhibitor as an adjunctive analgesic in a horse with laminitis," *Vet Anaesth Analg*, 40:440-448.
Hawkey, C.J. et al., [Abstract-Only] "Cyclooxygenase-2 inhibitors," Curr. Opin. Gastroenterology., Nov. 2005, vol. 21, No. 6, pp. 660-664.
Hetz et al. (Sep. 2013) "Targeting the unfolded protein response in disease," *Nat Rev Drug Disc*, 12:703-719.
Imig, John D., (2006) "Cardiovascular Therapeutic Aspects of Soluble Epoxide Hydrolase Inhibitors," Cardiovascular Drug Review, vol. 24, No. 2, pp. 169-188.
Inceoglu et al. (2006) "Inhibition of soluble epoxide hydrolase reduces LPS-induced thermal hyperalgesia and mechanical allodynia in a rat model of inflammatory pain," *Science Direct, Life Sci*, 79:2311-2319.
Inceoglu et al. (2011) "Analgesia mediated by soluble epoxide hydrolase inhibitors is dependent on cAMP," *P Natl Acad Sci USA*, 108(12):5093-5097.
Inceoglu et al. (Jan. 2007) "Soluble epoxide hydrolase inhibition reveals novel biological functions of epoxyeicosatrienoic acids (EETs)," *NIH, Prostaglandins Other Lipid Mediat.* 82(1-4):42-49.
Inceoglu, et al. (2008) "Soluble epoxide hydrolase and epoxyeicosatrienoic acids modulate two distinct analgesic pathways," Proceedings of the National Academy Sciences, vol. 105, No. 48, pp. 18901-18906.
Inceoglu, et al. (2012) "Acute augmentation of epoxygenated fatty acid levels rapidly reduces pain-related behavior in a rat model of type I diabetes," *Proc Natl Acad Sci USA*, 109:11390-11395.
Inceoglu, et al. (2013) "Epoxy fatty acids and inhibition of the soluble epoxide hydrolase selectively modulate GABA mediated neurotransmission to delay onset of seizures," *PLoS One*, 8(12):e80922, 10pp.
Jackson II, K. "Pharmacotherapy for Neuropathic Pain," World Institute of Pain, Pain Practice, vol. 6, No. 1 (2006), pp. 27-33.
Jain et al. (2001) "Sildenafil-induced peripheral analgesia and activation of the nitric oxide—cyclic GMP pathway," *Brain Research*, 909:170-178.
Ji et al. (2009) "MAP kinase and pain," *Brain Res Rev*, 60(1):135-148.
Johannessen, et al. [Abstract Only] "Mechanisms of action of valproate: a commentary," Neurochemistry International, vol. 37, No. 2-3, Aug. 1, 2000, pp. 103-110.
Jones, R.A., "Etodolac: An overview of a selective COX-2 inhibitor," Inflammopharmacology, vol. 7, No. 3, Aug. 1999, pp. 269-275. <ISSN:0925-4692; XP008158641>.
Julius, David et al. (Sep. 13, 2001) "Molecular mechanisms of nociception," *Nature*, 413:203-210.
Jung, et al. "Soluble Epoxide Hydrolase Is a Main Effector of Angiotensin II-Induced Hypertension," Hypertension, Feb. 7, 2005, vol. 45, part 2, pp. 759-765).
Karara, A. et al. (1989) "Endogenous Epoxyeicosatrienoic Acids," The Journal of Biological Chemistry, vol. 264, No. 33, pp. 19822-19827.
Kardosh et al. (2005) "Dimethyl-celecoxib (DMC), a derivative of celecoxib that lacks cyclooxygenase-2-inhibitory function, potently mimics the anti-tumor effects of celecoxib on Burkitt's lymphoma in vitro and in vivo," *Cancer Biol Ther*, 4:571-582.
Kathuria, S. et al., "Modulation of anxiety through blockade of anandamide hydrolysis," Nature Medicine, vol. 9, No. 1, Jan. 2003, pp. 76-81.
Kim, I.H. et al. (2004) "Design, Synthesis, and Biological Activity of 1, 3-disubstituted Ureas as Potent Inhibitors of the Soluble Epoxide Hydrolase of Increased Water Solubility," *J Med Chem*, 2004, 47(8):2110-2122.
Kim, I.H. et al. (2005) "Optimization of Amide-Based Inhibitors of Soluble Epoxide Hydrolase with Improved Water Solubility," J. Med. Chem., May 19, 2005, vol. 48, No. 10, pp. 3621-3629.
Kloke, et al. (1991) "Anti-Depressants and Anti-Convulsants for the Treatment of Neuropathic Pain Syndromes in Cancer Patients," *Onkologie*, 14(1):40-43.

(56) References Cited

OTHER PUBLICATIONS

Kochuvelikakam et al. (Mar. 15, 1999) "Role of Protein Kinase A in the Maintenance of Inflammatory Pain," *The Journal of Neuroscience*, 9(6):2181-2186.

Konstam, M.D., et al., [First-Page Only] "Cardiovascular events and COX-2 inhibitors," JAMA, vol. 286, No. 22, Dec. 12, 2001, pp. 1-2.

Kozutsumi et al. (1988) "The presence of malfolded proteins in the endoplasmic reticulum signals the induction of glucose-regulated proteins," *Nature*, 332:462-464.

Kumar et al. (2000) "Analgesic and anti-inflammatory effects of phosphodiesterase inhibitors." *Indian J Exp Biol.* 38(1):26-30 [Abstract Only], 1 page.

Laufer, S., "Osteoarthritis therapy—are there still unmet needs?" Rheumatology, vol. 43 (Suppl. 1), Feb. 2004, pp. i9-i15. <doi:10.1093/rheumatology/kch103>.

Ledeboer, et al. (2007) "Ibudilast (AV-411): a new class therapeutic candidate for neuropathic pain and opioid withdrawal syndromes," Expert Opinion on Investigational Drugs, 16:7, pp. 935-950. <doi:10.1517/13543784.16.7.935>.

Lindsay, Tammy J. et al., "Treating diabetic peripheral neuropathic pain," American Family Physician, vol. 82, No. 2, Jul. 15, 2010.

Liu, et al. (2010) "Inhibition of soluble epoxide hydrolase enhances the anti-inflammatory effects of aspirin and 5-lipoxygenase activation protein inhibitor in a murine model," Biochemical Pharmacology, vol. 79, pp. 880-887.

Loscher, W. [Abstract Only] "Basic Pharmacology of Valproate," CNS Drugs, vol. 16, No. 10, Oct. 2002, pp. 669-694.

Lupachyk et al. (2013) "Endoplasmic reticulum stress contributes to prediabetic peripheral neuropathy," *Exp Neurol*, 247:342-348 [Article in Press].

Maisano et al. (2007) "Analgesia before, during and after surgery: prevention of postoperative pain," *Minerva Anestesiol*, 73(12):613-614.

Malik, R.A. (2014) [Abstract Only] "The Pathology of human diabetic neuropathy," Handb Clin Neurol, 126:249-259.

Maroon et al. (2010) "Natural anti-inflammatory agents for pain relief," Surgical Neurology International, 2010, 1:80, pp. 1-20.

Meade, et al. "Peroxisome Proliferators Enhance Cyclooxygenase-2 Expression in Epithelial Cells*" The Journal of Biological Chemistry, vol. 274, No. 12, Mar. 19, 1999, pp. 8328-8334.

Melinkova, Irena, (Aug. 2010) "Pain Market," *Nature Reviews*, 9:589-590.

Merkel, et al. (A695, Abstract, Proc of the 2010 Annual Meeting of the Am. Soc. Anesthesiologists, 'Sex Differences in Cardioprotection in the sEH/EET signaling Pathway, p. 1).

Morisseau et al. (2010) "Naturally occurring monoepoxides of eicosapentaenoic acid and docosahexaenoic acid are bioactive antihyperalgesic lipids," *J Lipid Res*, 51:3481-3490.

Morisseau et al., "Potent urea and carbamate inhibitors of soluble epoxide hydrolases," Proc. Natl. Acad. Sci., Agricultural Sciences, vol. 96, Aug. 1999, pp. 8849-8854.

Morisseau, C. et al. (2002) "Structural refinement of inhibitors ofurea-based soluble epoxide hydrolases," *Biochem Pharmacal*,63(9):1599-1608.

Nickel, F. et al. "Mechanisms of Neuropathic Pain," European Neauropsychopharmacology, vol. 22 (2012), pp. 81-91.

Node, K., et al., "Anti-inflammatory Properties of Cytochrome P450 Epoxygenase-Derived Eicosanoids," Science, vol. 285, No. 5431, Aug. 20, 1999, pp. 1276-1279.

Omoigui, Sota, (2007) "The biochemical origin of pain—Proposing a new law of pain: The origin of all pain is inflammation and the inflammatory response. Part 1 of 3—A unifying law of pain," *Medical Hypotheses*, 69:70-82.

Omoigui, Sota, (2007) "The biochemical origin of pain—Proposing a new law of pain: The origin of all pain is inflammation and the inflammatory response. Part 2 of 3—Inflammatory Profile of Pain Syndromes," *Medical Hypotheses*, 69(6):1169-1178, 13pp.

Ouseph et al. (1995) "Multiple Second Messenger Systems Act Sequentially to Mediate Rolipram-Induced Prolongation of Prostaglandin E2-Induced Mechanical Hyperalgesia in the Rat," *Neuroscience* 64(3):769-776.

Özcan et al. (2004) "Endoplasmic reticulum stress links obesity, insulin action, and type 2 diabetes," *Science*, 306:457-461.

Özcan et al. (2006) "Chemical chaperones reduce ER stress and restore glucose homeostasis in a mouse model of type 2 diabetes," *Science*, 313:1137-1140.

Pacifici, et al. (1989) "Valpromide is a poor inhibitor of the cytosolic epoxide hydrolase," Arch. Toxicol., vol. 63, pp. 157-159.

Park, J.Y., et al., "Prostaglandin E2 synthesis and secretion: The role of PGE2 synthases," Clinical Immunology, vol. 119, No. 3, Jun. 2006, pp. 229-240. <URL:https://doi.org/10.1016/j.clim.2006.01.016>.

Peek, R.M. jr., [Abstract-Only] "Prevention of colorectal cancer through the use of COX-2 selective inhibitors," Cancer Chemother. Pharmacol. (2004) vol. 54, Suppl. 1, pp. S50-S56.

Peltier et al. (2014) "Painful diabetic neuropathy," *Bmj*, 348:g1799 [Abstract Only], 2pp.

Penning, et al. "Purification and Properties of 3α-Hydroxysteroid Dehydrogenase from Rat Brain Cytosol," The Journal of Biological Chemistry, vol. 260, No. 28, Dec. 5, 1985, pp. 15266-15272.

Perucca, E., [Abstract Only] "Pharmacological and Therapeutic Properties of Valproate," CNS Drugs, vol. 16, No. 10, Oct. 2002, pp. 695-714.

Piomelli et al. (Nov. 12, 2014) "A lipid gate for the peripheral control of pain," *J Neurosci*, 34(46):15184-15191.

Pratico, D. et al. [Abstract-Only] "Selective cyclooxygenase-2 inhibitors development in Cardiovascular medicine," Circulation, vol. 112, No. 7, Aug. 16, 2005, pp. 1073-1079.

Presley et al., (1992) "Novel Approaches to the Treatment of Neuropathic Pain," *West J Med*, 157(5):564.

Pyrko et al. (2007) "Calcium-activated endoplasmic reticulum stress as a major component of tumor cell death induced by 2,5-dimethyl-celecoxib, a non-coxib analogue of celecoxib," *Mol Cancer Thera*, 6:1262-1275.

Quintao, N., et al. "The Effects of Diacerhein on Mechanical Allodynia in Inflammatory and Neuropathic Models of Nociception in Mice," Anesthesia & Analgesia, Dec. 2005, vol. 101, No. 6, pp. 1763-1769.

Rathmel et al. (2005) "The Role of Intrathecal Drugs in the Treatment of Acute Pain," *Anesth. Analg*, 101, pp. S30-S43.

Ray, W.A., et al. [Abstract-Only] "COX-2 selective non-steroidal anti-inflammatory drugs and cardiovascular disease," Pharmacoepidemiol. Drug Saf., vol. 12, No. 1, Jan.-Feb. 2003, pp. 67-70.

Reske-Nielsen et al. (1970) "Pathological changes in the central and peripheral nervous system of young long-term diabetics," *Diabetologia*, 6:98-103.

Robbins, et al. (1990) "Inhibition of epoxide hydrolase by valproic acid in epileptic patients receiving carbamazepine," Br. J. clin. Pharmac., vol. 29, pp. 759-762.

Rose et al. (2010) "1-Aryl-3-(1-acylpiperidin-4-yl)urea inhibitors of human and murine soluble epoxide hydrolase: structure-activity relationships, pharmacokinetics, and reduction of inflammatory pain," *J Med Chem*, 53:7067-7075.

Sanchez-Borges, M. et al., [Abstract-Only] "Adverse reactions to selective cyclooxygenase-2 inhibitors (coxibs)," Am. J. Ther., vol. 11, No. 6, Nov.-Dec. 2004, pp. 494-500.

Schmelzer et al. (2005) "Soluble epoxide hydrolase is a therapeutic target for acute inflammation," *Proc Natl Acad Sci USA*, 102(28):9772-9777.

Schmelzer et al. "Enhancement of anitnociception by coadministration of nonsterioidal anti-inflammatory drugs and soluble epoxide hydrolase inhibitors," Proc. Natl. Acad. Sci., vol. 103, No. 37, Sep. 12, 2006, pp. 13646-13651.

Seibert, K. et al. (1994) [Abstract Only] "Role of inducible cyclooxygenase (COX-2) in inflammation," Receptor, 4:17-23.

Sekut et al. (1995) "Anti-inflammatory activity of phosphodiesterase (PDE)-IV inhibitors in acute and chronic models of inflammation," *Clin Exp Immunol*, 100:126-132.

(56) References Cited

OTHER PUBLICATIONS

Serhan, C. et al. (Jun. 2001) "Unorthodox routes to prostandoid formation: new twists in cyclooxygenase-initiated pathways," The Journal of Clinical Investigation, vol. 107, No. 12, pp. 1481-1489.
Sharma, J.N., et al. [Abstract-Only] "Adverse effects of COX-2 inhibitors," ScientificWorld Journal, Aug. 2005, vol. 18, No. 5, pp. 629-645.
Shen, et al., (2004) "Application of Predictive QSAR Models to Database Mining: Identification and Experimental Validation of Novel Anticonvulsant Compounds," J. Med. Chem., vol. 49, No. 9, pp. 2356-2364.
Simon, L.S., [Abstract-Only] "The COX-2 inhibitors: a reasoned review of the data," Swiss Med. Wkly., vol. 135, No. 29-30, Jul. 23, 2005, pp. 419-424.
Siuciak et al. (2007) "Antipsychotic profile of rolipram: efficacy in rats and reduced sensitivity in mice deficient in the phosphodiesterase-4B (PDE4B) enzyme," *Psychopharmacology*, 192:415-424.
Smith, et al. "Attenuation of tobacco smoke-induced lung inflammation by treatment with a soluble epoxide hydrolase inhibitor," Proc. Natl. Acad. ScI, USA, 102(6), pp. 2186-2191, Feb. 8, 2005.
Snider et al. (Apr. 1998) "Tackling Pain at the Source: New Ideas about Nociceptors," *Neuron*, 20:629-632.
Song et al. (2006) "cAMP and cGMP Contribute to Sensory Neuron Hyperexcitability and Hyperalgesia in Rats With Dorsal Root Ganglia Compression," *J Neurophysiol*, 95:479-492.
Strachan et al. (May 2014) Diabetes: "Cognitive decline and T2DM, a disconnect in the evidence?" *Nat Rev Endocrinol*, 10:258-260.
Suyama, et al. "Effect of etodolac, a COX-2 inhibitor, on neuropathic pain in a rat model" Brain Research, vol. 1010, No. 1-2, Jun. 4, 2004, pp. 144-150.
Taiwo et al. (1989) "Mediation of Primary Afferent Peripheral Hyperalgesia by the cAMP Second Messenger System," *Neuroscience*, 32(3):577-580.
Taiwo et al. (1991) "Further Confirmation of the Role of Adenyl Cyclase and of cAMP-Dependent Protein Kinase in Primary Afferent Hyperalgesia," *Neuroscience*, 44(1):131-135.
Taiwo et al. (1992) "Mediation of Serotonin Hyperalgesia by the cAMP Second Messenger System," *Neuroscience*, 48(2):479-483.
Tesfaye et al. (2013) "Mechanisms and management of diabetic painful distal symmetrical polyneuropathy," *Diab Care*, 36:2456-2465.

Thomas et al. (1965) "Schwann-Cell Abnormalities in Diabetic Neuropathy," *The Lancet*, 1:1355-1357.
Thomas et al. (1989) "Effect of diabetes and starvation on the activity of rat liver epoxide hydrolases, glutathione S-transferases and peroxisomal β-oxidation," *Biochem Pharmacol*, 38(23):4291-4297.
Toward, et al. (2004) "Effect of Phosphodiesterase-5 Inhibitor, Sildenafil (Viagra), in Animal Models of Airways Disease," American Journal of Respiratory and Critical Care Medicine, vol. 169, pp. 227-234.
Vranken, (2009) "Mechanisms and Treatment of Neuropathic Pain," Central Nervous System Agents in Medicinal Chemistry, vol. 9, pp. 71-78.
Wagner et al. (2014) "Soluble epoxide hydrolase inhibition is antinociceptive in a mouse model of diabetic neuropathy," *J Pain*, 15:907-914 [Accepted Manuscript], 30pp.
Walpole et al. (2012) "The weight of nations: an estimation of adult human biomass," BMC Public Health, 2012, 12:439, Jun. 18, 2012, pp. 1-6.
Wang (2012) "The impact of the unfolded protein response on human disease," J Cell Biol, 197(7):857-867.
Wang et al. (2006) "The involvement of epoxygenase metabolites of arachidonic acid in cAMP-stimulated steroidogenesis and steroidogenic acute regulatory protein gene expression," Journal of Endocrinology, 190(3):871-878.
Wang, et al. (2014) "Activated microglia in the spinal cord underlies diabetic neuropathic pain," European Journal of Pharmacology, 728, pp. 59-66.
Watowich et al. (Jan. 1988) "Complex regulation of heat shock- and glucose-responsive genes in human cells," Mol Cell Biol, 8(1):393-405.
Xu, et al., "Prevention and reversal of cardiac hypertrophy by soluble epoxide hydrolase inhibitors," PNAS, vol. 103, No. 49, Dec. 5, 2006, pp. 18733-18738.
Xu, Qinghao et al. (2011) "A brief comparison of the pathophysiology of inflammatory versus neuropathic pain," Current Opinion in Anesthesiology, 24:400-407.
Yang et al. (2008) "Characterization of epoxyeicosatrienoic acid binding site in U937 membranes using a novel radiolabeled agonist, 20-1251-14,15-Epoxyeicosa-8(Z)-Enoic Acid," Journal of Pharmacology and Experimental Therapeutics, 324(3):1019-1027.
Zavala, F. (1997) "Benzodiazepines, Anxiety and Immunity," Pharmacological Therapy, vol. 75, No. 3, pp. 199-216.

\* cited by examiner

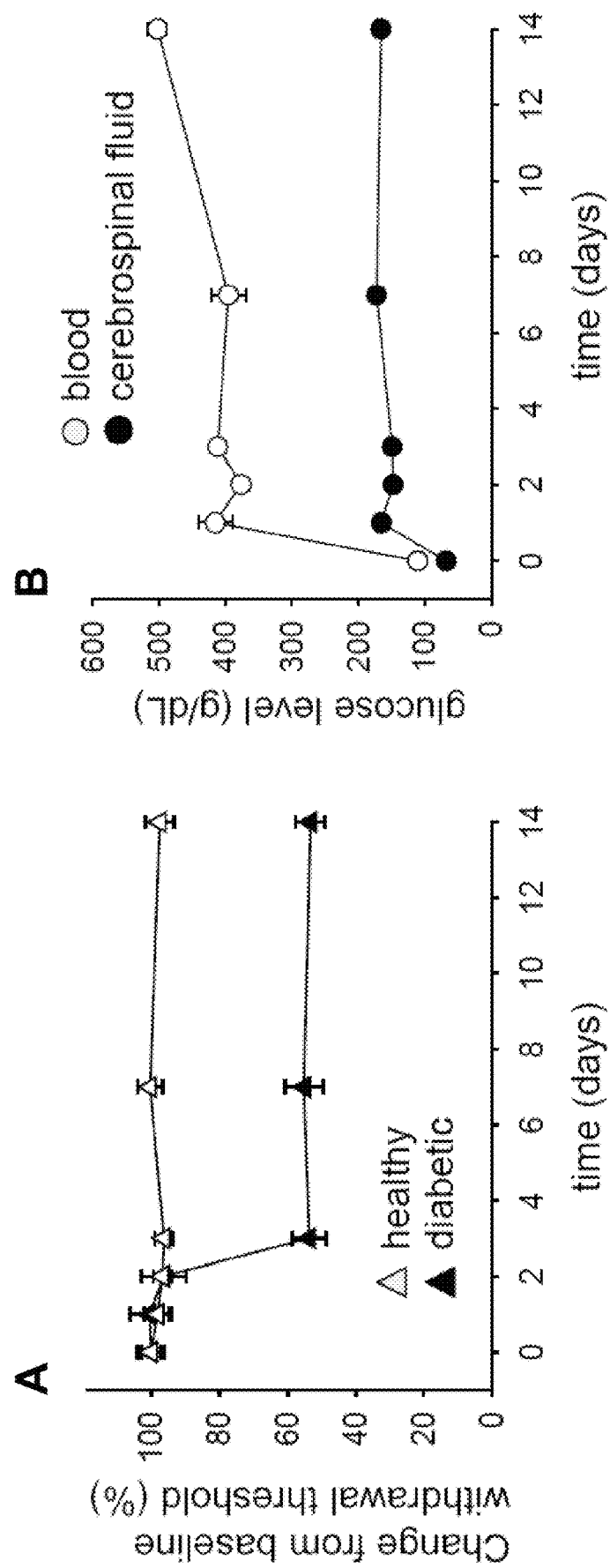
Fig. 1A-B

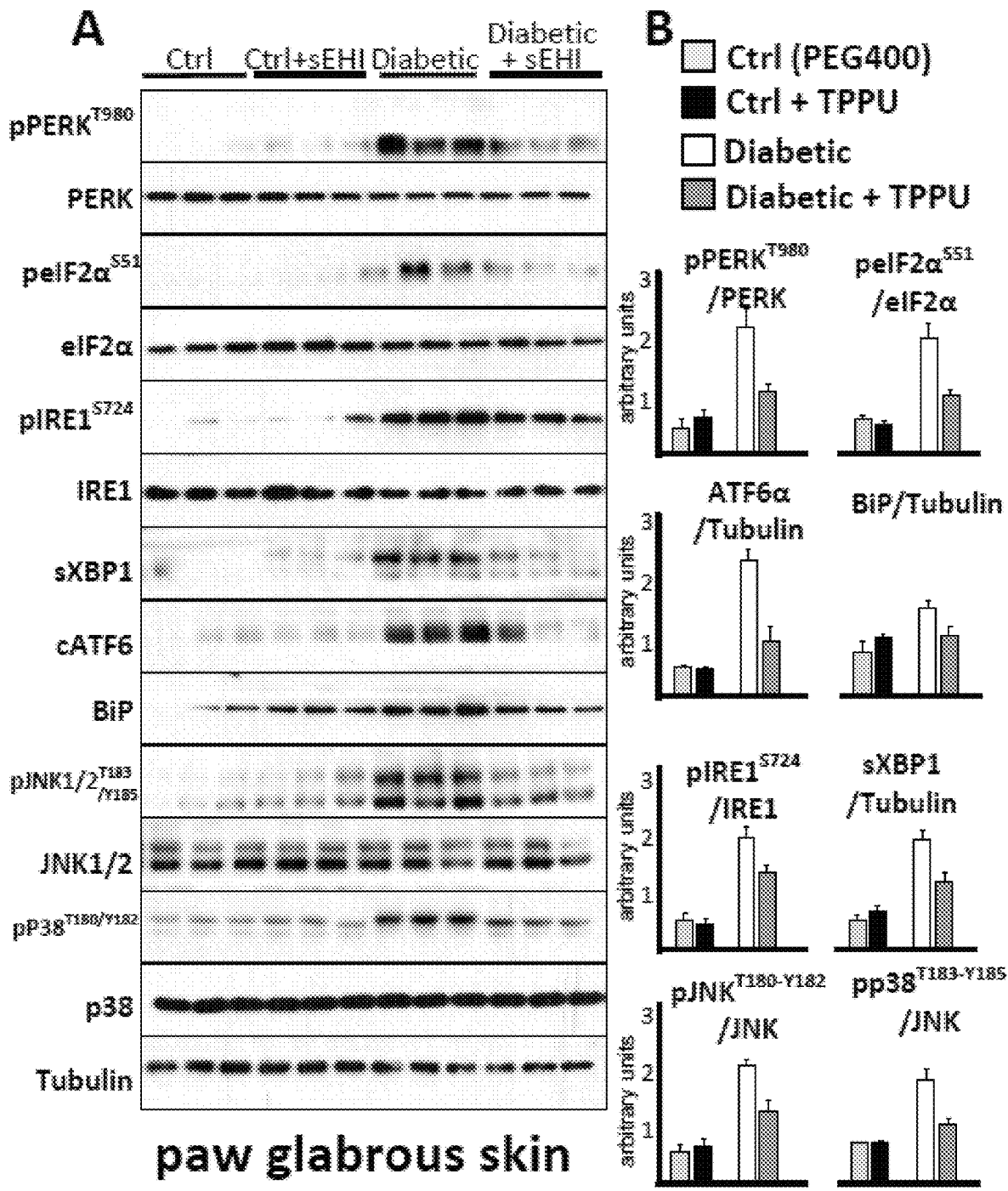
Fig. 2A-B

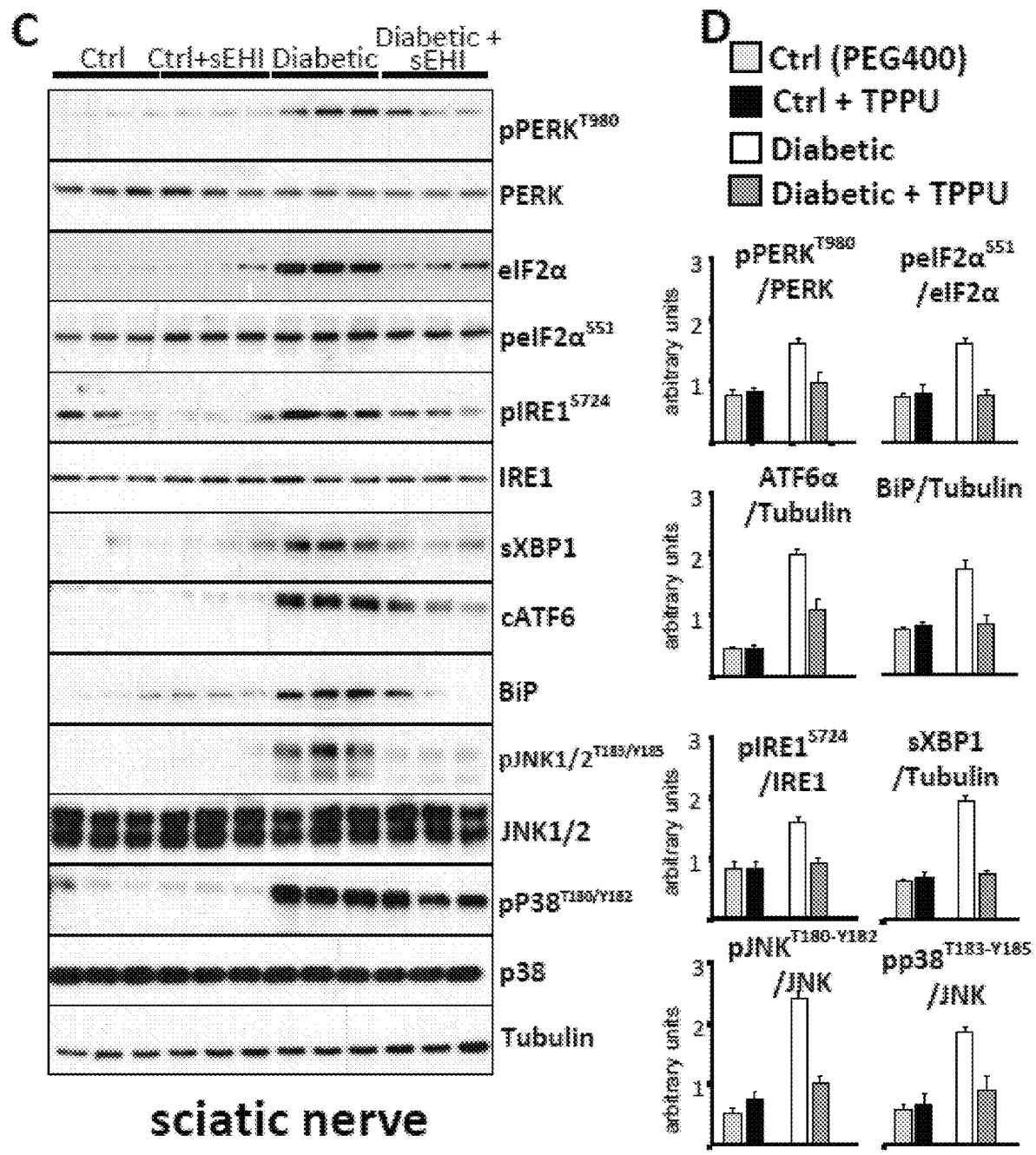
Fig. 2C-D

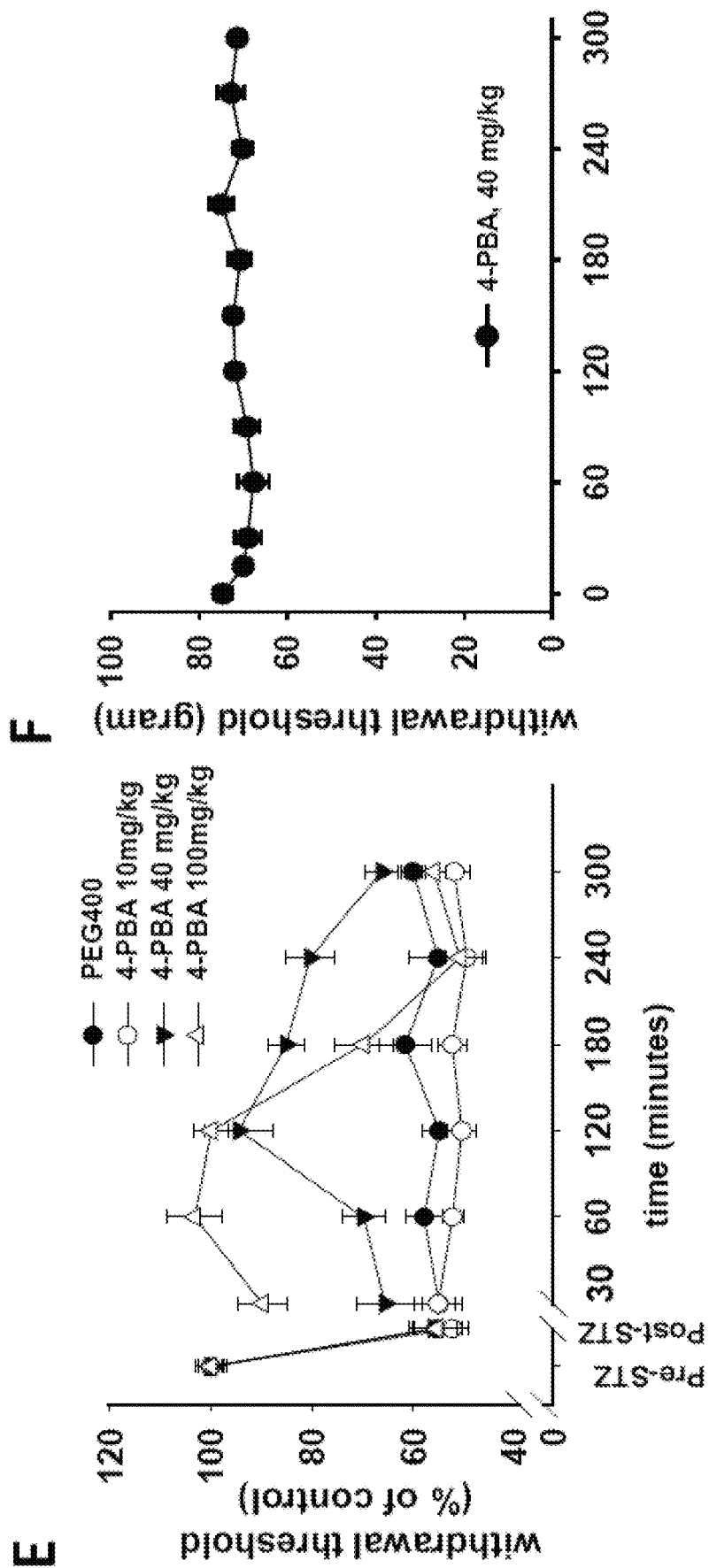
Fig. 2E-F

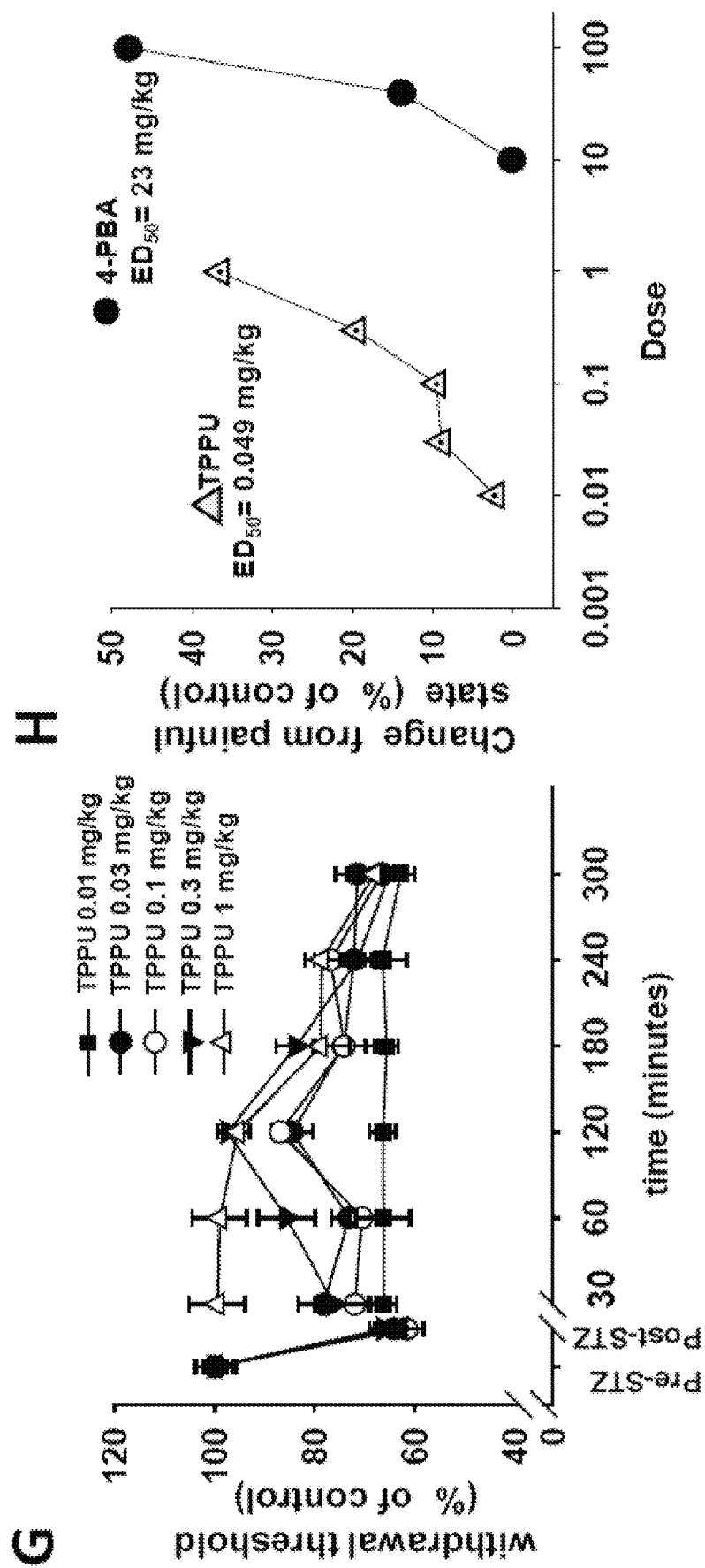
Fig. 2G-H

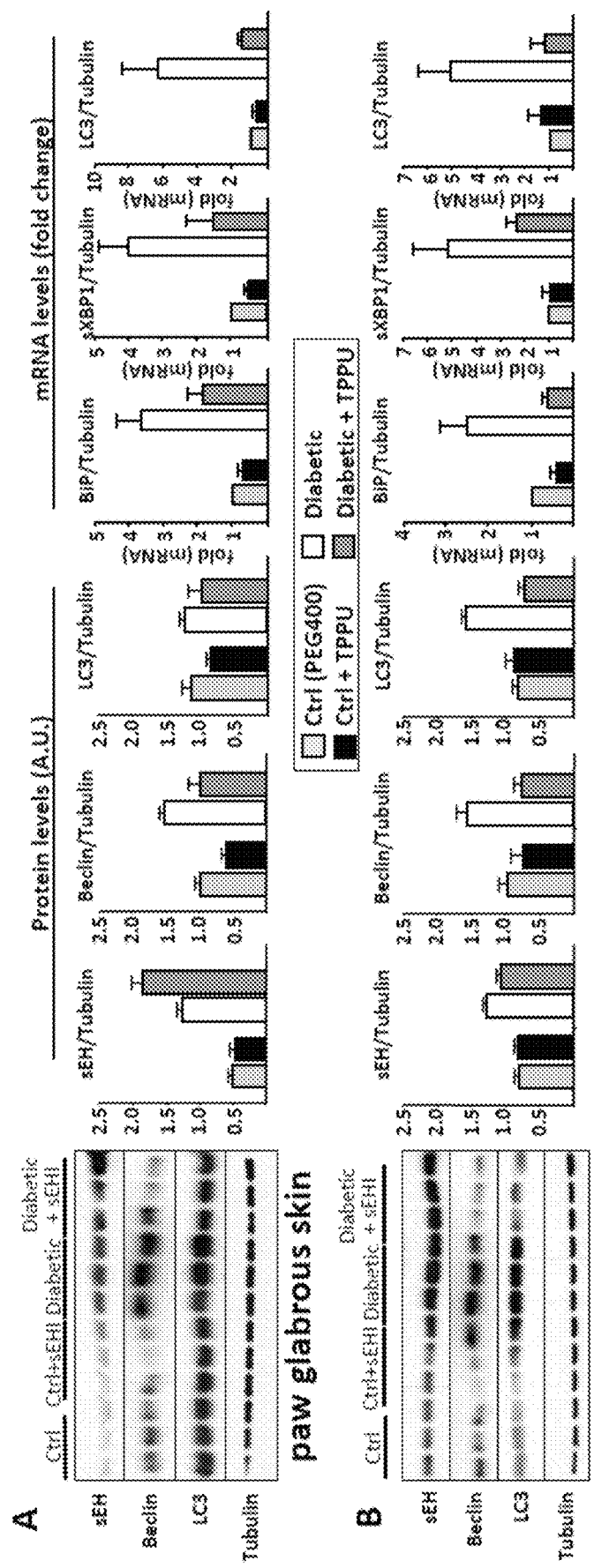
Fig. 5A-B

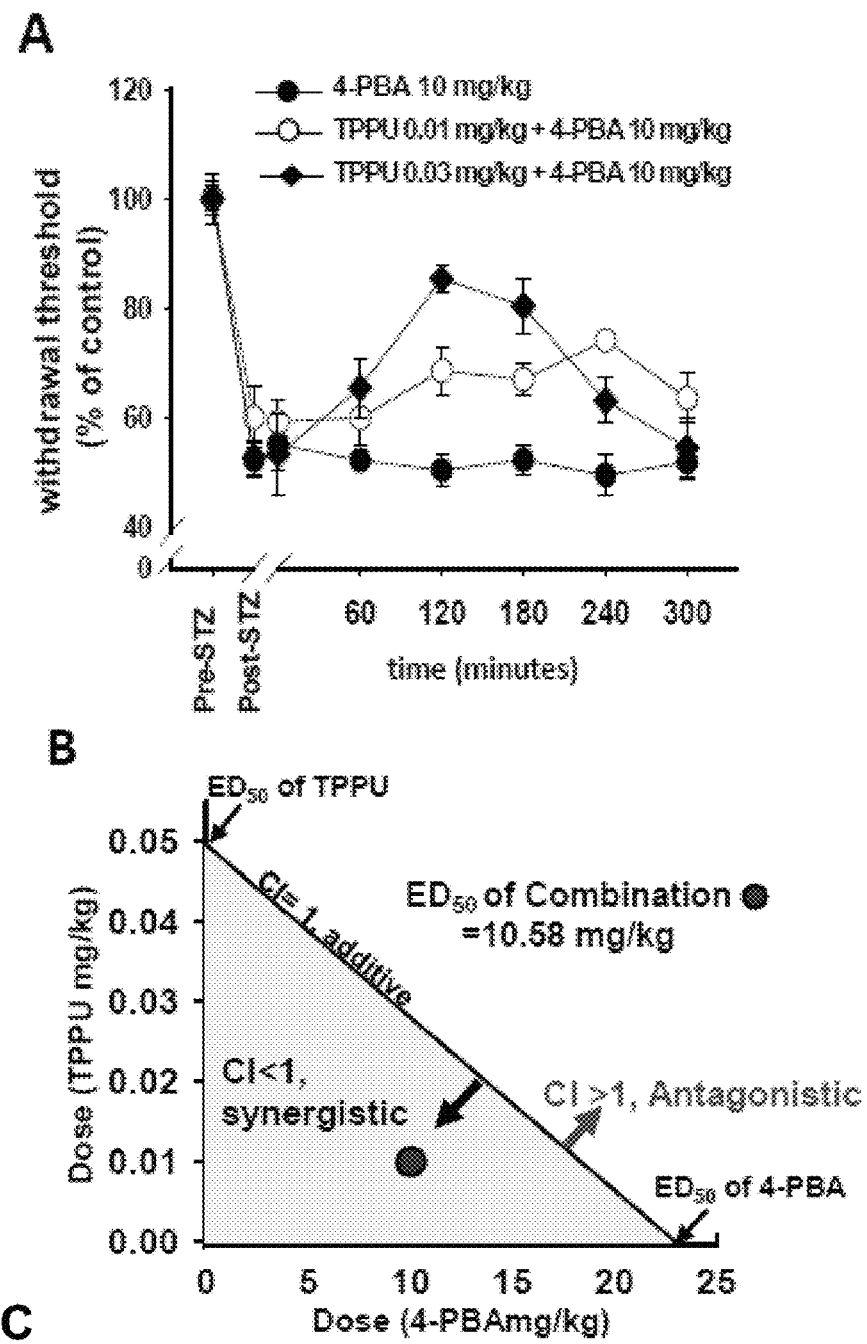
Fig. 6A-C

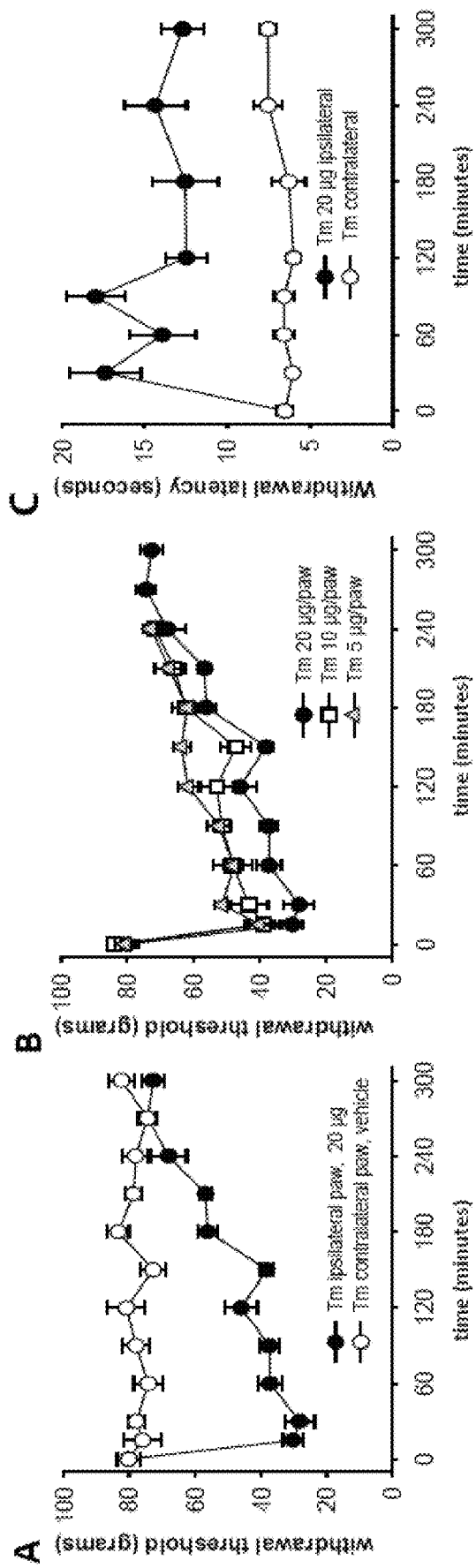
Fig. 7A-C

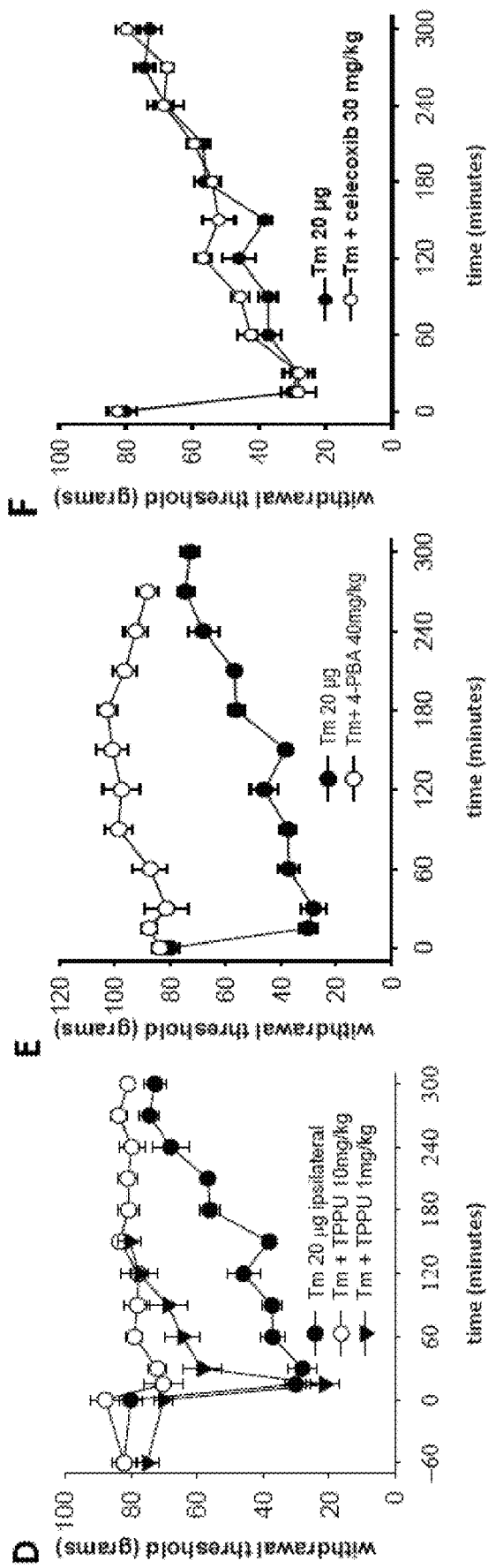
Fig. 7D-F

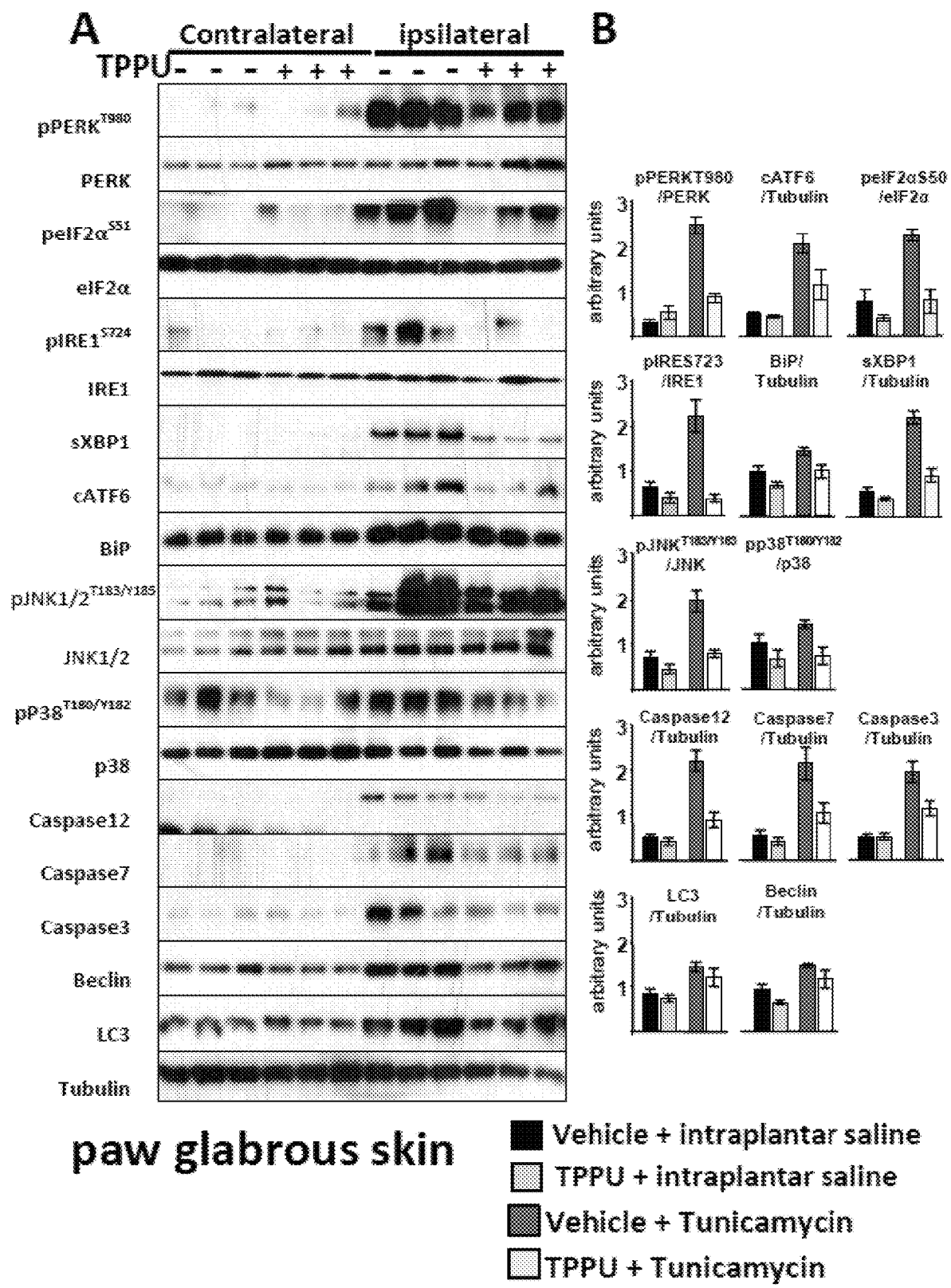
Fig. 8A-B

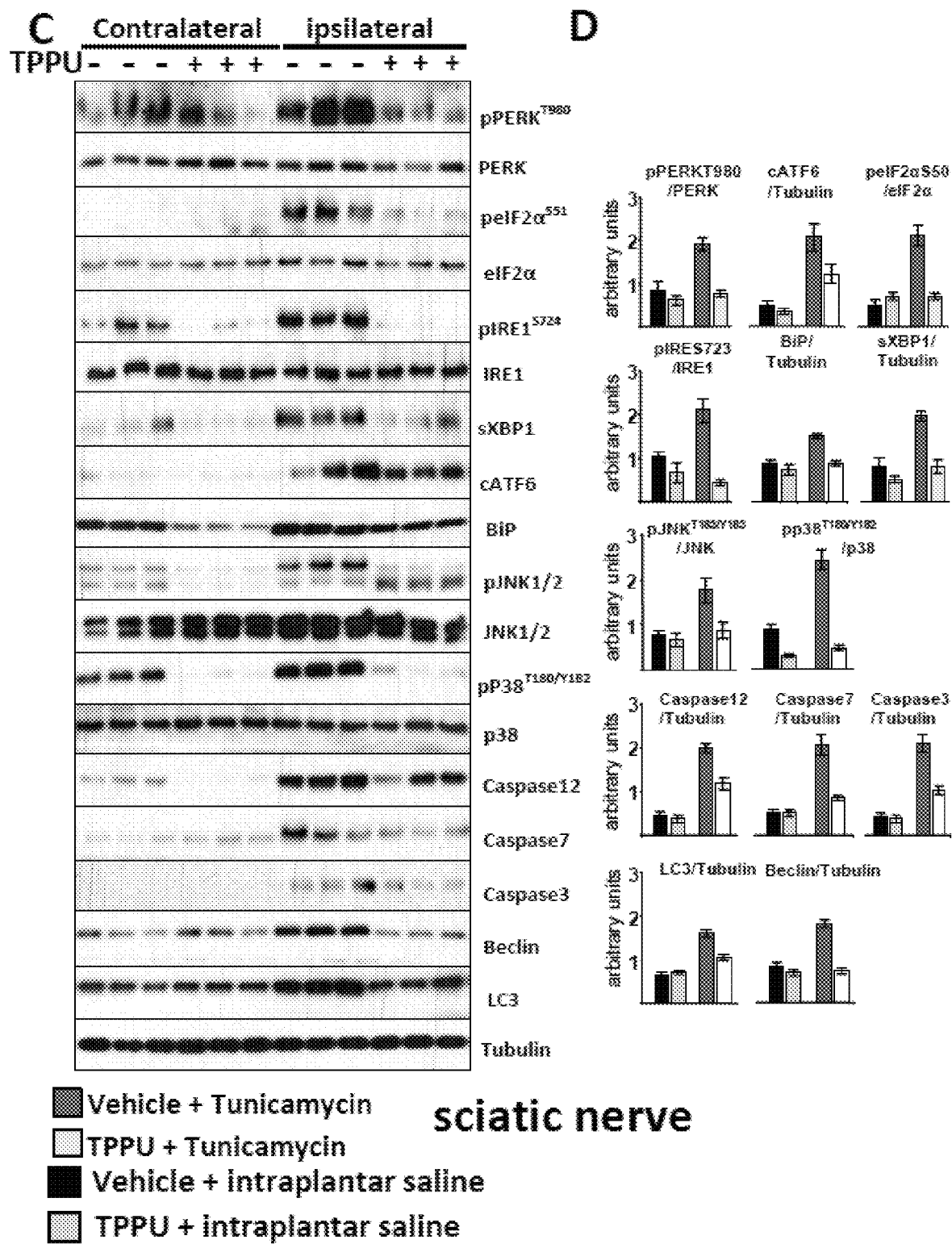
Fig. 8C-D

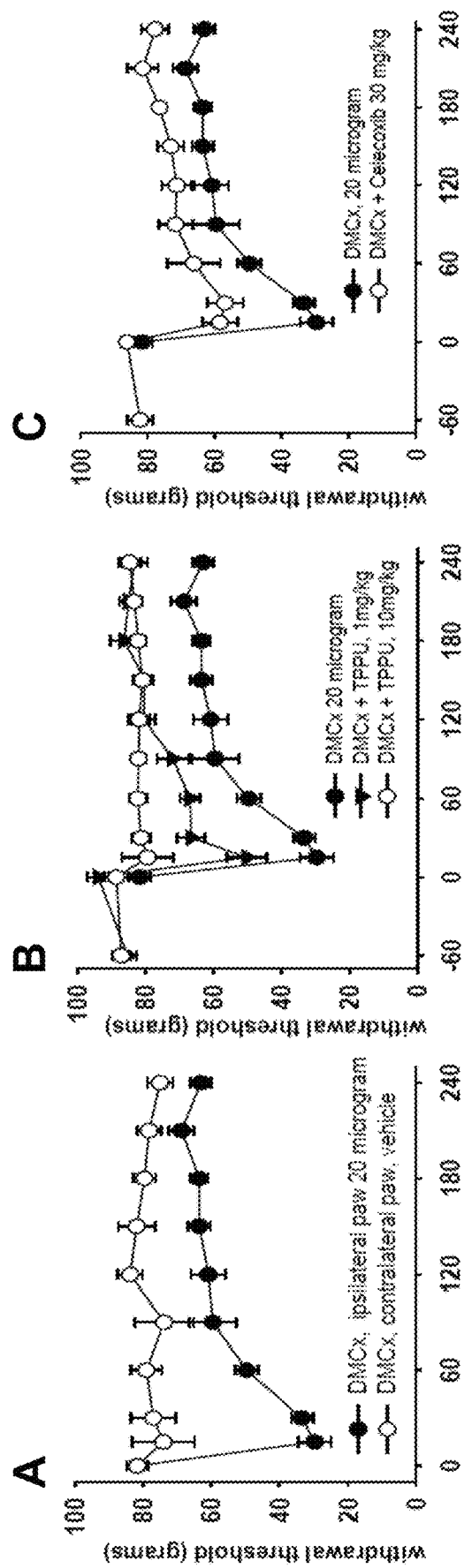
Fig. 9A-C

SEQUENCE LISTING

```
<160> NUMBER OF SEQ ID NOS: 38

<210> SEQ ID NO 1
<211> LENGTH: 554
<212> TYPE: PRT
<213> ORGANISM: Homo sapiens
```

<400> SEQUENCE: 1

```
Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30

Pro Arg Gly Leu Leu Asn Asp Ala Phe Gln Lys Gly Gly Pro Glu Gly
        35                  40                  45

Ala Thr Arg Leu Met Lys Gly Glu Ile Thr Leu Ser Gln Trp Ile
    50                  55                  60

Pro Leu Met Glu Glu Asn Cys Arg Lys Cys Ser Glu Thr Ala Lys Val
65                  70                  75                  80

Cys Leu Pro Lys Asn Phe Ser Ile Lys Glu Ile Phe Asp Lys Ala Ile
                85                  90                  95

Ser Ala Arg Lys Ile Asn Arg Pro Met Leu Gln Ala Ala Leu Met Leu
            100                 105                 110

Arg Lys Lys Gly Phe Thr Thr Ala Ile Leu Thr Asn Thr Trp Leu Asp
        115                 120                 125

Asp Arg Ala Glu Arg Asp Gly Leu Ala Gln Leu Met Cys Glu Leu Lys
    130                 135                 140

Met His Phe Asp Phe Leu Ile Glu Ser Cys Gln Val Gly Met Val Lys
145                 150                 155                 160

Pro Glu Pro Gln Ile Tyr Lys Phe Leu Leu Asp Thr Leu Lys Ala Ser
                165                 170                 175

Pro Ser Glu Val Val Phe Leu Asp Asp Ile Gly Ala Asn Leu Lys Pro
            180                 185                 190

Ala Arg Asp Leu Gly Met Val Thr Ile Leu Val Gln Asp Thr Asp Thr
        195                 200                 205

Ala Leu Lys Glu Leu Glu Lys Val Thr Gly Ile Gln Leu Leu Asn Thr
    210                 215                 220

Pro Ala Pro Leu Pro Thr Ser Cys Asn Pro Ser Asp Met Ser His Gly
225                 230                 235                 240

Tyr Val Thr Val Lys Pro Arg Val Arg Leu His Phe Val Glu Leu Gly
                245                 250                 255

Trp Pro Ala Val Cys Leu Cys His Gly Phe Pro Glu Ser Trp Tyr Ser
            260                 265                 270

Trp Arg Tyr Gln Ile Pro Ala Leu Ala Gln Ala Gly Tyr Arg Val Leu
        275                 280                 285

Ala Met Asp Met Lys Gly Tyr Gly Glu Ser Ser Ala Pro Pro Glu Ile
    290                 295                 300

Glu Glu Tyr Cys Met Glu Val Leu Cys Lys Glu Met Val Thr Phe Leu
305                 310                 315                 320

Asp Lys Leu Gly Leu Ser Gln Ala Val Phe Ile Gly His Asp Trp Gly
                325                 330                 335

Gly Met Leu Val Trp Tyr Met Ala Leu Phe Tyr Pro Glu Arg Val Arg
            340                 345                 350

Ala Val Ala Ser Leu Asn Thr Pro Phe Ile Pro Ala Asn Pro Asn Met
        355                 360                 365

Ser Pro Leu Glu Ser Ile Lys Ala Asn Pro Val Phe Asp Tyr Gln Leu
    370                 375                 380

Tyr Phe Gln Glu Pro Gly Val Ala Glu Ala Glu Leu Glu Gln Asn Leu
385                 390                 395                 400

Ser Arg Thr Phe Lys Ser Leu Phe Arg Ala Ser Asp Glu Ser Val Leu
```

```
                405                 410                 415
Ser Met His Lys Val Cys Glu Ala Gly Gly Leu Phe Val Asn Ser Pro
            420                 425                 430

Glu Glu Pro Ser Leu Ser Arg Met Val Thr Glu Glu Ile Gln Phe
            435                 440                 445

Tyr Val Gln Gln Phe Lys Lys Ser Gly Phe Arg Gly Pro Leu Asn Trp
            450                 455                 460

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
            500                 505                 510

Leu Lys Arg Gly His Ile Glu Asp Cys Gly His Trp Thr Gln Met Asp
            515                 520                 525

Lys Pro Thr Glu Val Asn Gln Ile Leu Ile Lys Trp Leu Asp Ser Asp
            530                 535                 540

Ala Arg Asn Pro Pro Val Val Ser Lys Met
545                 550

<210> SEQ ID NO 2
<211> LENGTH: 2100
<212> TYPE: DNA
<213> ORGANISM: Homo sapiens

<400> SEQUENCE: 2
ggcacgagct ctctctctct ctctctctct ctctcgccgc catgacgctg cgcggcgccg      60
tcttcgacct tgacggggtg ctggcgctgc cagcggtgtt cggcgtcctc ggccgcacgg     120 aggaggcccct ggcgctgccc agaggacttc tgaatgatgc tttccagaaa gggggaccag    180
agggtgccac tacccggctt atgaaaggag agatcacact tcccagtgg ataccactca      240 tggaagaaaa ctgcaggaag tgctccgaga ccgctaaagt ctgcctcccc aagaatttct     300
ccataaaaga aatctttgac aaggcgattt cagccagaaa gatcaaccgc ccatgctcc      360 aggcagctct catgctcagg aagaaaggat tcactactgc catcctcacc aacacctggc     420
tggacgaccg tgctgagaga gatggcctgg cccagctgat gtgtgagctg aagatgcact     480
ttgacttcct gatagagtcg tgtcaggtgg aatggtcaa acctgaacct cagatctaca      540
agtttctgct ggacaccctg aaggccagcc ccagtgaggt cgttttttg gatgacatcg      600 gggctaatct gaagccagcc cgtgacttgg gaatggtcac catcctggtc caggacactg     660
acacggccct gaaagaactg agaaagtgaa ccggaatcca gcttctcaat accccggccc    720
ctctgccgac ctcttgcaat ccaagtgaca tgagccatgg gtacgtgaca gtaaagccca    780
gggtccgtct gcatttttgtg gagctgggct ggcctgctgt gtgcctctgc catggatttc     840
ccgagagttg gtattcttgg aggtaccaga tccctgctct ggcccaggca ggttaccggg     900
tcctagctat ggacatgaaa ggctatggag agtcatctgc tcctcccgaa atagaagaat     960
attgcatgga agtgttatgt aaggagatgg taaccttcct ggataaactg ggcctctctc    1020
aagcagtgtt cattggccat gactgggtg cgatgctggt gtggtacatg gctctcttct     1080
accccgagag agtgagggcg gtggccagtt tgaatactcc cttcatacca gcaaatccca    1140
acatgtcccc tttggagagt atcaaagcca cccagtatt tgattaccag ctctacttcc    1200
aagaaccagg agtggctgag gctgaactgg aacagaacct gagtcggact ttcaaaagcc   1260
```

```
tcttcagagc aagcgatgag agtgttttat ccatgcataa agtctgtgaa gcgggaggac    1320
tttttgtaaa tagcccagaa gagcccagcc tcagcaggat ggtcactgag gaggaaatcc    1380
agttctatgt gcagcagttc aagaagtctg gtttcagagg tcctctaaac tggtaccgaa    1440
acatggaaag gaactggaag tgggcttgca aaagcttggg acggaagatc ctgattccgg    1500
ccctgatggt cacggcggag aaggacttcg tgctcgttcc tcagatgtcc cagcacatgg    1560
aggactggat tccccacctg aaaagggac  acattgagga ctgtgggcac tggacacaga    1620
tggacaagcc aaccgaggtg aatcagatcc tcattaagtg gctggattct gatgcccgga    1680
acccaccggt ggtctcaaag atgtagaacg cagcgtagtg cccacgctca gcaggtgtgc    1740
catccttcca cctgctgggg caccattctt agtatacaga ggtggcctta cacacatctt    1800
gcatggatgg cagcattgtt ctgaaggggt ttgcagaaaa aaaagatttt ctttacataa    1860
agtgaatcaa atttgacatt attttagatc ccagagaaat caggtgtgat tagttctcca    1920
ggcatgaatg catcgtccct ttatctgtaa gaacccttag tgtcctgtag ggggacagaa    1980
tggggtggcc agtggtgat  ttctctttga ccaatgcata gtttggcaga aaaatcagcc    2040
gttcatttag aagaatctta gcagagattg ggatgcctta ctcaataaag ctaagatgac    2100
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cagtgttcat tggccatgac tgg                                               23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
guguucauug gccaugacut t                                                 21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
agucauggcc aaugaacact t                                                 21

<210> SEQ ID NO 6
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 6
gaaaggctat ggagagtcat ctg                                            23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aaggcuaugg agagucauct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gaugacucuc cauagccuut t                                              21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
aaaggctatg gagagtcatc tgc                                            23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
aggcuaugga gagucaucut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: Description of Combined DNA/RNA Molecule:
      Synthetic oligonucleotide

<400> SEQUENCE: 11
agaugacucu ccauagccut t                                           21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caagcagtgt tcattggcca tga                                         23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agcaguguuc auuggccaut t                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
auggccaaug aacacugcut t                                           21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcacatgg aggactggat tcc                                         23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gcacauggag gacuggauut t                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
aauccagucc uccaugugct t                                          21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 ttcaagaga                                                         9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagtgttcat tggccatgac tgg                                        23

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gatccccgtg ttcattggcc atgactttca agagaagtca tggccaatga acactttt     59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agctaaaaag tgttcattgg ccatgacttc tcttgaaagt catggccaat gaacacggg    59

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaaggctat ggagagtcat ctg                                         23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gatccccaag gctatggaga gtcatcttca agagagatga ctctccatag cctttttt    59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agctaaaaaa aggctatgga gagtcatctc tcttgaagat gactctccat agccttggg   59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaggctatg gagagtcatc tgc                                         23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gatccccagg ctatggagag tcatctttca agagaagatg actctccata gccttttt    59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agctaaaaaa ggctatggag agtcatcatc tcttgaaaga tgactctcca tagcctggg   59

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caagcagtgt tcattggcca tga                                              23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatccccagc agtgttcatt ggccatttca agagaatggc caatgaacac tgcttttt       59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agctaaaaaa gcagtgttca ttggccattc tcttgaaatg gccaatgaac actgctggg      59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcacatgg aggactggat tcc                                              23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatccccgca catggaggac tggattttca agagaaatcc agtcctccat gtgctttt       59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agctaaaaag cacatggagg actggatttc tcttgaaaat ccagtcctcc atgtgcggg      59

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uguccagugc ccacaguccu                                              20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uucccaccug acacgacucu                                              20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
guucagccuc agccacuccu                                              20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
aguccucccg cuucacaga                                               19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gcccacuucc aguuccuuuc c                                            21

METHODS OF INHIBITING PAIN

CROSS REFERENCE TO RELATED APPLICATION

This application is the U.S. national phase under 35 U.S.C. § 371 of Intl. Appl. No. PCT/US2016/017613, filed on Feb. 11, 2016, which claims the benefit under 35 U.S.C. § 119(e) of U.S. Provisional Appl. No. 62/118,468, filed on Feb. 20, 2015, which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created on May 13, 2016, is named UCDVP113WO_SL.txt and is 17,305 bytes in size.

STATEMENT OF GOVERNMENTAL SUPPORT

This invention was made with government support under Grant Nos. 5R21AR062866 and 5R01ES002710, awarded by the National Institutes of Health. The government has certain rights in the invention.

FIELD

Provided are methods and compositions for preventing, reducing, mitigating and treating pain, particularly neuropathic pain by the combined administration of an agent that increases EETs and an agent that reduces/inhibits endoplasmic reticulum (ER) stress.

BACKGROUND

Limited success in therapeutic approaches for pain has been attained despite intensive efforts. Specifically, neuropathic pain continues to be an unmet clinical need. Drugs that target neuropathic pain do not resolve the underlying cause of pain. Specifically, current medications for diabetes-mediated pain target ion channels but they are largely ineffective in helping patients manage pain. Instead, pain therapeutics target the excitability of pain transmitting nerve cells. Currently, all FDA approved or off-label used analgesics for neuropathic pain work by suppressing nerve activity. Although this may be a good approach in certain cases, limitations include lack of broad efficacy and serious side effects associated with blocking all neural excitability in a non-selective manner. Therefore, current drugs do not provide satisfactory therapy to a large number of patients suffering from neuropathic pain. Therapeutics for pain, in particular nerve damage-induced pain remains a significant and unmet medical need. Almost one-third of chronic pain sufferers are resistant to all available therapeutic agents for managing their pain.

Following its discovery, ER (endoplasmic reticulum) stress and the ensuing UPR (unfolded protein response) proved to be a major adaptive and homeostatic mechanism that balances cells' demand for proteins to its synthetic output (1). If and when disequilibrium in demand and synthesis cannot be overcome, ER stress leads to activation of cell death pathways. ER stress seems necessary and sufficient for a number of pathologic states including diabetes and cancer (2). Specifically in the nervous system, key roles underlying multiple neurodegenerative diseases have been ascribed to ER stress. These include Alzheimer's and Parkinson's diseases, amyotrophic lateral sclerosis and prion diseases (3). In these conditions disruption of homeostasis leads to plaque formation, neuronal loss and ultimately to dysfunction. However beyond the progressive neurodegenerative diseases typically manifesting over the long term little is known about how ER stress affects the nervous system. Regardless, current ideas on ER stress in the nervous system can be epitomized as a fundamental and sentient network modulating physiologic responses. As such, discovery of mechanisms governing ER stress in neurons should significantly enhance our basic understanding of normal physiology and etiology of diseases of the PNS.

Diabetes induced neuropathic phenotype in rodents and man displays progressively increasing pain in response to tactile stimulation and a loss of sensitivity to heat. First documented in the 19th century, its basis has been debated continuously since then. Over the past century extensive histological changes in the diabetic PNS are demonstrated (4). However, paradoxically, these changes include signs of both destructive and regenerative biological events. The main histopathological features include axonal swelling, dying back of fibers, demyelination and degeneration, Schwann cell atrophy, signs of remyelination, distal sprouting of proximal nerve stumps. Moreover, cognitive decline and atrophy in the brain and spinal cord are frequently observed, suggesting that hallmark features extend to the central nervous system (5,6). The distinctive sensory changes—also used to diagnose diabetes induced nerve damage—often coincide with the characteristic features at the cellular level. These seem to occur in a selective manner, beginning from distal areas, and not all nerves display damage equally or at the least with an identical time course. The mechanism(s) governing these changes continue to spur debate, given the symptoms at the cellular level are unlike any other condition. However, they are remarkably similar to symptoms that would be expected from cells undergoing ER stress responses.

While studying the effects of inhibiting sEH on pain and inflammation, we reported that this enzyme is up regulated in the nervous system of diabetic rodents (7). Similarly liver, heart and adipose tissue sEH expression is elevated arguing for a global increase in response to diabetes (8-10). The increase in activity contributes to dyslipidemia because sEH selectively degrades low-abundance but highly potent bioactive lipids that maintain homeostasis. These lipids, also termed epoxy fatty acids (EpFAs), have analgesic, anticonvulsant and anti-inflammatory properties (11-14).

Thus, when EpFAs are stabilized by inhibiting sEH in diabetic animals, neuropathic pain is effectively blocked (15). Over the past three decades a large number of biological effects have been attributed to EpFAs (16). The mechanism responsible for antinociception is conceivably different than other reported activities of EpFAs. However, one particular activity stands out as a potentially overarching molecular mechanism that could underlie numerous and seemingly independent effects. Inhibition of sEH or genetic ablation has a profound effect in suppressing ER stress in the liver and adipose tissues of mice fed a high-fat diet (17).

SUMMARY

In one aspect, provided are methods of preventing, reducing, ameliorating, mitigating, inhibiting and/or reversing pain in a subject in need thereof. In some embodiments, the methods comprise co-administering to the subject an agent that increases the production and/or level of epoxygenated fatty acids and an inhibitor of endoplasmic reticulum stress. In varying embodiments, the pain comprises inflammatory pain. In varying embodiments, the pain comprises neuropathic pain. In varying embodiments, the neuropathic pain comprises nerve damage induced pain. In varying embodiments, the neuropathic pain is central neuropathic pain. In varying embodiments, the neuropathic pain is peripheral neuropathic pain. In varying embodiments, the neuropathic pain is characterized by one or more symptoms selected from the group consisting of paresthesia, dysesthesia, hypoesthesia, hyperesthesia, hypoalgesia, hyperalgesia and allodynia. In varying embodiments, other functions of the nervous system such as physiologic ion channel activity are not affected. In varying embodiments, the subject has diabetes. In a further aspect, provided are methods of preventing, reducing, ameliorating, mitigating, inhibiting and/or reversing one or more symptoms associated with a disease or disease condition caused at least in part by endoplasmic reticulum stress in a subject in need thereof. In varying embodiments, the methods comprise co-administering to the subject an agent that increases the production and/or level of epoxygenated fatty acids and an inhibitor of endoplasmic reticulum stress, wherein the disease or disease condition is selected from the group consisting of inflammatory disease, cardiovascular disease, pulmonary disease, renal disease, diabetes, neurological disease, hypertension, pulmonary edema, pulmonary hypertension, cystic fibrosis, cardiomyopathy, hypertrophy of the heart, edema, pain, epilepsy, neuroma, cancer, Alzheimer's disease, dementia, Amyotrophic Lateral Sclerosis (ALS), Parkinson's disease, prion diseases, depression, schizophrenia, and chemotherapy induced side effects. In varying embodiments, the preventing, reducing, ameliorating, mitigating, inhibiting and/or reversing of the pain or the one or more symptoms associated with a disease or disease condition is experienced by or effected in the subject within 24 hours, e.g., within 20, 18, 12, 10, 8, 6, 4, 2, 1 hours or fewer hours, or effected immediately. In varying embodiments, one or both of the agent that increases the production and/or level of epoxygenated fatty acids and the inhibitor of endoplasmic reticulum stress are administered at a subtherapeutic dose. In varying embodiments, the agent that increases the production and/or level of epoxygenated fatty acids and the inhibitor of endoplasmic reticulum stress are concurrently co-administered. In varying embodiments, the agent that increases the production and/or level of epoxygenated fatty acids and the inhibitor of endoplasmic reticulum stress are sequentially co-administered. In varying embodiments, the inhibitor of endoplasmic reticulum stress is selected from the group consisting of 4-phenyl butyric acid ("PBA"), 3-phenylpropionic acid (3-PPA), 5-phenylvaleric acid (5-PVA), 6 phenylhexanoic acid (6-PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO and mixtures thereof. In varying embodiments, the inhibitor of endoplasmic reticulum stress is selected from the group consisting of 4-phenyl butyric acid (4-PBA), 3-phenylpropionic acid (3-PPA), 5-phenylvaleric acid (5-PVA), 6-phenylhexanoic acid (6-PHA), esters thereof (e.g., esters of 4-phenyl butyric acid (4-PBA), 3-phenylpropionic acid (3-PPA), 5-phenylvaleric acid (5-PVA), 6 phenylhexanoic acid (6-PHA)), pharmaceutically acceptable salts thereof (e.g., salts of 4-phenyl butyric acid (4-PBA), 3-phenylpropionic acid (3-PPA), 5-phenylvaleric acid (5-PVA), 6 phenylhexanoic acid (6-PHA)), and mixtures thereof. In varying embodiments, the inhibitor of endoplasmic reticulum stress performs one or more of the following: a) prevents, reduces and/or inhibits phosphorylation of PERK (Thr980), Ire1α (Ser727), eIF2α (Ser51), p38 and/or JNK1/2; b) prevents, reduces and/or inhibits cleavage of ATF6 and/or XBP1; and/or c) prevents, reduces and/or inhibits mRNA expression of BiP, ATF4 and/or XBP1. In varying embodiments, the agent that increases the production and/or level of epoxygenated fatty acids comprises one or more epoxygenated fatty acids. In varying embodiments, the epoxygenated fatty acids are selected from the group consisting of cis-epoxyeicosantrienoic acids ("EETs"), epoxides of linoleic acid, epoxides of eicosapentaenoic acid ("EPA"), epoxides of docosahexaenoic acid ("DHA"), epoxides of the arachidonic acid ("AA"), epoxides of cis-7,10,13,16,19-docosapentaenoic acid, and mixtures thereof. In varying embodiments, the agent that increases the production and/or level of epoxygenated fatty acids increases the production and/or levels of cis-epoxyeicosantrienoic acids ("EETs"). In varying embodiments, the agent that increases the production and/or level of EETs is an inhibitor of soluble epoxide hydrolase ("sEH"). In varying embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM, e.g., less than about 50 µM, 40 µM, 30 µM, 25 µM, 20 µM, 15 µM, 10 µM, 5 µM, 3 µM, 2 µM, 1 µM, 100 nM, 10 nM, 1.0 nM, or even less. In varying embodiments, the inhibitor of sEH is co-administered at a subtherapeutic dose. In varying embodiments, the subject is a human.

In a further aspect, provided are kits. In varying embodiments, the kits comprise an agent that increases the production and/or level of epoxygenated fatty acids and an inhibitor of endoplasmic reticulum stress. In varying embodiments, the inhibitor of endoplasmic reticulum stress is selected from the group consisting of 4-phenyl butyric acid ("PBA"), 3 phenylpropionic acid (3-PPA), 5-phenylvaleric acid (5-PVA), 6-phenylhexanoic acid (6 PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO and mixtures thereof. In varying embodiments, the inhibitor of endoplasmic reticulum stress is selected from the group consisting of 4-phenyl butyric acid (4-PBA), 3 phenylpropionic acid (3-PPA), 5-phenylvaleric acid (5-PVA), 6-phenylhexanoic acid (6 PHA), esters thereof (e.g., esters of 4-phenyl butyric acid (4-PBA), 3-phenylpropionic acid (3-PPA), 5-phenylvaleric acid (5-PVA), 6 phenylhexanoic acid (6-PHA)), pharmaceutically acceptable salts thereof (e.g., salts of 4-phenyl butyric acid (4-PBA), 3-phenylpropionic acid (3-PPA), 5-phenylvaleric acid (5-PVA), 6 phenylhexanoic acid (6-PHA)), and mixtures thereof. In varying embodiments, the agent that increases the production and/or level of EETs is an inhibitor of soluble epoxide hydrolase ("sEH"). In varying embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM, e.g., less than about 50 µM, 40 µM, 30 µM, 25 µM, 20 µM, 15 µM, 10 µM, 5 µM, 3 µM, 2 µM, 1 µM, 100 nM, 10 nM, 1.0 nM, or even less.

In a further aspect, provided are methods of preventing, reducing, ameliorating, mitigating, inhibiting and/or reversing pain in a subject in need thereof. In varying embodiments, the methods comprise administering to the subject an inhibitor of endoplasmic reticulum stress, wherein the preventing, reducing, ameliorating, mitigating, inhibiting and/or reversing of the pain or the one or more symptoms associated with a disease or disease condition is experienced by the subject within 24 hours, e.g., within 20, 18, 12, 10, 8, 6, 4, 2, 1 hours or fewer hours, or effected immediately. In varying embodiments, the pain comprises inflammatory pain. IN varying embodiments, the pain comprises neuropathic pain. In varying embodiments, the neuropathic pain comprises nerve damage induced pain. In varying embodiments, the neuropathic pain is central neuropathic pain. In varying embodiments, the neuropathic pain is peripheral neuropathic pain. In varying embodiments, the neuropathic pain is characterized by one or more symptoms selected from the group consisting of paresthesia, dysesthesia, hypoesthesia, hyperesthesia, hypoalgesia, hyperalgesia and allodynia. In varying embodiments, other functions of the nervous system such as physiologic ion channel activity are not affected. In varying embodiments, the subject has diabetes. Further provided are methods of preventing, reducing, ameliorating, mitigating, inhibiting and/or reversing one or more symptoms associated with a disease or disease condition caused at least in part by endoplasmic reticulum stress in a subject in need thereof. In some embodiments, the methods comprise administering to the subject an inhibitor of endoplasmic reticulum stress, wherein the disease or disease condition is selected from the group consisting of inflammatory disease, cardiovascular disease, pulmonary disease, renal disease, diabetes, neurological disease, hypertension, pulmonary edema, pulmonary hypertension, cystic fibrosis, cardiomyopathy, hypertrophy of the heart, edema, pain, epilepsy, neuroma, cancer, Alzheimer's disease, dementia, Amyotrophic Lateral Sclerosis (ALS), Parkinson's disease, prion diseases, depression, schizophrenia, and chemotherapy induced side effects, wherein the preventing, reducing, ameliorating, mitigating, inhibiting and/or reversing of the pain or the one or more symptoms associated with a disease or disease condition is experienced by the subject within 24 hours, e.g., within 20, 18, 12, 10, 8, 6, 4, 2, 1 hours or fewer hours, or effected immediately. In varying embodiments, the inhibitor of endoplasmic reticulum stress is selected from the group consisting of 4-phenyl butyric acid ("PBA"), 3-phenylpropionic acid (3-PPA), 5-phenylvaleric acid (5-PVA), 6 phenylhexanoic acid (6-PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO and mixtures thereof. In varying embodiments, the inhibitor of endoplasmic reticulum stress is selected from the group consisting of 4-phenyl butyric acid (4-PBA), 3-phenylpropionic acid (3-PPA), 5-phenylvaleric acid (5-PVA), 6 phenylhexanoic acid (6-PHA), esters thereof, pharmaceutically acceptable salts thereof, and mixtures thereof. In varying embodiments, the inhibitor of endoplasmic reticulum stress performs one or more of the following: a) prevents, reduces and/or inhibits phosphorylation of PERK (Thr980), Ire1α (Ser727), eIF2α (Ser51), p38 and/or JNK1/2; b) prevents, reduces and/or inhibits cleavage of ATF6 and/or XBP1; and/or c) prevents, reduces and/or inhibits mRNA expression of BiP, ATF4 and/or XBP1.

In a further aspect, provided are method of screening agents for efficacy in preventing, reducing, ameliorating, mitigating and/or inhibiting pain in a non-human mammal. In some embodiments, the methods comprise: a) administering to the non-human mammal an agent that induces endoplasmic reticulum stress, thereby inducing pain or hyperalgesia in the mammal; b) administering to the subject one or more test agents suspected of having efficacy in preventing, reducing, ameliorating, mitigating and/or inhibiting pain in the mammal; c) exposing the mammal to a stimulus capable of causing pain or hyperalgesia; and d) comparing the response of the test mammal to a control mammal that has been administered the agent that induces endoplasmic reticulum stress but has not been administered the one or more test agents suspected of having efficacy in preventing, reducing, ameliorating, mitigating and/or inhibiting pain in the mammal. In varying embodiments, the non-human mammal is a rodent. In varying embodiments, the non-human mammal is a rat or a mouse. In varying embodiments, the pain comprises inflammatory pain. In varying embodiments, the pain comprises neuropathic pain. In varying embodiments, the agent that induces endoplasmic reticulum stress is selected from tunicamycin, dimethylcelecoxib (DMCx), and mixtures thereof. In varying embodiments, the one or more test agents comprises an inhibitor of endoplasmic reticulum stress. In varying embodiments, the inhibitor of endoplasmic reticulum stress is selected from the group consisting of 4-phenyl butyric acid ("PBA"), 3 phenylpropionic acid (3-PPA), 5-phenylvaleric acid (5-PVA), 6-phenylhexanoic acid (6-PHA), butyrate, tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide, DMSO, and mixtures thereof. In varying embodiments, the inhibitor of endoplasmic reticulum stress is selected from the group consisting of 4-phenyl butyric acid (4-PBA), 3 phenylpropionic acid (3-PPA), 5-phenylvaleric acid (5-PVA), 6-phenylhexanoic acid (6-PHA), esters thereof (e.g., esters of 4-phenyl butyric acid (4-PBA), 3-phenylpropionic acid (3-PPA), 5-phenylvaleric acid (5-PVA), 6 phenylhexanoic acid (6-PHA)), pharmaceutically acceptable salts thereof (e.g., salts of 4-phenyl butyric acid (4-PBA), 3-phenylpropionic acid (3-PPA), 5-phenylvaleric acid (5-PVA), 6 phenylhexanoic acid (6-PHA)), and mixtures thereof. In varying embodiments, the one or more test agents comprises an agent that increases the production and/or level of epoxygenated fatty acids. In varying embodiments, the agent that increases the production and/or level of EETs is an inhibitor of soluble epoxide hydrolase ("sEH"). In varying embodiments, the inhibitor of sEH comprises a primary pharmacophore selected from the group consisting of a urea, a carbamate, and an amide. In varying embodiments, the inhibitor of sEH comprises a cyclohexyl moiety, aromatic moiety, substituted aromatic moiety or alkyl moiety attached to the pharmacophore. In varying embodiments, the inhibitor of sEH comprises a cyclohexyl ether moiety attached to the pharmacophore. In varying embodiments, the inhibitor of sEH comprises a phenyl ether or piperidine moiety attached to the pharmacophore. In varying embodiments, the inhibitor of sEH comprises a polyether secondary pharmacophore. In varying embodiments, the inhibitor of sEH has an IC50 of less than about 100 µM, e.g., less than about 50 µM, 40 µM, 30 µM, 25 µM, 20 µM, 15 µM, 10 µM, 5 µM, 3 µM, 2 µM, 1 µM, 100 nM, 10 nM, 1.0 nM, or even less. In varying embodiments, the stimulus is selected from the group consisting of a mechanical stimulus, a thermal stimulus and a chemical stimulus.

In a further aspect, provided are methods of preventing, reducing, ameliorating, mitigating, inhibiting and/or reversing a biological pathway that leads to generation and maintenance of pain in mammals which is the basis for new pain assays to discover drugs.

In a further aspect, provided are methods of preventing, reducing, ameliorating, mitigating, inhibiting and/or reversing pain in a subject in need thereof, comprising administering to the subject a molecular chaperone which facilitates correct protein folding or prevents protein aggregation, alone or co-administered with an agent that increases epoxy fatty acids.

In a further aspect, provided are methods of preventing, reducing, ameliorating, mitigating, inhibiting and/or reversing pain in a subject in need thereof, comprising administering to the subject agents that reduce or inhibit endoplasmic reticulum stress whether by correcting protein folding, regulating glucose homeostasis or reducing lipid overload, based on the dislipidemic conditions mediated by saturated fatty acid induced endoplasmic reticulum stress.

In a further aspect, provided are methods of preventing, reducing, ameliorating, mitigating, inhibiting and/or reversing pain in a subject in need thereof, comprising administering to the subject agents that block the de novo synthesis of proteins and the transcription of mRNA message or mRNA catalytic activity that are involved in pain and that reduce the toxicity of synthesis or transport restraints in neurons to relieve endoplasmic reticulum stress along with reducing pain.

In a further aspect, provided are compositions comprising agents that are otherwise known to be hazardous and toxic but used at much lower and non-toxic dose levels to synergize the pain blocking effects of protein or small molecule chaperones and their mimics or natural epoxy fatty acids, their mimics and small molecule inhibitors that stabilize epoxy fatty acids such as inhibitors of the soluble epoxide hydrolase.

In a further aspect, provided are compositions comprising that are otherwise known to be effective but used at much lower subtherapeutic dose levels to synergize the pain blocking effects of protein or small molecule chaperones and their mimics or natural epoxy fatty acids, their mimics and small molecule inhibitors that stabilize epoxy fatty acids such as inhibitors of the soluble epoxide hydrolase.

In a further aspect, provided are compositions comprising an ER stress-reducing agent, e.g., such as 4-phenyl butyric acid, the natural bile acid tauroursodeoxycholic acid, natural alpha-linked disaccharide trehalose, other polyols, polyphosphates, deuterated water or food ingredients such as omega-3 fats EPA and DHA and vitamin C and other cellular osmolytes that are amino acids or derivatives, carbohydrates such as arabitol, mannose, glycerol and others and methylamines such as betaine, sarcosine, trimethylamine-N oxide and natural epoxy fatty acids, their mimics and a small molecule inhibitor that stabilizes epoxy fatty acids such as inhibitors of the soluble epoxide hydrolase.

In a further aspect, provided are compositions comprising in subtherapeutic doses combinations of sEH inhibitors, epoxy fatty acids or their mimics and chaperone molecules or their mimics, protein synthesis inhibitors, mRNA transcription inhibitors.

Further provided are methods and compositions that targets known individual or multiple components of the endoplasmic reticulum stress pathway to block pain either as individual agents or as synergistic combinations.

Further provided are methods of blocking pain using the compositions described above and herein, e.g., by blocking apoptosis in the neural tissues.

Further provided are methods of blocking pain using the compositions described above and herein, e.g., by modulating autophagy in the neural tissues.

Further provided are methods of blocking pain by targeting the phosphorylation of PERK and IRE-1 or processing of cATF6 or logically targeting upstream or downstream molecular targets including but not limited to phosphorylation of IEF2-alpha, phosphorylation of JNK, phosphorylation of p38, cleavage of XBP1 mRNA or upregulation of BiP.

Further provided are methods of rapidly blocking pain in mammalian subjects within hours or more preferably within minutes following administration, by targeting the previously activated endoplasmic reticulum stress pathways, phosphorylation of PERK and IRE-1 or processing of cATF6 and upstream or downstream molecular targets from these processes by providing compositions in a therapeutic manner.

Further provided are methods of rapidly blocking pain in human and animal subjects within hours or more preferably within minutes by targeting the activation of endoplasmic reticulum stress, phosphorylation of PERK and IRE-1 or processing of cATF6 and upstream or downstream molecular targets from this process by providing compositions in a prophylactic manner, such as prior to a surgical intervention.

Further provided are methods of blocking pain while sparing other functions of the nervous system such as physiologic ion channel activity.

Further provided are methods of using the chaperone 4-phenyl butyric acid or butyrate or pharmacologically acceptable salts and formulations thereof to block neuropathic pain.

Further provided are methods of using chaperone 4-phenyl butyric acid or butyrate or pharmacologically acceptable salts and formulations thereof to block diabetes and co-morbidities of diabetes such as pain and cardiomyopathy or more generally defects of the autonomic nervous system.

Further provided are methods of using chaperones and other agents that target the endoplasmic reticulum stress pathways as synergists for diseases that are treatable by inhibitors of sEH and epoxy fatty acids including EpETrEs, EpETEs and EpDPEs and their synthetic mimics including but not limited to multiple forms of inflammatory, cardiovascular, pulmonary, renal, diabetic, neurological and tumorigenic conditions such as hypertension, pulmonary edema and pulmonary hypertension, cystic fibrosis, hypertrophy of the heart, edema, pain, epilepsy, nerve growth and cancer.

Further provided are methods of using epoxy fatty acids such as EpETrEs, EpETEs and EpDPEs and their synthetic mimics and sEH inhibitors to therapeutically target disease states with a known ER stress component such as Alzheimer's, Premature dementia, Amyotrophic Lateral Sclerosis (ALS), Parkinson's, prion diseases, depression, schizophrenia, diabetes, cancer and chemotherapy induced side effects.

Further provided are methods of inducing pain or activating ER stress in experimental animals or in vitro cell culture systems that closely mimics natural painful conditions and amenable to be used as models or for screening purposes, whether high throughput or not, to discover, test, validate or develop novel analgesic candidates.

Definitions

The terms "endoplasmic reticulum (ER) stress" refers to disruption of processes performed by the endoplasmic reticulum, including the synthesis, modification, folding and delivery of proteins to their proper target sites within the secretory pathway and the extracellular space. ER stress can be caused by, e.g., disruption of protein folding, aberrations in lipid metabolism, or disruption of cell wall biogenesis. See, e.g., Schröder and Kaufman, *Mutation Research* (2005) 569:29-63.

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3-membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is SEQ ID NO.:1, while the nucleic acid sequence encoding the human sEH is SEQ ID NO.:2. (The sequence set forth as SEQ ID NO.:2 is the coding portion of the sequence set forth in the Beetham et al. 1993 paper and in the NCBI Entrez Nucleotide Browser at accession number L05779, which include the 5' untranslated region and the 3' untranslated region.) The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

The term "neuroactive steroid" or "neurosteroids" interchangeably refer to steroids that rapidly alter neuronal excitability through interaction with neurotransmitter-gated ion channels, and which may also exert effects on gene expression via intracellular steroid hormone receptors. Neurosteroids have a wide range of applications from sedation to treatment of epilepsy and traumatic brain injury. Neurosteroids can act as allosteric modulators of neurotransmitter receptors, such as $GABA_A$, NMDA, and sigma receptors. Progesterone (PROG) is also a neurosteroid which activates progesterone receptors expressed in peripheral and central glial cells. Several synthetic neurosteroids have been used as sedatives for the purpose of general anaesthesia for carrying out surgical procedures. Exemplary sedating neurosteroids include without limitation alphaxolone, alphadone, hydroxydione and minaxolone.

By "physiological conditions" is meant an extracellular milieu having conditions (e.g., temperature, pH, and osmolarity) which allows for the sustenance or growth of a cell of interest.

The term "therapeutically effective amount" refers to that amount of the compound being administered sufficient to prevent or decrease the development of one or more of the symptoms of the disease, condition or disorder being treated (e.g., fibrosis and/or inflammation).

The terms "prophylactically effective amount" and "amount that is effective to prevent" refer to that amount of drug that will prevent or reduce the risk of occurrence of the biological or medical event that is sought to be prevented. In many instances, the prophylactically effective amount is the same as the therapeutically effective amount.

"Subtherapeutic dose" refers to a dose of a pharmacologically active agent(s), either as an administered dose of pharmacologically active agent, or actual level of pharmacologically active agent in a subject that functionally is insufficient to elicit the intended pharmacological effect in itself (e.g., to obtain analgesic, anti-inflammatory, and/or anti-fibrotic effects), or that quantitatively is less than the established therapeutic dose for that particular pharmacological agent (e.g., as published in a reference consulted by a person of skill, for example, doses for a pharmacological agent published in the Physicians' Desk Reference, 65th Ed., 2011, Thomson Healthcare or Brunton, et al., Goodman & Gilman's The Pharmacological Basis of Therapeutics, 12th edition, 2010, McGraw-Hill Professional). A "subtherapeutic dose" can be defined in relative terms (i.e., as a percentage amount (less than 100%) of the amount of pharmacologically active agent conventionally administered). For example, a subtherapeutic dose amount can be about 1% to about 75% of the amount of pharmacologically active agent conventionally administered. In some embodiments, a subtherapeutic dose can be about 75%, 50%, 30%, 25%, 20%, 10% or less, than the amount of pharmacologically active agent conventionally administered.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, University of the Sciences in Philadelphia, Eds., 21$^{st}$ Ed., Lippencott Williams & Wilkins (2005).

The terms "sustained release" and "extended release" are used in their conventional sense to refer to a drug formulation that provides for gradual release of a drug over an extended period of time, for example, 12 hours or more, and that preferably, although not necessarily, results in substantially steady-state blood levels of a drug over an extended time period.

As used herein, the term "delayed release" refers to a pharmaceutical preparation that passes through the stomach intact and dissolves in the small intestine.

As used herein, "synergy" or "synergistic" interchangeably refer to the combined effects of two active agents that are greater than their additive effects. Synergy can also be achieved by producing an efficacious effect with combined inefficacious doses of two active agents. The measure of synergy is independent of statistical significance.

The terms "systemic administration" and "systemically administered" refer to a method of administering agent (e.g., an agent that reduces or inhibits ER stress, an agent that increases epoxygenated fatty acids (e.g., an inhibitor of sEH, an EET, an epoxygenated fatty acid, and mixtures thereof), optionally with an anti-inflammatory agent and/or an analgesic agent) to a mammal so that the agent/cells is delivered to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administration" refers to the presence of both active agents/cells in the blood or body at the same time. Active agents that are co-administered can be delivered concurrently (i.e., at the same time) or sequentially.

The phrase "cause to be administered" refers to the actions taken by a medical professional (e.g., a physician), or a person controlling medical care of a subject, that control and/or permit the administration of the agent(s)/compound(s)/cell(s) at issue to the subject. Causing to be administered can involve diagnosis and/or determination of an appropriate therapeutic or prophylactic regimen, and/or prescribing particular agent(s)/compounds/cell(s) for a subject. Such prescribing can include, for example, drafting a prescription form, annotating a medical record, and the like.

The terms "patient," "subject" or "individual" interchangeably refers to a mammal including a human, a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster).

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

The terms "inhibiting," "reducing," "decreasing" refers to inhibiting the fibrosis and/or inflammation in a human or non-human mammalian subject by a measurable amount using any method known in the art. For example, inflammation is inhibited, reduced or decreased if an indicator of inflammation, e.g., swelling, blood levels of prostaglandin PGE2, is at least about 10%, 20%, 30%, 50%, 80%, or 100% reduced, e.g., in comparison to the same inflammatory indicator prior to administration of an agent that increases epoxygenated fatty acids (e.g., an inhibitor of sEH, an EET, an epoxygenated fatty acid, and mixtures thereof). In some embodiments, the fibrosis and/or inflammation is inhibited, reduced or decreased by at least about 1-fold, 2-fold, 3-fold, 4-fold, or more in comparison to the fibrosis and/or inflammation prior to administration of the agent that increases epoxygenated fatty acids (e.g., an inhibitor of sEH, an EET, an epoxygenated fatty acid, and mixtures thereof). Indicators of fibrosis and/or inflammation can also be qualitative.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than the listed active agents, e.g., an agent that increases epoxygenated fatty acids (e.g., an inhibitor of sEH, an EET, an epoxygenated fatty acid, and mixtures thereof) and/or an anti-inflammatory agent.

BRIEF DESCRIPTION OF THE DRAWINGS

FIGS. 1A-B illustrate that following streptozocin administration blood and CSF glucose levels rapidly rise and rats develop sensitivity to mechanical stimuli measured by electronic von Frey test (n=6 rats/group).

FIGS. 2A-H illustrate that high levels of ER stress occur in diabetic rats with neuropathic pain. Reversal of pain by sEH inhibitor, TPPU, within 30 min after administration correlates with suppression of ER stress markers. (A and B) Quantification of markers of ER stress from diabetic rats' paw skin by western blotting. Total skin lysates of healthy and type I diabetic (2 weeks post STZ) rats compared to TPPU (1 mg/kg, intraperitoneal) or vehicle treated animals, sampled 30 min after TPPU. Samples are immune-blotted for proteins specified next to each row using Tubulin as a loading control. Representative immunoblots of 3 rats from each group are shown. See Fig S1 for all 6 individual rats. Bar graph displays expression of each target normalized to Tubulin or their respective unphosphorylated forms as indicated. (C and D) Quantification of markers of ER stress from sciatic nerve bundle of same rats as above, by Western blotting. Total sciatic nerve lysate samples from same rats above were immuno-blotted for same targets as above using Tubulin as a loading control. See FIGS. 3 and 4 for all 6 individual rats. Bar graph displays expression of each target normalized to Tubulin or their respective unphosphorylated forms. (E) The chemical chaperone 4-phenyl butyric acid (4-PBA) reduce allodynia in a dose and time dependent manner (10-100 mg/kg). Pain related behavior is measured using von Frey assay and withdrawal thresholds are reported as "% change from pre-diabetic baseline" (F) Administration of 4-PBA (40 mg/kg) to healthy rats does not result in change of acute mechanical withdrawal threshold. (G) TPPU, a potent inhibitor of sEH, reduce allodynia in a dose and time dependent manner (0.01-1 mg/kg). (H) Dose-response data for each compound at 60 min post administration are plotted as % change produced and effective dose values are calculated using SigmaPlot software suite (n=6/group in all panels). Data are presented as mean±SEM in all subsequent figures throughout the text.

FIGS. 5A-B illustrate that expression of sEH and markers of autophagy are upregulated in the skin and sciatic nerve of diabetic rats. (A) Expression of sEH and markers of autophagy are upregulated in the skin of diabetic rats (B) In parallel to the increases in the diabetic skin, expression of sEH and markers of autophagy are also upregulated in the sciatic nerve of diabetic rats.

FIGS. 6A-C illustrate that a chemical chaperone and an sEH inhibitor synergistically block pain-related behavior in type I diabetic rats. (A) An ineffective dose of 4-PBA (10 mg/kg) is displayed against the two combination doses over a 6 h time period. (B) The CompuSyn software was used to construct an isobologram of the interaction. ED50 values calculated for each drug are plotted on x and y-axis respectively. The ED50 of the combination is lower than what would be expected if the two compounds did not interact. (C) Combination index (CI) is reported as the key parameter of the synergistic interaction. Drug reduction index for each compound demonstrates fold reduction in dose to attain similar efficacy and is calculated by the CompuSyn algorithm (n=6/group in all panels).

FIGS. 7A-F illustrate that ER stress inducer tunicamycin (Tm) is rapid, intense and selective in generating pain behavior. (A) Tm is administered into the midsection of one hind paw in a volume of 10 μL (20 μg). Mechanical withdrawal of ipsi- and contralateral paws are then monitored over a period of 6 h until the ipsilateral paw measurements returned to baseline values. The withdrawal data are presented as gram force required for inducing a withdrawal reflex response. (B) Decreasing doses of Tm generated less intense allodynia which subsided faster than the highest dose. (C) In contrast to the decrease in mechanical withdrawal threshold, Tm induced a notable increase in thermal withdrawal threshold as measured by the modified Hargreaves' test. As in the case of allodynia, this hypoalgesia is restricted to the ipsilateral side suggesting peripherally maintained pain. (D) Intraplantar Tm induced pain is reversible with sEH inhibitor (1h prior to Tm, i.p. administration) in a dose dependent manner. (E) Expectedly this pain is reversible with chemical chaperone 4-PBA. The basis for the increase above the baseline threshold in this group is not investigated. (F) However, the pre-administration of a high dose of selective cox-2 inhibitor, celecoxib (30 mg/kg, 1 h prior, i.p. route) resulted in marginal efficacy. Overall these data argue for a neuropathic characteristics of the Tm model (n=6/group in all panels).

FIGS. 8A-D illustrate that ER stress inducer Tm leads to activation of full range of ER stress responses within minutes. These include increases in markers of apoptosis and autophagy all of which are reversed by inhibition of sEH. Rats are given intraplantar Tm (20 μg) on the ipsilateral side and vehicle on the contralateral side with or without TPPU (1 h prior to Tm, 10 mg/kg, i.p. route). Tissue samples are obtained 30 min post Tm, under deep anesthesia. (A and B) Quantification of markers of ER stress from Tm (ipsi-) and vehicle (contra-) administered paw skin by western blotting. Total skin lysates are immune-blotted for targets specified next to each row using Tubulin as a loading control. Representative immunoblots of 3 rats from each group are shown. Bar graph displays expression of each target normalized to Tubulin or their respective unphosphorylated forms as indicated (n=6 rats/group). (C and D) Quantification of markers of ER stress in the sciatic nerve bundle of same rats as above by western blotting. Total sciatic nerve lysates are immune-blotted for targets specified next to each row using Tubulin as a loading control. Representative immunoblots of 3 rats from each group are shown. Bar graph displays expression of each target normalized to Tubulin or their respective unphosphorylated forms as indicated (n=6 rats/group in all panels).

FIGS. 9A-C illustrate that mechanistically different ER stress inducer dimethylcelecoxib (DMCx) generates a rapid and intense but sEHI and cox-2 inhibitor reversible pain phenotype. (A) DMCx is administered into the midsection of one hind paw in a volume of 10 μL (20 μg). Mechanical withdrawal of ipsi- and contralateral paws are then monitored over a period of 4 h. The withdrawal data are presented as gram force required for inducing a withdrawal reflex response. (B) Intraplantar DMCx induced pain is reversible with sEH inhibitor (1 h prior to Tm, i.p. administration) in a dose dependent manner. (C) In contrast to Tm induced pain, DMCx induced pain was partially blocked by pre-administration of the selective cox-2 inhibitor celecoxib (30 mg/kg, 1 h prior, i.p. route). Overall, these data argue for a more inflammatory phenotype of the DMCx model (n=6/group in all panels).

Figure 3A:
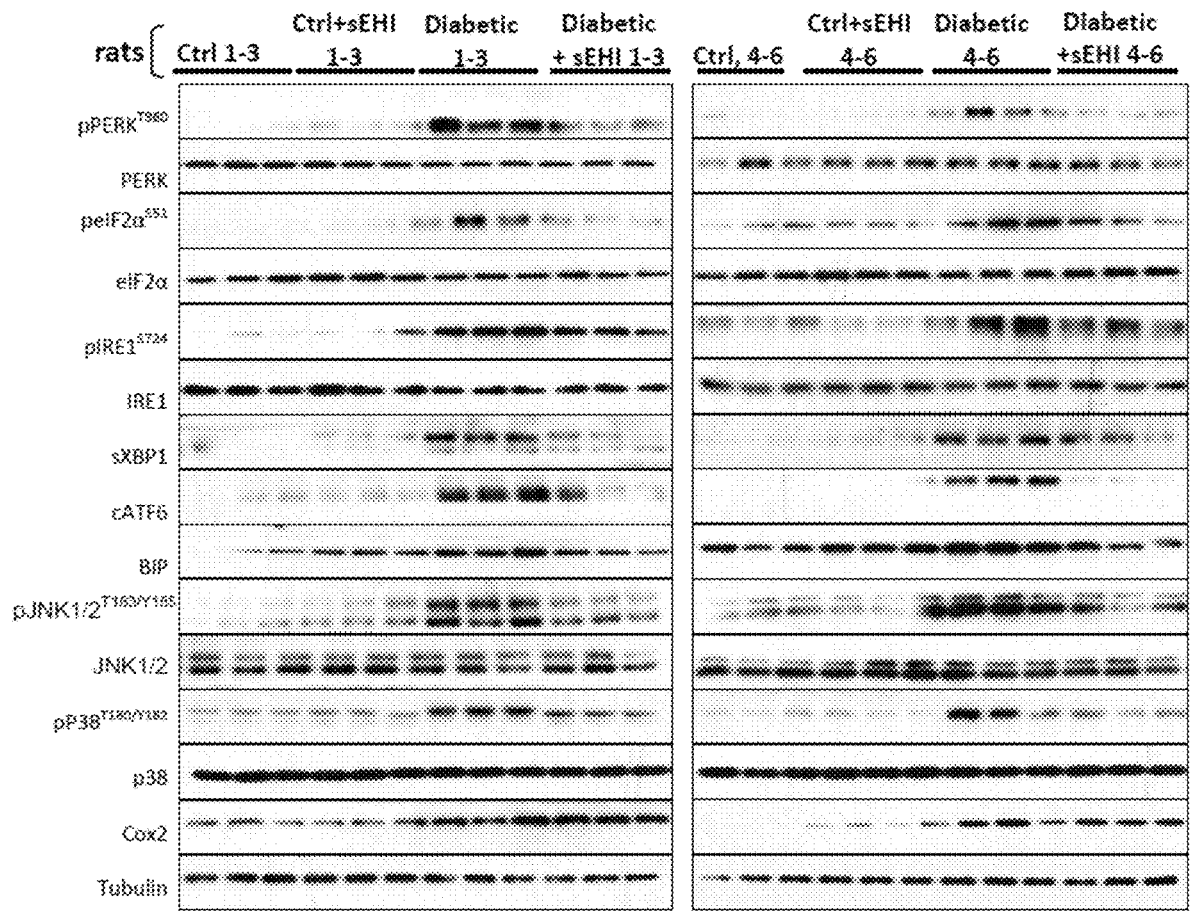
FIGS. 3A-B provide Western blots of paw skin samples all animals from FIG. 2A and the bar graph of levels of mRNA expression for the key downstream targets of ER stress sensors. Expression of BiP, sXPB1 and ATF4 mRNA are significantly increased in diabetic rat paw skin and reduced by inhibition of sEH.
Figure 3B:
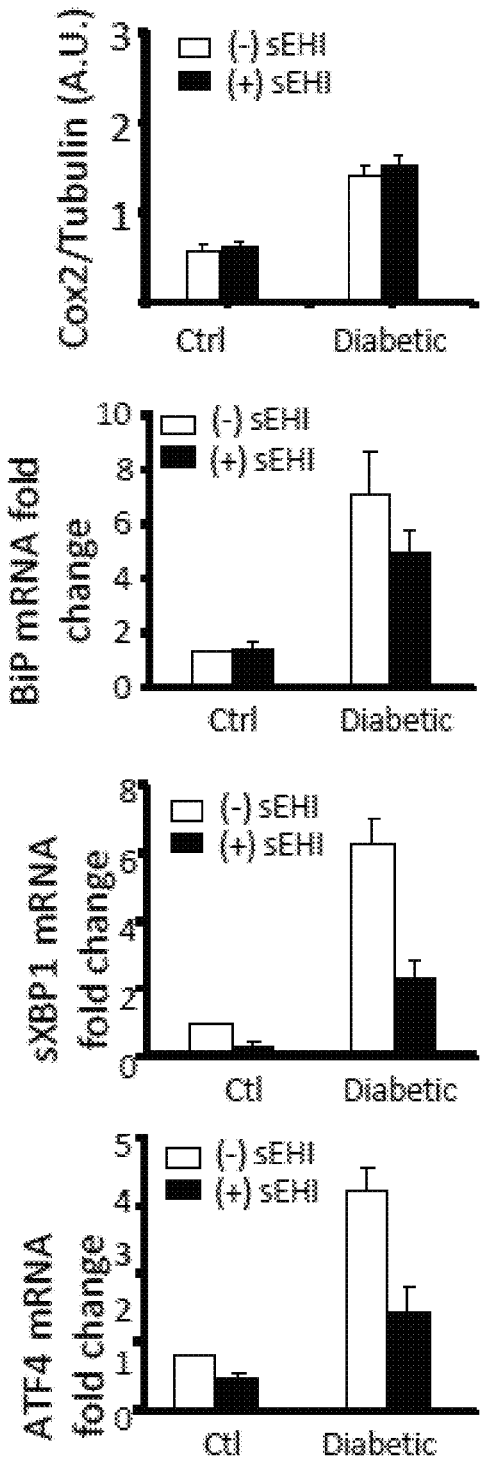
Figure 4A:
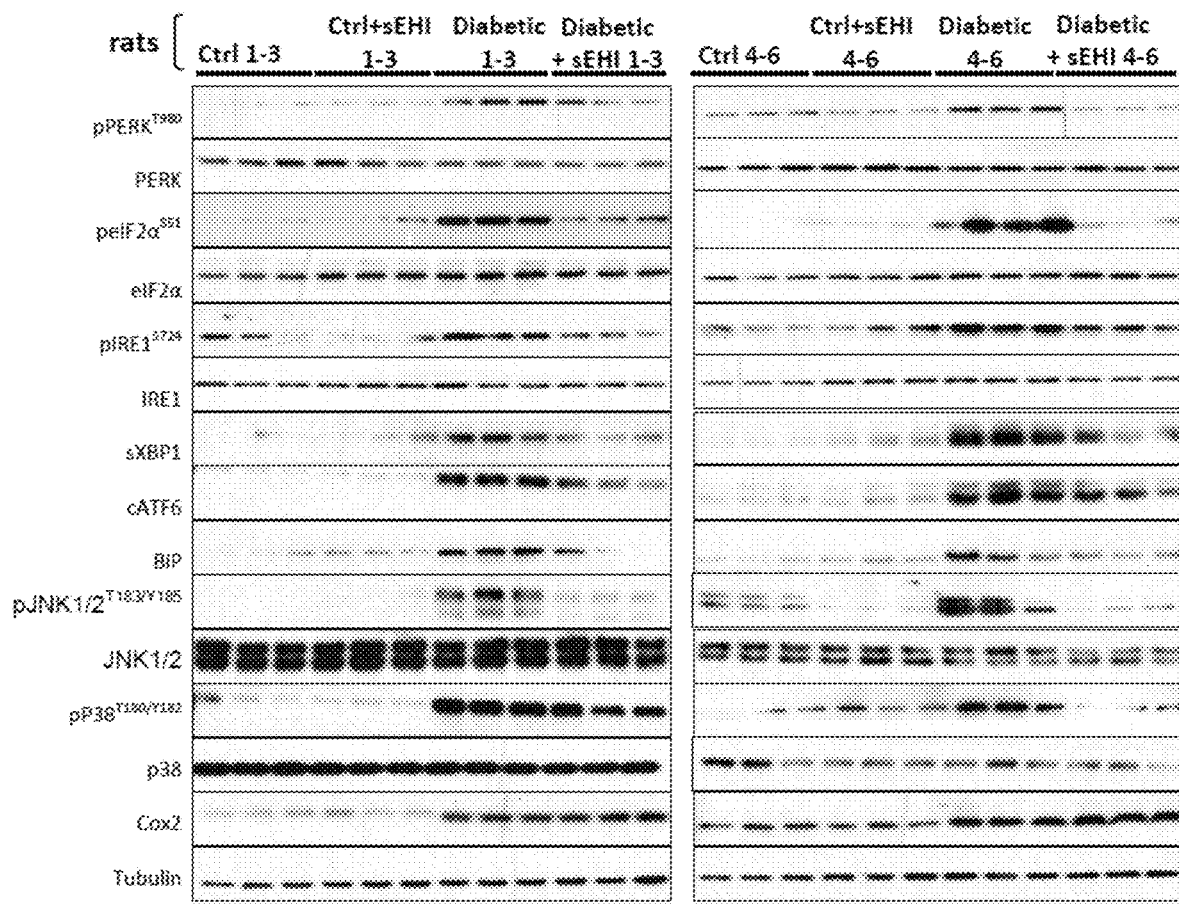
FIGS. 4A-B provide Western blots of sciatic nerve samples all animals from FIG. 2B and the bar graph of levels of mRNA expression for the key downstream targets of ER stress sensors. Expression of BiP, sXPB1 and ATF4 mRNA are significantly increased in diabetic rat sciatic nerve bundle and reduced by inhibition of sEH.
Figure 4B:
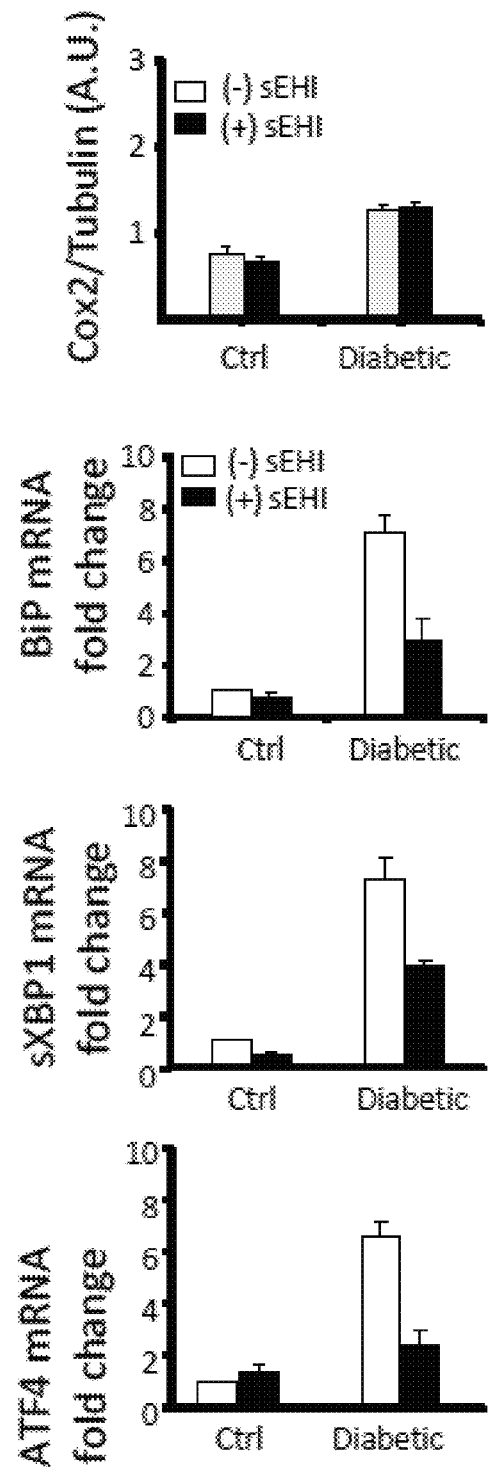
Figure 10A:
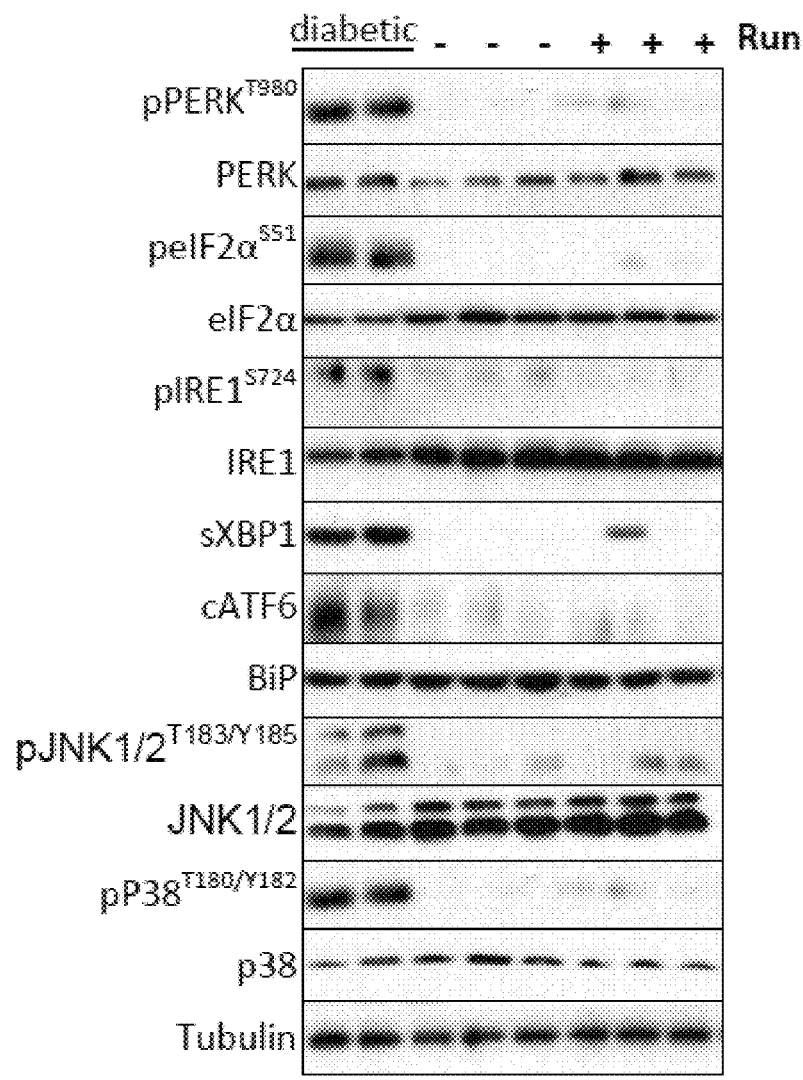
Figure 10B:
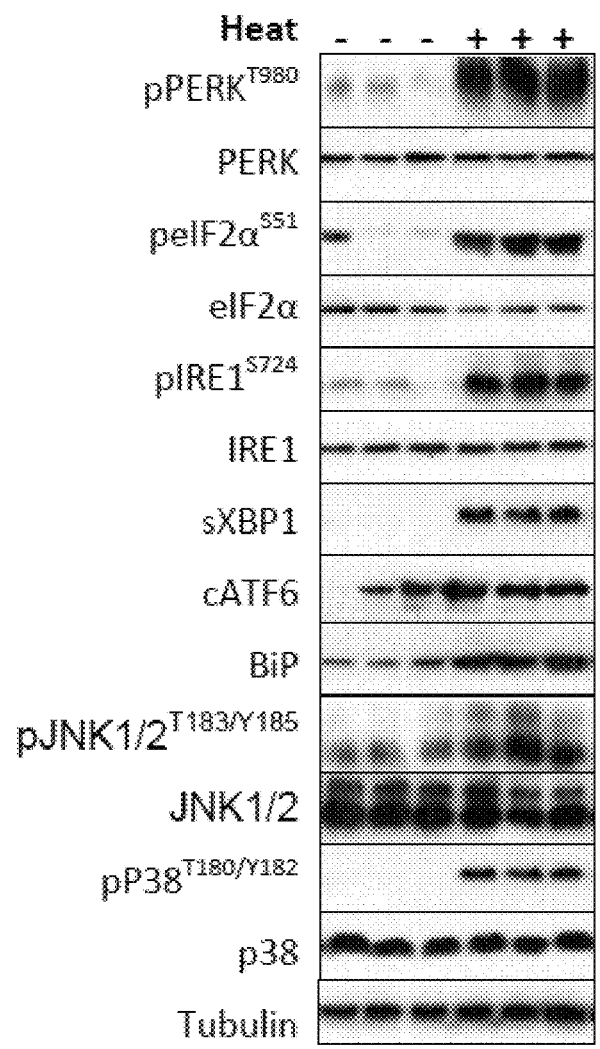

FIGS. 10A-B illustrate that ER stress markers in the sciatic nerve are not increased with motor activation but are up-regulated following suprathreshold heat stimuli under deep general anesthesia. Total sciatic nerve lysates are examined by western blotting, same as shown in FIGS. 2 and 8. (A) Rats are allowed to run on a rotarod wheel for 600 sec and euthanized under isoflurane anesthesia by decapitation. Sciatic nerve samples are then excised and frozen in less than 60 sec. Control rats rest in home cages prior to sampling (n=3/group). Two randomly selected diabetic rat samples are used as positive controls (lanes 1 and 2). Overall brief physical activity or surgical procedures do not lead to significant phosphorylation of ER stress marker proteins. (B) Under deep anesthesia (5% Isoflurane, 5 LPM $O_2$), one hind paw is contacted to 53° C. hotplate for 10 sec. Sciatic nerve samples are taken immediately after stimulation, contralateral sciatic, not exposed to heat used as control (n=3/group). Significant increase in levels of ER stress markers suggest neuronal selective detection of these markers which are maintained even with deep anesthesia.

DETAILED DESCRIPTION

1. Introduction

Despite intensive effort and resulting gains in understanding the mechanisms of neuropathic pain, limited success in therapeutic approaches have been attained. A recent, non-channel, non-neurotransmitter therapeutic target for pain is the enzyme soluble epoxide hydrolase (sEH). The sEH degrades natural analgesic lipid mediators, epoxy fatty acids, therefore its inhibition stabilizes these bioactive mediators. Here we demonstrate the effects of sEH inhibition on diabetes induced neuropathic pain and define a previously unknown mechanism, regulation of pain by ER stress. The increase in markers of ER stress is quantified in the peripheral nervous system (PNS) of Type I diabetic rats. The diabetic pain and markers of ER stress are reversible by a chemical chaperone and by increasing lipid epoxides. Chemical inducers of ER stress administered into the hind paw invariably lead to increased pain that is reversible by chemical chaperone and an inhibitor of sEH. The rapid occurrence of pain behavior with inducers, equally rapid reversal by blockers and natural incidence of ER stress in diabetic PNS demonstrate the major role of the ER stress pathways in regulating the excitability of the nociceptive system. The understanding the role of ER stress in generation and maintenance of pain opens routes to exploit this system for therapeutic purposes.

Provided are methods and compositions of blocking pain employing synergistic combinations of at least one soluble epoxide hydrolase (sEH) inhibitor and at least on inhibitor of endoplasmic reticulum (ER) stress. The methods and compositions find use in targeting diseases with known endoplasmic reticulum stress component. Surprisingly, the methods mitigate, alleviate, reduce, inhibit or block symptoms associated with pain and other disease conditions associated with ER stress within hours (e.g., within 24, 12, 6, 3, 2, 1 hours or less) or minutes (e.g., effectively immediate relief).

The present methods and compositions are based, in part, on the discovery of a root cause for nerve damage-induced pain. This discovery also applies to inflammatory pain, however the previously unknown biological pathway is an underlying and causative factor in multiple types of pharmacoresistant pain syndromes. This pathway also seems to have a major role in the pathological and long term maintenance of chronic pain even after the initial injury is resolved or eliminated. By preventing the activation of the cascade of events that lead to cellular stress we were able to block inflammatory and neuropathic pain without affecting other physiological responses such as motor function. By activating the cascade of events that lead to cellular stress using multiple approaches we were able to induce pain that closely mimics neuropathy mediated pain. We further demonstrate the feasibility of this approach by using two distinct classes of blockers of a pathway of ER stress, e.g., inhibitors of sEH and inhibitors of ER stress. Combined and concurrent use of distinct classes of blockers of ER stress is highly synergistic in reducing pain, demonstrating the importance of targeting ER stress. Furthermore, our findings demonstrate that agents that target the ER stress pathway at any level are highly effective analgesics without the use-limiting side effects of current analgesics. By logical extension, we identify agents that synergize with sEH inhibitors to treat disease conditions caused at least in part by endoplasmic reticulum stress and therefore which are highly effective therapeutics in treating pain, particularly neuropathic pain. Our work identifies agents that create neuropathic pain (e.g., for use in animal models of pain), agents that block neuropathic pain, and agents that synergize to block neuropathic pain.

2. Subjects Who May Benefit—Conditions Subject to Treatment

The methods and compositions find use for preventing, reducing, ameliorating, mitigating, inhibiting and/or reversing one or more symptoms associated with or caused at least in part by a disease or disease condition caused at least in part by endoplasmic reticulum (ER) stress. Illustrative diseases and disease conditions subject to treatment by the present methods and compositions include without limitation, e.g., inflammatory disease, cardiovascular disease, pulmonary disease, renal disease, diabetes, neurological disease, hypertension, pulmonary edema, pulmonary hypertension, cystic fibrosis, cardiomyopathy, hypertrophy of the heart, edema, pain, epilepsy, neuroma, cancer, Alzheimer's disease, dementia, Amyotrophic Lateral Sclerosis (ALS), Parkinson's disease, prion diseases, depression, schizophrenia, and chemotherapy induced side effects. In varying embodiments, the subject may by symptomatic or asymptomatic for the disease or disease condition.

a. Pain

In varying embodiments, the disease or disease condition is pain, including inflammatory pain and neuropathic pain. In varying embodiments co-administration of an agent that increases the production and/or level of epoxygenated fatty acids and an inhibitor of endoplasmic reticulum stress finds use in treating, i.e., reducing, relieving, ameliorating, mitigating, preventing, inhibiting and/or reversing neuropathic pain in a subject or patient in need thereof. The patient may be subject to suffering neuropathic pain chronically or intermittently. The patient may or may not be exhibiting or experiencing symptoms of neuropathic pain at the nine of treatment. The neuropathic pain may be centrally or peripherally mediated.

Neuropathic pain results from a pathology in the nervous system. Notable features of neuropathic pain include (1) widespread pain not otherwise explainable; (2) evidence of sensory deficit; (3) burning pain; (4) pain to light stroking of the skin (allodynia); and (5) enhanced stimulus-dependent pain (hyperalgesia) and (6) attacks of pain without seeming provocation (stimulus-independent pain). Mechanisms of neuropathic pain are described, for example, in Zhuo, Molecular Pain (2007) 3:14; Campbell and Meyer, Neuron (2006) 52(1):77-92; Dworkin, et al., Arch Neurol (2003) 60:1524-34.

Neuropathic pain originates from a lesion of the nervous system (e.g., nerve damage). Any of a number of disease conditions or injuries can be the underlying cause of neuropathic pain. For example, the patient may be suffering from a metabolic disease (e.g., diabetic neuropathy), an autoimmune disease (e.g., multiple sclerosis), a viral infection (e.g. shingles and sequelae, postherpetic neuralgia), vascular disease (e.g. stroke), trauma and/or cancer. See, e.g. Campbell and Meyer, Neuron (2006) 52(1):77-92; Dworkin et al., Arch Neurol (2003) 60; 1524-34. In varying embodiments, the neuropathic pain is due to nerve damage arising from one or more of trauma, ischemia or hemorrhage, inflammation, neurotoxicity, neurodegeneration, paraneoplastic, metabolic disease, vitamin deficiency, or cancer. In varying embodiments, the neuropathic pain is can be classified as toxic (e.g., arising from or secondary to chemoradiation or exposure to chemicals that cause nerve damage), metabolic (e.g., arising from or secondary to diabetes or nutritional deficiency, alcoholism), traumatic (e.g., arising from or secondary to phantom limb syndromes and/or complex regional pain syndromes (CRPS)), compressive (e.g., arising from or secondary to nerve entrapment and/or excessive external pressure on nerve axons which can cause ischemic or distortional (stretching) changes, or Wallerian degeneration of the axon with resultant muscle atrophy, autoimmune (e.g., arising from or secondary to autoimmune disease (e.g., Guillain-Barre Syndrome), chronic inflammatory demyelinating polyneuropathy (CIDP) and/or vasculitic neuropathy), infectious (e.g., arising from or secondary to an infectious disease, e.g., a viral infection such as Herpes Simplex Virus (HSV), Varicella Zoster Virus, Human Immunodeficiency Virus (HIV), a spirochete infection such as Lyme Disease, a trypanosome infection such as Chagas' Disease, a mycobacterium infection such as leprosy, and congenital/hereditary (e.g., arising from or secondary to Fabry's Disease, Charcot-Marie-Tooth Disease (burning pain in extremities), amyloidosis).

In some embodiments, the patient is suffering from peripheral neuropathic pain, for example, as a result of a disease condition including acute and chronic inflammatory demyelinating polyradiculoneuropathy; alcoholic polyneuropathy; chemotherapy-induced polyneuropathy; complex regional pain syndrome; entrapment neuropathies (e.g., carpal tunnel syndrome); HIV sensory neuropathy; iatrogenic neuralgias (e.g., postmastectomy pain or postthoracotomy pain); idiopathic sensor neuropathy; nerve compression or infiltration by tumor; nutritional deficiency-related neuropathies; painful diabetic neuropathy, phantom limb pain; postherpetic neuralgia; postradiation plexopathy; radiculopathy (cervical, thoracic, or lumbosacral); toxic exposure-related neuropathies; tic douloureux (trigeminal neuralgia); and/or posttraumatic neuralgias.

In some embodiments, the patient is suffering from central neuropathic pain, for example, as a result of a disease condition including compressive myelopathy from spinal stenosis; HIV myelopathy, multiple sclerosis-related pain; Parkinson disease-related pain; postischemic myelopathy; postradiation myelopathy; poststroke pain; posttraumatic spinal cord injury pain; and/or syringomyelia.

The identification and definition of different types of neuropathic pain have been classified by the International Association for the Study of Pain (IASP) and International Classification of Diseases (ICD). See, e.g., Finnerup, *Eur J Pain* 17 (2013) 953-956 and references cited therein. In varying embodiments, the subject experiences one or more symptoms including paresthesia (an abnormal sensation, whether spontaneous or evoked), dysesthesia (an unpleasant sensation, whether spontaneous or evoked), hypoesthesia (decreased sensitivity to stimulation (tactile or thermal; both are frequent), hyperesthesia (increased sensitivity to stimulation (tactile or thermal)), hypoalgesia (diminished pain response to a normally painful stimulus), hyperalgesia (an increased response to a stimulus that is normally painful), allodynia (pain due to a stimulus that does not normally activate the nociceptive system).

a. Cardiac Hypertrophy

In varying embodiments, the subject has cardiomyopathy or cardiac arrhythmia. For example, the subject may have hypertrophic cardiomyopathy, e.g., due to valvular heart disease, familial hypertrophic cardiomyopathy, dilated cardiomyopathy, myocardial infarction, or secondary to administration of an anti-cancer drug or exposure to a toxic agent. Valvular heart disease can arise from any etiology, including, e.g., secondary to rheumatic fever, myxomatous degeneration of the valve, or papillary muscle dysfunction. In varying embodiments, the subject has cardiac arrhythmia, e.g., due to atrial fibrillation, ventricular fibrillation, or ventricular tachycardia.

Cardiomyocytes are terminally differentiated cells. In response to various extracellular stimuli, cardiomyocytes grow in a hypertrophic manner, an event that is characterized by enlargement of individual cell size, an increase in the content of contractile proteins such as myosin heavy chain, and expression of embryonic genes such as atrial natriuretic factor (ANF). (Chien et al., Faseb J.; 5:3037-46 (1991); Chien, Cardiologia.; 37:95-103 (1992); Chien, J Clin Invest.; 105:1339-42 (2000)) The collective result is cardiac hypertrophy, which is an adaptive and compensatory response in nature. The initial or compensated stage of hypertrophy normalizes wall stress per unit of myocardium and is thus a basic mechanism for maintaining normal chamber function. (Grossman et al, J Clin Invest.; 56:56-64 (1975)) However, this process is a double-edged sword: sustained cardiac hypertrophy will eventually lead to overt heart failure.

In most instances, heart failure is the final consequence of many underlying disease etiologies such as long-standing hypertension, coronary heart disease, valvular insufficiency, arrhythmia, viral myocarditis, and mutations in sarcomere-encoding genes. A compensatory enlargement of the myocardium, or hypertrophy, typically accompanies many of these predisposing insults and is a leading predictor for the development of more serious and life-threatening disease. Decompensated hypertrophy occurs if increased cardiac mass fails to normalize wall stress and the contractile function is not sufficient to maintain normal pump function. This is associated with clinical and pathological features of congestion.

Cardiac hypertrophy is characterized by an increase in heart-to-body weight ratio and an increase in the size of the individual cardiac myocytes, enhanced protein synthesis, and heightened organization of the sarcomere. Classically, two different hypertrophic phenotypes can be distinguished: (1) concentric hypertrophy due to pressure overload, which is characterized by parallel addition of sarcomeres and lateral growth of individual cardiomyocytes, and (2) eccentric hypertrophy due to volume overload or prior infarction, characterized by addition of sarcomeres in series and longitudinal cell growth. (Dorn et al., Circ Res.; 92:1171-5 (2003)). At the molecular level, these changes in cellular phenotype are accompanied by reinduction of the so-called fetal gene program, because patterns of gene expression mimic those seen during embryonic development. (Chien et al., Faseb J; 5:3037-46 (1991); Chien K R, Cardiologia.; 37:95-103 (1992)).

Hypertrophic transformation of the heart can be divided into three stages: (1) developing hypertrophy, in which load exceeds output, (2) compensatory hypertrophy, in which the workload/mass ratio is normalized and resting cardiac output is maintained, and (3) overt heart failure, with ventricular dilation and progressive declines in cardiac output despite continuous activation of the hypertrophic program. (Meerson F Z, Cor Vasa.; 3:161-77 (1961)). The late-phase "remodeling" process that leads to failure is associated with functional perturbations of cellular $Ca^{2+}$ homeostasis (Bers D M, Nature.; 415:198-205 (2002); Bers D M, Circ Res.; 90:14-7 (2002)) and ionic currents, (Ahmmed et al., Circ Res.; 86(5):558-70 (2000); Kaab et al., Circ Res.; 78:262-273 (1996); Kaab et al., Circulation.; 98:1383-93 (1998)) which contribute to an adverse prognosis by predisposing to ventricular dysfunction and malignant arrhythmia. Significant morphological changes include increased rates of apoptosis, (Haunstetter A and Izumo S, Circ Res.; 86:371-6 (2000)) fibrosis, and chamber dilation.

The dichotomy between adaptive and maladaptive hypertrophy has been appreciated for some time, and the mechanisms that determine how long-standing hypertrophy ultimately progresses to overt heart failure are in the process of being elucidated. One biochemical hallmark of left ventricular hypertrophy induced by pressure overload is a shift in myosin isoform from .alpha.-to.beta.-myosin heavy chains. (Delcayre C and Swynghedauw B, Pflugers Arch.; 355:39-47 (1975)). This alteration in myosin isoform expression result from transcriptionally mediated alteration in gene expression. (Boehler et al., J Biol. Chem.; 267:12979-12985 (1992)). Various lines of evidence suggest a decrease in the expression of the sarcoplasmic reticulum $Ca^{2-}$-cycling protein, $Ca^{2+}$ ATPase during the development of heart failure in several animal models, including humans with end-stage congestive heart failure, even though no changes can be detected during the compensated hypertrophied stage. (Kiss et al., Circ Res.; 77:759-764 (1995); Feldman et al., Circulation.; 75:331-9 (1987); Arai et al, Circ Res.; 72:463-469 (1993)). These changes are associated with a decrease in sarcoplasmic reticulum $Ca^{2+}$ transport. In addition, there are alterations in the level of phospholamban, sarcoplasmic reticulum $Ca^{2+}$-release channels and in $Ca^{2+}$ cycling proteins in the myofibrils and sarcolemma in different animal models with heart failure. (de la Bastie et al., Circ Res.; 66:554-564 (1990); Mercadier et al., J Clin Invest.; 85:305-309 (1990)). These studies suggest that critical components of the $Ca^{2+}$ cycling system may be responsible, in part, for the transitions between compensated pressure-overload hypertrophy and congestive heart failure.

Hypertrophy that occurs as a consequence of pressure overload is termed "compensatory" on the premise that it facilitates ejection performance by normalizing systolic wall stress. Recent experimental results, however, call into question the necessity of normalization of wall stress that results from hypertrophic growth of the heart. These findings, largely from studies in genetically engineered mice, raise the prospect of modulating hypertrophic growth of the myocardium to afford clinical benefit without provoking hemodynamic compromise. (Frey et al., supra, Dorn and Molkentin, supra; Frey et al., Circulation.; 109:1580-9 (2004)).

It is generally accepted that cardiac hypertrophy can be adaptive in some situations, for example, in athletes. However, it is less clear if a hypertrophic response to pathological situations, such as valvular heart disease, chronic arterial hypertension or a myocardial infarction, is initially a compensatory response and later becomes maladaptive or if this type of myocardial growth is detrimental from the outset.

It has been demonstrated that these different types of cardiac hypertrophy differ both at the morphological as well as the molecular level. Exercise-induced cardiac hypertrophy is generally not accompanied by an accumulation of collagen in the myocardium and usually does not exceed a modest increase in ventricular wall thickness. In addition, there are significantly differences in the expression levels for several hypertrophic genes, such as BNP or ET-1. Further, the isoform expression of α-/β-MHCs is regulated in opposite directions in exercise versus pressure overload-induced cardiac hypertrophy. However, some hypertrophic pathways, such as calcineurin-dependent signaling, appear to be activated in both pathological and physiological exercise-induced hypertrophy, as demonstrated by the finding that the calcineurin inhibitor can attenuate both phenotypes. Taken together, these data indicate that exercise-associated (physiologic) versus pathologic hypertrophy differ at the molecular level, but this does not exclude the possibility that certain pathways may be involved in all phenotypes of cardiac hypertrophy.

Since adult cardiomyocytes are terminally differentiated cells, many of the same intracellular signaling pathways that regulate proliferation in cancer cells or immune cells instead regulate hypertrophic growth of cardiomyocytes. The hypertrophic growth can be initiated by endocrine, paracrine, and autocrine factors that stimulate a wide array of membrane-bound receptors. Their activation results in the triggering of multiple cytoplasmic signal transduction cascades, which ultimately affects nuclear factors and the regulation of gene expression. It has previously been documented that no single intracellular transduction cascade regulates cardiomyocyte hypertrophy in isolation, but instead each pathway operates as an integrated component between interdependent and cross-talking networks. Therefore, blockade of specific intracellular signaling pathways in the heart can dramatically affect the entire hypertrophic response and effectively decrease cardiac hypertrophy. Furthermore, specific activation of a number of discrete signal transduction pathways may be sufficient to activate the entire hypertrophic response through effects on other cross-talking signaling networks.

b. Valvular Heart Disease

The heart has four valves: the mitral valve (the only valve with two flaps), the tricuspid, with three differently sized flaps, the aortic valve, which opens to allow blood from the heart into the aorta, and the pulmonary valve. A number of disorders affecting the valves can result in increased pressure in the chambers of the heart, which in turn can result in cardiac hypertrophy. These conditions include mitral valve stenosis, mitral valve insufficiency, aortic valve insufficiency, aortic valve stenosis, and tricuspid valve insufficiency. Several of these conditions occur in persons who had undiagnosed or incompletely treated rheumatic fever as a child. Rheumatic fever occurs most often in children who have a streptococcal throat infection ("strep throat"), and can result in mitral stenosis, tricuspid stenosis, aortic insufficiency, aortic stenosis, multivalvular involvement or, less commonly, pulmonic stenosis. Unlike stenosis of blood vessels, which is typically caused by a build-up of lipids and cells on the interior of the vessel lumen, stenosis of heart valves is typically due to fusing of the flaps, to a build-up of calcium on the flap, causing it to harden, to a congenital deformity, a weakening of valve tissue ("myxomatous degeneration"), or use of certain medicines, such as fenfluramine and dexfenfluramine.

3. Agents that Reduce and/or Inhibit Endoplasmic Reticulum (ER) Stress

Methods and compositions described herein involve the co-formulation and/or co-administration of an agent that increases the production and/or level of epoxygenated fatty acids and an inhibitor of endoplasmic reticulum (ER) stress. Any agent known in the art to reduce and/or inhibit levels of ER stress can be used. Illustrative agents that reduce and/or inhibit ER stress include without limitation, e.g., 4-phenyl butyric acid ("PBA"), butyrate, 3-phenylpropionic acid (3-PPA), 5-phenylvaleric acid (5-PVA), 6-phenylhexanoic acid (6-PHA), tauroursodeoxycholic acid, trehalose, deuterated water, docosahexaenoic acid ("DHA"), eicosapentaenoic acid ("EPA"), vitamin C, arabitol, mannose, glycerol, betaine, sarcosine, trimethylamine-N oxide and DMSO.

4. Agents that Increase the Production and/or Level of Epoxygenated Fatty Acids

Agents that increase epoxygenated fatty acids include epoxygenated fatty acids (e.g., including EETs), and inhibitors of soluble epoxide hydrolase (sEH).

a. Inhibitors of Soluble Epoxide Hydrolase (sEH)

Scores of sEH inhibitors are known, of a variety of chemical structures. Derivatives in which the urea, carbamate or amide pharmacophore are particularly useful as sEH inhibitors. As used herein, "pharmacophore" refers to the section of the structure of a ligand that binds to the sEH. In various embodiments, the urea, carbamate or amide pharmacophore is covalently bound to both an adamantane and to a 12 carbon chain dodecane. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N, N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-adamantyl ureas have been tested and have about the same high activity as an inhibitor of sEH. Thus, isomers of adamantyl dodecyl urea are preferred inhibitors. It is further expected that N, N'-dodecyl-cyclohexyl urea (DCU), and other inhibitors of sEH, and particularly dodecanoic acid ester derivatives of urea, are suitable for use in the methods. Preferred inhibitors include:

12-(3-Adamantan-1-yl-ureido)dodecanoic acid (AUDA),

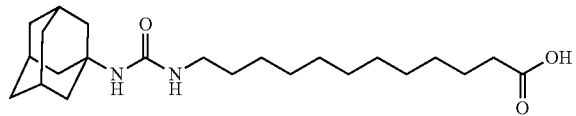 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE),

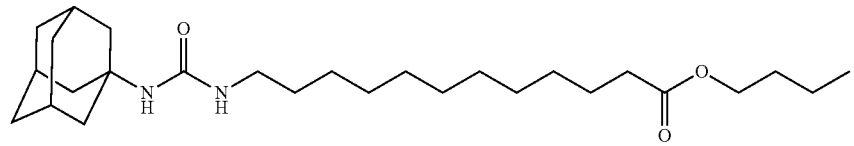 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (compound 950, also referred to herein as "AEPU"), and

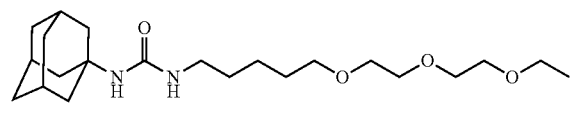 [SMILES: CCOCCOCCOCCCCCNC(=O)NC12CC3CC(CC(C3)C1)C2]

Another preferred group of inhibitors are piperidines. The following Tables sets forth some exemplar inhibitors of sEH and their ability to inhibit sEH activity of the human enzyme and sEH from equine, ovine, porcine, feline and canine, expressed as the amount needed to reduce the activity of the enzyme by 50% (expressed as "$IC_{50}$").

TABLE 1

IC$_{50}$ values for selected alkylpiperidine-based sEH inhibitors against human sEH

| R: | Compound (n=0) | IC$_{50}$ (μM)[a] | Compound (n=1) | IC$_{50}$ (μM)[a] |
|---|---|---|---|---|
| H | I | 0.30 | II | 4.2 |
| ethyl | 3a | 3.8 | 4a | 3.9 |
| propyl | 3b | 0.81 | 4b | 2.6 |
| butyl | 3c | 1.2 | 4c | 0.61 |
| benzyl | 3d | 0.01 | 4d | 0.11 |

[a] As determined via a kinetic fluorescent assay.

TABLE 2 sEH inhibitors

| Structure | Name | sEHi # |
|---|---|---|
| 3-(4-chlorophenyl)-1-(3,4-dichlorphenyl)urea | 3-(4-chlorophenyl)-1-(3,4-dichlorphenyl)urea or 3,4,4'-trichlorocarbanilide | 295 (TCC) |
| adamantyl-urea-dodecanoic acid | 12-(3-adamantan-1-yl-ureido) dodecanoic acid | 700 (AUDA) |
| adamantyl-urea-PEG | 1-adamantanyl-3-{5-[2-(2-ethoxyethoxy)ethoxy]pentyl}urea | 950 (AEPU) |
| adamantyl-urea-acetylpiperidine | 1-(1-acetypiperidin-4-yl)-3-adamantanylurea | 1153 (APAU) |

TABLE 2-continued sEH inhibitors

| Structure | Name | sEHi # |
|---|---|---|
| | trans-4-[4-(3-Adamantan-1-yl-ureido)-cyclohexyloxy]-benzoic acid | 1471 (tAUCB) |
| 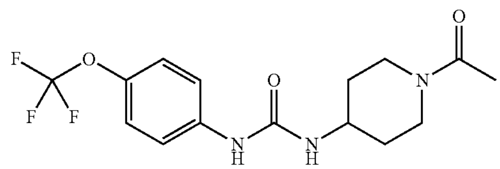 [SMILES: CC(=O)N1CCC(NC(=O)Nc2ccc(OC(F)(F)F)cc2)CC1] | 1-trifluoromethoxyphenyl-3-(1-acetylpiperidin-4-yl) urea | 1555 (TPAU) |
| 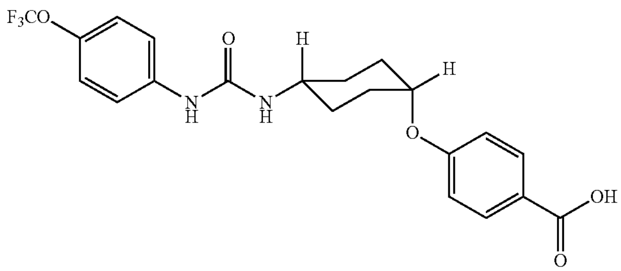 [SMILES: O=C(Nc1ccc(OC(F)(F)F)cc1)NC1CCC(Oc2ccc(C(=O)O)cc2)CC1] | cis-4-[4-(3-Adamantan-1-yl-ureido)-cyclohexyloxy]-benzoic acid | 1686 (cAUCB) |
| 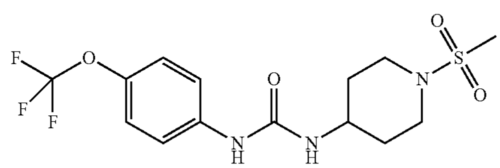 [SMILES: CS(=O)(=O)N1CCC(NC(=O)Nc2ccc(OC(F)(F)F)cc2)CC1] | 1-(1-methylsulfonyl-piperidin-4-yl)-3-(4-trifluoromethoxy-phenyl)-urea | 1709 (TUPS) |
| 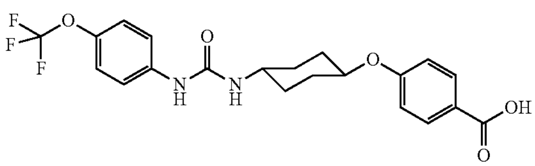 [SMILES: O=C(Nc1ccc(OC(F)(F)F)cc1)NC1CCC(Oc2ccc(C(=O)O)cc2)CC1] | trans-4-{4-[3-(4-Trifluoromethoxy-phenyl)-ureido]-cyclohexyloxy}-benzoic acid | 1728 (tTUCB) |
| 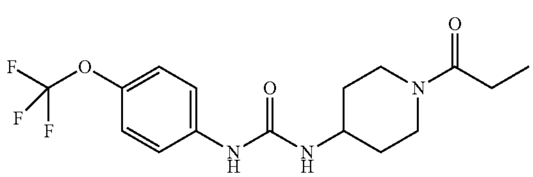 [SMILES: CCC(=O)N1CCC(NC(=O)Nc2ccc(OC(F)(F)F)cc2)CC1] | 1-trifluoromethoxyphenyl-3-(1-propionylpiperidin-4-yl) urea | 1770 (TPPU) |
| 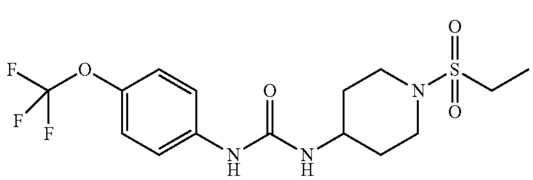 [SMILES: CCS(=O)(=O)N1CCC(NC(=O)Nc2ccc(OC(F)(F)F)cc2)CC1] | 1-(1-ethylsulfonyl-piperidin-4-yl)-3-(4-trifluoromethoxy-phenyl)-urea | 2213 (TUPSE) |
| 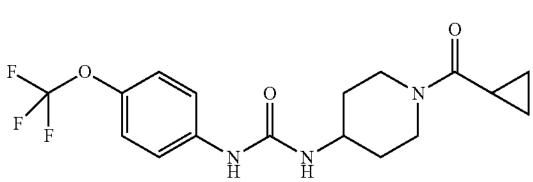 [SMILES: O=C(Nc1ccc(OC(F)(F)F)cc1)NC1CCN(C(=O)C2CC2)CC1] | 1-(1-(cyclopropanecarbonyl)piperidin-4-yl)-3-(4-(trifluoromethoxy)phenyl)urea | 2214 (CPTU) |

TABLE 2-continued sEH inhibitors

| Structure | Name | sEHi # |
|---|---|---|
| 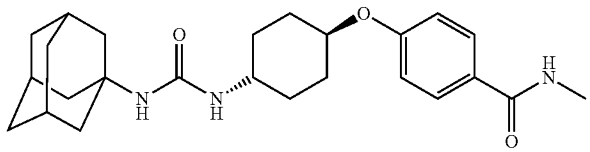 | trans-N-methyl-4-[4-(3-Adamantan-1-yl-ureido)-cyclohexyloxy]-benzamide | 2225 (tMAUCB) |
| 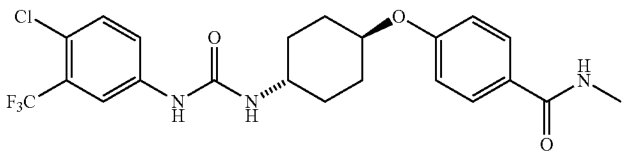 | trans-N-methyl-4-[4-((3-trifluoromethyl-4-chlorophenyl)-ureido)-cyclohexyloxy]-benzamide | 2226 (tMTCUCB) |
| 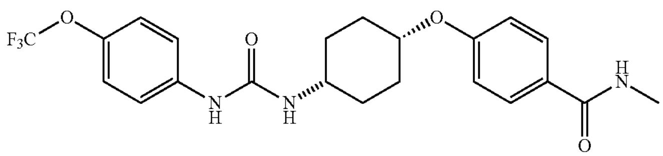 | cis-N-methyl-4-{4-[3-(4-trifluoromethoxy-phenyl)-ureido]-cyclohexyloxy}-benzamide | 2228 (cMTUCB) |
| 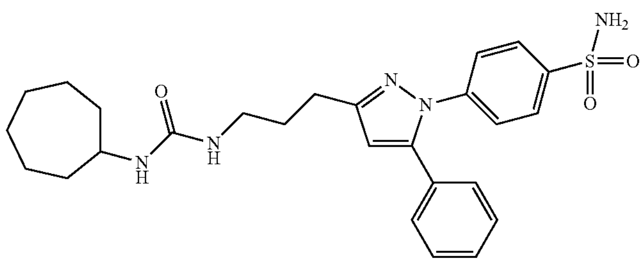 [SMILES: NS(=O)(=O)c1ccc(-n2nc(CCCNC(=O)NC3CCCCCC3)cc2-c2ccccc2)cc1] | 1-cycloheptyl-3-(3-(1,5-diphenyl-1H-pyrazol-3-yl)propyl)urea | 2247 (HDP3U) |

A number of other sEH inhibitors which can be used in the methods and compositions are set forth in co-owned applications PCT/US2013/024396, PCT/US2012/025074, PCT/US2011/064474, PCT/US2011/022901, PCT/US2008/072199, PCT/US2007/006412, PCT/US2005/038282, PCT/US2005/08765, PCT/US2004/010298 and U.S. Published Patent Application Publication Nos: 2014/0088156, 2014/0038923, 2013/0274476, 2013/0143925, 2013/0137726, 2011/0098322, 2005/0026844, each of which is hereby incorporated herein by reference in its entirety for all purposes.

U.S. Pat. No. 5,955,496 (the '496 patent) also sets forth a number of sEH inhibitors which can be used in the methods. One category of these inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods are set forth in U.S. Pat. No. 6,150,415 (the '415 patent) and U.S. Pat. No. 6,531,506 (the '506 patent). Two preferred classes of sEH inhibitors are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty sEH inhibitors of Formula 2, which were shown to inhibit human sEH at concentrations as low as 0.1 μM. Any particular sEH inhibitor can readily be tested to determine whether it will work in the methods by standard assays. Esters and salts of the various compounds discussed above or in the cited patents, for example, can be readily tested by these assays for their use in the methods.

As noted above, chalcone oxides can serve as an alternate substrate for the enzyme. While chalcone oxides have half-lives which depend in part on the particular structure, as a group the chalcone oxides tend to have relatively short half-lives (a drug's half-life is usually defined as the time for the concentration of the drug to drop to half its original value. See, e.g., Thomas, G., Medicinal Chemistry: an introduction, John Wiley & Sons Ltd. (West Sussex, England, 2000)). Since the various uses contemplate inhibition of sEH over differing periods of time which can be measured in days, weeks, or months, chalcone oxides, and other inhibitors which have a half-life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half-lives although, for inhibitors with a relatively short half-life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, the sEH inhibitor used in the methods taught herein is a "soft drug." Soft drugs are compounds of biological activity that are rapidly inactivated by enzymes as they move from a chosen target site. EETs and simple biodegradable derivatives administered to an area of interest may be considered to be soft drugs in that they are likely to be enzymatically degraded by sEH as they diffuse away from the site of interest following administration. Some sEHI, however, may diffuse or be transported following administration to regions where their activity in inhibiting sEH may not be desired. Thus, multiple soft drugs for treatment have been prepared. These include but are not limited to carbamates, esters, carbonates and amides placed in the sEHI, approximately 7.5 angstroms from the carbonyl of the central pharmacophore. These are highly active sEHI that yield biologically inactive metabolites by the action of esterase and/or amidase. Groups such as amides and carbamates on the central pharmacophores can also be used to increase solubility for applications in which that is desirable in forming a soft drug. Similarly, easily metabolized ethers may contribute soft drug properties and also increase the solubility.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

In various embodiments, a compound with combined functionality to concurrently inhibit sEH and COX-2 is administered. Urea-containing pyrazoles that function as dual inhibitors of cyclooxygenase-2 and soluble epoxide hydrolase are described, e.g., in Hwang, et al., *J Med Chem.* (2011) 28; 54(8):3037-50.

Preferably, the inhibitor inhibits sEH without also significantly inhibiting microsomal epoxide hydrolase ("mEH"). Preferably, at concentrations of 100 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 100 µM. Inhibitors with $IC_{50}$s of less than 100 µM are preferred, with $IC_{50}$s of less than 75 µM being more preferred and, in order of increasing preference, an $IC_{50}$ of 50 µM, 40 µM, 30 µM, 25 µM, 20 µM, 15 µM, 10 µM, 5 µM, 3 µM, 2 µM, 1 µM, 100 nM, 10 nM, 1.0 nM, or even less, being still more preferred. Assays for determining sEH activity are known in the art and described elsewhere herein. The $IC_{50}$ determination of the inhibitor can be made with respect to an sEH enzyme from the species subject to treatment (e.g., the subject receiving the inhibitor of sEH).

b. Cis-Epoxyeicosantrienoic Acids ("EETs")

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

It has long been believed that EETs administered systemically would be hydrolyzed too quickly by endogenous sEH to be helpful. For example, in one prior report of EETs administration, EETs were administered by catheters inserted into mouse aortas. The EETs were infused continuously during the course of the experiment because of concerns over the short half-life of the EETs. See, Liao and Zeldin, International Publication WO 01/10438 (hereafter "Liao and Zeldin"). It also was not known whether endogenous sEH could be inhibited sufficiently in body tissues to permit administration of exogenous EET to result in increased levels of EETs over those normally present. Further, it was thought that EETs, as epoxides, would be too labile to survive the storage and handling necessary for therapeutic use.

Studies from the laboratory of the present inventors, however, showed that systemic administration of EETs in conjunction with inhibitors of sEH had better results than did administration of sEH inhibitors alone. EETs were not administered by themselves in these studies since it was anticipated they would be degraded too quickly to have a useful effect. Additional studies from the laboratory of the present inventors have since shown, however, that administration of EETs by themselves has had therapeutic effect. Without wishing to be bound by theory, it is surmised that the exogenous EET overwhelms endogenous sEH, and allows EETs levels to be increased for a sufficient period of time to have therapeutic effect. Thus, EETs can be administered without also administering an sEHI to provide a therapeutic effect. Moreover, EETs, if not exposed to acidic conditions or to sEH are stable and can withstand reasonable storage, handling and administration.

In short, sEHI, EETs, or co-administration of sEHIs and of EETs, can be used in the methods of the present invention. In some embodiments, one or more EETs are administered to the patient without also administering an sEHI. In some embodiments, one or more EETs are administered shortly before or concurrently with administration of an sEH inhibitor to slow hydrolysis of the EET or EETs. In some embodiments, one or more EETs are administered after administration of an sEH inhibitor, but before the level of the sEHI has diminished below a level effective to slow the hydrolysis of the EETs.

EETs useful in the methods of the present invention include 14,15-EET, 8,9-EET and 11,12-EET, and 5,6 EETs. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, urea, amide, carbamate, difluorocyclopropane, or carbonyl, while in others, the carboxylic acid moiety is stabilized by blocking beta oxidation or is replaced with a commonly used mimic, such as a nitrogen heterocycle, a sulfonamide, or another polar functionality. In preferred forms, the analogs or derivatives are relatively stable as compared to an unmodified EET because they are more resistant than an unmodified EET to sEH and to chemical breakdown. "Relatively stable" means the rate of hydrolysis by sEH is at least 25% less than the hydrolysis of the unmodified EET in a hydrolysis assay, and more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. Whether or not a particular EET analog or derivative has the biological activity of the unmodified EET can be readily determined by using it in standard assays, such as radio-ligand competition assays to measure binding to the relevant receptor. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice.

c. Phosphodiesterase Inhibitors (PDEi)

Phosphodiesterase inhibitors (PDEi) are well known anti-inflammatory agents. Many different classes of isozyme selective PDEi lead to remarkable increases in the plasma levels of a broad range of epoxy-fatty acids (EFA). The magnitude of this increase is so dramatic that PDEi can elevate epoxy-fatty acids as well as highly potent inhibitors of soluble epoxide hydrolase. Accordingly, levels of epoxygenated fatty acids (e.g., in blood, plasma, serum) can be increased by administration of a phosphodiesterase inhibitor (PDEi).

The PDEi may or may not be selective, specific or preferential for cAMP. Exemplary PDEs that degrade cAMP include without limitation PDE3, PDE4, PDE7, PDE8 and PDE10. Exemplary cAMP selective hydrolases include PDE4, 7 and 8. Exemplary PDEs that hydrolyse both cAMP and cGMP include PDE1, PDE2, PDE3, PDE10 and PDE11. Isoenzymes and isoforms of PDEs are well known in the art. See, e.g., Boswell-Smith et al., Brit. J. Pharmacol. 147: S252-257 (2006), and Reneerkens, et al., Psychopharmacology (2009) 202:419-443, the contents of which are incorporated herein by reference.

In some embodiments, the PDE inhibitor is a non-selective inhibitor of PDE. Exemplary non-selective PDE inhibitors that find use include without limitation caffeine, theophylline, isobutylmethylxanthine, aminophylline, pentoxifylline, vasoactive intestinal peptide (VIP), secretin, adrenocorticotropic hormone, pilocarpine, alpha-melanocyte stimulating hormone (MSH), beta-MSH, gamma-MSH, the ionophore A23187, prostaglandin E1.

In some embodiments, the PDE inhibitor used specifically or preferentially inhibits PDE4. Exemplary inhibitors that selectively inhibit PDE4 include without limitation rolipram, roflumilast, cilomilast, ariflo, HT0712, ibudilast and mesembrine.

In some embodiments, the PDE inhibitor used specifically or preferentially inhibits a cAMP PDE, e.g., PDE4, PDE7 or PDE8. In some embodiments, the PDE inhibitor used inhibits a cAMP PDE, e.g., PDE1, PDE2, PDE3, PDE4, PDE7, PDE8, PDE10 or PDE11. Exemplary agents that inhibit a cAMP phosphodiesterase include without limitation rolipram, roflumilast, cilomilast, ariflo, HT0712, ibudilast, mesembrine, cilostamide, enoxamone, milrinone, siguazodan and BRL-50481.

In some embodiments, the PDE inhibitor used specifically inhibits PDE5. Exemplary inhibitors that selectively inhibit PDE5 include without limitation sildenafil, zaprinast, tadalafil, udenafil, avanafil and vardenafil.

d. Assays for Epoxide Hydrolase Activity

Any of a number of standard assays for determining epoxide hydrolase activity can be used to determine inhibition of sEH. For example, suitable assays are described in Gill, et al., Anal Biochem 131:273-282 (1983); and Borhan, et al., Analytical Biochemistry 231:188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174: 291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous methods of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

e. Other Means of Inhibiting sEH Activity

Other means of inhibiting sEH activity or gene expression can also be used in the methods. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and microRNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, siRNA were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). An exemplary amino acid sequence of human sEH (GenBank Accession No. L05779 or AAA02756; SEQ ID NO:1) and an exemplary nucleotide sequence encoding that amino acid sequence (GenBank Accession No. L05779; SEQ ID NO:2) are set forth in U.S. Pat. No. 5,445,956. The nucleic acid sequence of human sEH is also published as GenBank Accession No. NM_001979.4; the amino acid sequence of human sEH is also published as GenBank Accession No. NP_001970.2.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

For example, using the program available from the Whitehead Institute, the following sEH target sequences and siRNA sequences can be generated:

```
1) Target:
                              (SEQ ID NO: 3)
CAGTGTTCATTGGCCATGACTGG Sense-siRNA:
                              (SEQ ID NO: 4)
5'-GUGUUCAUUGGCCAUGACUTT-3'

Antisense-siRNA:
                              (SEQ ID NO: 5)
5'-AGUCAUGGCCAAUGAACACTT-3'

2) Target:
                              (SEQ ID NO: 6)
GAAAGGCTATGGAGAGTCATCTG

Sense-siRNA:
                              (SEQ ID NO: 7)
5'-AAGGCUAUGGAGAGUCAUCTT-3'

Antisense-siRNA:
                              (SEQ ID NO: 8)
5'-GAUGACUCUCCAUAGCCUUTT-3'

3) Target
                              (SEQ ID NO: 9)
AAAGGCTATGGAGAGTCATCTGC

Sense-siRNA:
                              (SEQ ID NO: 10)
5'-AGGCUAUGGAGAGUCAUCUTT-3'

Antisense-siRNA:
                              (SEQ ID NO: 11)
5'-AGAUGACUCUCCAUAGCCUTT-3'

4) Target:
                              (SEQ ID NO: 12)
CAAGCAGTGTTCATTGGCCATGA Sense-siRNA:
                              (SEQ ID NO: 13)
5'-AGCAGUGUUCAUUGGCCAUTT-3'

Antisense-siRNA:
                              (SEQ ID NO 14)
5'-AUGGCCAAUGAACACUGCUTT-3'

5) Target:
                              (SEQ ID NO: 15)
CAGCACATGGAGGACTGGATTCC Sense-siRNA:
                              (SEQ ID NO: 16)
5'-GCACAUGGAGGACUGGAUUTT-3'

Antisense-siRNA:
                              (SEQ ID NO: 17)
5'-AAUCCAGUCCUCCAUGUGCTT-3'
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

1) Target:
(SEQ ID NO: 19)
CAGTGTTCATTGGCCATGACTGG

Sense strand:
(SEQ ID NO: 20)
5'-GATCCCCGTGTTCATTGGCCATGACTTTCAA
GAGAAGTCATGGCCAATGAACACTTTTT-3'

Antisense strand:
(SEQ ID NO: 21)
5'-AGCTAAAAAGTGTTCATTGGCCATGACTTCTCTT
GAAAGTCATGGCCAATGAACACGGG-3'

2) Target:
(SEQ ID NO: 22)
GAAAGGCTATGGAGAGTCATCTG

Sense strand:
(SEQ ID NO: 23)
5'-GATCCCCAAGGCTATGGAGAGTCATCTTCAAGAGAGA
TGACTCTCCATAGCCTTTTTT-3'

Antisense strand:
(SEQ ID NO: 24)
5'-AGCTAAAAAAAGGCTATGGAGAGTCATCTCTCTTGAA
GATGACTCTCCATAGCCTTGGG-3'

3) Target:
(SEQ ID NO: 25)
AAAGGCTATGGAGAGTCATCTGC

Sense strand:
(SEQ ID NO: 26)
5'-GATCCCCAGGCTATGGAGAGTCATCTTTCAAGAAG
ATGACTCTCCATAGCCTTTTTT-3'

Antisense strand:
(SEQ ID NO: 27)
5'-AGCTAAAAAAGGCTATGGAGAGTCATCATCTCTTGAAAGATGACTCT
CCATAGCCTGGG-3'

4) Target:
(SEQ ID NO: 28)
CAAGCAGTGTTCATTGGCCATGA

Sense strand:
(SEQ ID NO: 29)
5'-GATCCCCAGCAGTGTTCATTGGCCATTTCAAGAGAATG
GCCAATGAACACTGCTTTTTT-3'

Antisense strand:
(SEQ ID NO: 30)
5'-AGCTAAAAAAGCAGTGTTCATTGGCCATTCTCTTGAAATG
GCCAATGAACACTGCTGGG-3'

5) Target:
(SEQ ID NO: 31)
CAGCACATGGAGGACTGGATTCC

Sense strand
(SEQ ID NO: 32)
5'-GATCCCCGCACATGGAGGACTGGATTTTCAAGAGAAATC
CAGTCCTCCATGTGCTTTTT-3'

Antisense strand:
(SEQ ID NO: 33)
5'-AGCTAAAAAGCACATGGAGGACTGGATTTCTCTTGAAAA
TCCAGTCCTCCATGTGCGGG-3'

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264:17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program found on the worldwide web "biotools.idtdna.com/antisense/AntiSense.aspx", which will provide appropriate antisense sequences for nucleic acid sequences up to 10,000 nucleotides in length. Using this program with the sEH gene provides the following exemplar sequences:

1)
(SEQ ID NO: 34)
UGUCCAGUGCCCACAGUCCU 2)
(SEQ ID NO: 35)
UUCCCACCUGACACGACUCU 3)
(SEQ ID NO: 36)
GUUCAGCCUCAGCCACUCCU 4)
(SEQ ID NO: 37)
AGUCCUCCCGCUUCACAGA 5)
(SEQ ID NO: 38)
GCCCACUUCCAGUUCCUUUCC

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand are transcribed and act as an antisense oligonucleotide.

It are appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found on the worldwide web at "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4):1290-7 (2005); Robins and Padgett, Proc Natl Acad Sci USA. 102(11): 4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

f. Epoxygenated Fatty Acids

In some embodiments, an epoxygenated fatty acid is administered as an agent that increases epoxygenated fatty acids. Illustrative epoxygenated fatty acids include epoxides of linoleic acid, eicosapentaenoic acid ("EPA") and docosahexaenoic acid ("DHA").

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, increasing the levels of epoxides of EPA, of DHA, or of both, will act to reduce pain and inflammation, and symptoms associated with diabetes and metabolic syndromes, in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogeous production of these epoxides is low and usually occurs in relatively special circumstances, such as the resolution of inflammation. Our expectation is that administering these epoxides from exogenous sources will aid in the resolution of inflammation and in reducing pain, as well as with symptoms of diabetes and metabolic syndromes. It is further beneficial with pain or inflammation to inhibit sEH with sEHI to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table 3:

TABLE 3

Regioisomers of Eicosapentaenoic acid ("EPA") epoxides:
1. Formal name: (±)5(6)-epoxy-8Z,11Z,14Z,17Z-eicosatetraenoic acid,
    Synonym 5(6)-epoxy Eicosatetraenoic acid
    Abbreviation 5(6)-EpETE
2. Formal name: (±)8(9)-epoxy-5Z,11Z,14Z,17Z-eicosatetraenoic acid,
    Synonym 8(9)-epoxy Eicosatetraenoic acid
    Abbreviation 8(9)-EpETE
3. Formal name: (±)11(12)-epoxy-5Z,8Z,14Z,17Z-eicosatetraenoic acid,
    Synonym 11(12)-epoxy Eicosatetraenoic acid
    Abbreviation 11(12)-EpETE
4. Formal name: (±)14(15)-epoxy-5Z,8Z,11Z,17Z-eicosatetraenoic acid,
    Synonym 14(15)-epoxy Eicosatetraenoic acid
    Abbreviation 14(15)-EpETE
5. Formal name: (±)17(18)-epoxy-5Z,8Z,11Z,14Z-eicosatetraenoic acid,
    Synonym 17(18)-epoxy Eicosatetraenoic acid
    Abbreviation 17(18)-EpETE
Regioisomers of Docosahexaenoic acid ("DHA") epoxides:
1. Formal name: (±) 4(5)-epoxy-7Z,10Z,13Z,16Z,19Z-docosapentaenoic acid,
    Synonym 4(5)-epoxy Docosapentaenoic acid
    Abbreviation 4(5)-EpDPE
2. Formal name: (±) 7(8)-epoxy-4Z,10Z,13Z,16Z,19Z-docosapentaenoic acid,
    Synonym 7(8)-epoxy Docosapentaenoic acid
    Abbreviation 7(8)-EpDPE
3. Formal name: (±)10(11)-epoxy-4Z,7Z,13Z,16Z,19Z-docosapentaenoic acid,
    Synonym 10(11)-epoxy Docosapentaenoic acid
    Abbreviation 10(11)-EpDPE
4. Formal name: (±)13(14)-epoxy-4Z,7Z,10Z,16Z,19Z-docosapentaenoic acid,
    Synonym 13(14)-epoxy Docosapentaenoic acid
    Abbreviation 13(14)-EpDPE
5. Formal name: (±) 16(17)-epoxy-4Z,7Z,10Z,13Z,19Z-docosapentaenoic acid,
    Synonym 16(17)-epoxy Docosapentaenoic acid
    Abbreviation 16(17)-EpDPE
6. Formal name: (±) 19(20)-epoxy-4Z,7Z,10Z,13Z,16Z-docosapentaenoic acid,
    Synonym 19(20)-epoxy Docosapentaenoic acid
    Abbreviation 19(20)-EpDPE Any of these epoxides, or combinations of any of these, can be administered in the compositions and methods.

5. Formulation and Administration

In various embodiments of the compositions, the agent that increases epoxygenated fatty acids (e.g., an inhibitor of sEH, an EET, an epoxygenated fatty acid, and mixtures thereof) is co-administered with the agent that reduces and/or inhibits ER stress (e.g., PBA). In some embodiments, the agent that increases epoxygenated fatty acids comprises an epoxide of EPA, an epoxide of DHA, or epoxides of both, and an sEHI.

The agent that increases epoxygenated fatty acids and the agent that inhibits and/or reduces ER stress independently can be prepared and administered in a wide variety of oral, parenteral and topical dosage forms. The agent that increases epoxygenated fatty acids and the agent that inhibits and/or reduces ER stress can be administered via the same or different routes of administration. In varying embodiments, the agent that increases epoxygenated fatty acids and the agent that inhibits and/or reduces ER stress independently can be administered orally, by injection, that is, intravenously, intramuscularly, intracutaneously, subcutaneously, intraduodenally, or intraperitoneally. The agent that increases epoxygenated fatty acids and the agent that inhibits and/or reduces ER stress can also be administered by inhalation, for example, intranasally. Additionally, the agent that increases epoxygenated fatty acids and the agent that inhibits and/or reduces ER stress can be administered transdermally.

Furthermore, the agent that increases epoxygenated fatty acids and the agent that inhibits and/or reduces ER stress can be co-formulated in a single composition or can be formulated for separate co-administration. Accordingly, in some embodiments, the methods contemplate administration of compositions comprising a pharmaceutically acceptable carrier or excipient, an agent that increases epoxygenated fatty acids (e.g., an sEHI or a pharmaceutically acceptable salt of the inhibitor and, optionally, one or more EETs or epoxides of EPA or of DHA, or of both), and optionally an agent that reduces and/or inhibits ER stress. In some embodiments, the methods comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A variety of solid, semisolid and liquid vehicles have been known in the art for years for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®, substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

The agent that increases epoxygenated fatty acids (e.g., an inhibitor of sEH, an EET, an epoxygenated fatty acid, and mixtures thereof), optionally mixed with an anti-inflammatory and/or analgesic agent, can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In various embodiments, sEHI can be mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents that inhibit sEH are topically administered (that is, whether by solid, liquid, lotion, gel, spray, etc.), in various embodiments they are administered at a dosage of about 0.01 mg to 10 mg per 10 $cm^2$. An exemplary dose for systemic administration of an inhibitor of sEH is from about 0.001 μg/kg to about 100 mg/kg body weight of the mammal. In various embodiments, dose and frequency of administration of an sEH inhibitor are selected to produce plasma concentrations within the range of 2.5 μM and 30 nM.

The agent that increases epoxygenated fatty acids (e.g., an inhibitor of sEH, an EET, an epoxygenated fatty acid, and mixtures thereof), optionally mixed with an anti-inflammatory and/or analgesic agent, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification.

A therapeutically effective amount or a sub-therapeutic amount of the agent that increases epoxygenated fatty acids can be co-administered with the agent that reduces and/or inhibits ER stress (e.g., PBA). The dosage of the specific compounds depends on many factors that are well known to those skilled in the art. They include for example, the route of administration and the potency of the particular compound. An exemplary dose is from about 0.001 μg/kg to about 100 mg/kg body weight of the mammal. Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 12th Edition, 2010, McGraw-Hill Professional; in a Physicians' Desk Reference (PDR), 68$^{th}$ Edition, 2014, PDR Network; in *Remington: The Science and Practice of Pharmacy,* 21$^{st}$ Ed., 2005, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions are embedded in a slow-release formulation to facilitate administration of the agents over time.

It is understood that, like all drugs, sEHIs have half-lives defined by the rate at which they are metabolized by or excreted from the body, and that the sEHIs will have a period following administration during which they are present in amounts sufficient to be effective. If EETs, EpDPEs, or EpETEs are administered after the sEHI is administered, therefore, it is desirable that the EETs, EpDPEs, or EpETEs be administered during the period during which the sEHI are present in amounts to be effective in delaying hydrolysis of the EETs, EpDPEs, or EpETEs. Typically, the EETs, EpDPEs, or EpETEs are administered within 48 hours of administering an sEH inhibitor. Preferably, the EETs, EpDPEs, or EpETEs are administered within 24 hours of the sEHI, and even more preferably within 12 hours. In increasing order of desirability, the EETs, EpDPEs, or EpETEs are administered within 10, 8, 6, 4, 2, hours, 1 hour, or one half hour after administration of the inhibitor. When co-administered, the EETs, EpDPEs, or EpETEs are preferably administered concurrently with the sEHI.

6. Methods of Monitoring

Clinical efficacy can be monitored using any method known in the art. Measurable parameters to monitor efficacy will depend on the condition being treated. For monitoring the status or improvement of one or more symptoms associated with pain, both subjective parameters (e.g., patient reporting) and objective parameters (e.g., f-MRI, allodynia, hyperalgesia, physical exam, gait, mobility, walking distance, nerve conduction velocity, electrophysiology, etc.) can be used. Applicable assays for the measurement of pain are described, e.g., in "Pain: Current Understanding of Assessment, Management, and Treatments," The Joint Commission on Accreditation of Healthcare Organizations; The National Pharmaceutical Council Publication: December 2001 and later published editions (www.npcnow.org). For monitoring the status or improvement of one or more symptoms associated with cardiomyopathy, measurable parameters can include without limitation, auditory inspection (e.g., using a stethoscope), blood pressure, electrocardiogram (EKG), magnetic resonance imaging (MRI), changes in blood markers. Behavioral changes in the subject (e.g., appetite, the ability to eat solid foods, grooming, sociability, energy levels, increased activity levels, weight gain, exhibition of increased comfort) are also relevant to all diseases and disease conditions associated with and/or caused at least in part by ER stress. These parameters can be measured using any methods known in the art. In varying embodiments, the different parameters can be assigned a score. Further, the scores of two or more parameters can be combined to provide an index for the subject.

Observation of the stabilization, improvement and/or reversal of one or more symptoms or parameters by a measurable amount indicates that the treatment or prevention regime is efficacious. Observation of the progression, increase or exacerbation of one or more symptoms indicates that the treatment or prevention regime is not efficacious. For example, in the case of pain observation the improvement of one or both of subjective parameters (e.g., patient reporting) and objective parameters (e.g., f-MM, allodynia, hyperalgesia, physical exam, gait, mobility, walking distance, nerve conduction velocity, electrophysiology, etc.) and/or behavioral changes in the subject (e.g., increased appetite, the ability to eat solid foods, improved/increased grooming, improved/increased sociability, increased energy levels, improved/increased activity levels, weight gain and/or stabilization, exhibition of increased comfort) after one or more co-administrations of the agent that reduces and/or inhibits ER stress (e.g., PBA) with an agent that increases epoxygenated fatty acids (e.g., an inhibitor of sEH) indicates that the treatment or prevention regime is efficacious. In the case of cardiomyopathy, observation of the improvement of cardiac function (e.g., blood pressure in appropriate range, stable heart rhythm or reduction or absence of arrhythmias, changes in blood markers, and/or behavioral changes in the subject (e.g., increased appetite, the ability to eat solid foods, improved/increased grooming, improved/increased sociability, increased energy levels, improved/increased activity levels, weight gain and/or stabilization, exhibition of increased comfort) after one or more co-administrations of the agent that reduces and/or inhibits ER stress (e.g., PBA) with an agent that increases epoxygenated fatty acids (e.g., an inhibitor of sEH) indicates that the treatment or prevention regime is efficacious. Likewise, observation of reduction or decline of one or both of subjective parameters (e.g., patient reporting) and objective parameters (e.g., f-MRI, allodynia, hyperalgesia, physical exam, gait, mobility, walking distance, nerve conduction velocity, electrophysiology, etc.) related to pain, cardiac function (e.g., blood pressure in appropriate range, unstable heart rhythm or continued presence or increased arrhythmias, changes in blood markers, and/or behavioral changes in the subject (e.g., decreased appetite, the inability to eat solid foods, decreased grooming, decreased sociability, decreased energy levels, decreased activity levels, weight loss, exhibition of increased discomfort) after one or more co-administrations of the agent that reduces and/or inhibits ER stress (e.g., PBA) with an agent that increases epoxygenated fatty acids (e.g., an inhibitor of sEH) indicates that the treatment or prevention regime is not efficacious.

In certain embodiments, the monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. In certain embodiments, the individuals in the control population have not received prior treatment and do not have the disease condition subject to treatment (e.g., pain, cardiomyopathy or another disease condition associated with or caused at least in part by ER stress), nor are at risk of developing the disease condition subject to treatment (e.g., pain, cardiomyopathy or another disease condition associated with or caused at least in part by ER stress). In such cases, if the value of the measurable biomarker or clinical parameter approaches the control value, then treatment is considered efficacious. In other embodiments, the individuals in the control population have not received prior treatment and have been diagnosed with the disease condition subject to treatment (e.g., pain, cardiomyopathy or another disease condition associated with or caused at least in part by ER stress). In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (i.e., more than a standard deviation) is an indicator that treatment should be resumed in the subject.

7. Compositions and Kits

Further provided are kits. In varying embodiments, the kits comprise one or more agents that increase the production and/or level of epoxygenated fatty acids and one or more inhibitors of endoplasmic reticulum stress. Embodiments of the agents that increase the production and/or level of epoxygenated fatty acids and embodiments of inhibitors of endoplasmic reticulum stress are as described above and herein. Embodiments of formulations of the agents are as described above and herein. In varying embodiments, the agent that increases the production and/or level of epoxygenated fatty acids and the inhibitor of endoplasmic reticulum stress can be co-formulated for administration as a single composition. In some embodiments, the agent that increases the production and/or level of epoxygenated fatty acids and the inhibitor of endoplasmic reticulum stress are formulated for separate administration, e.g., via the same or different route of administration. In varying embodiments, one or both the agent that increases the production and/or level of epoxygenated fatty acids and the inhibitor of endoplasmic reticulum stress are provided in unitary dosages in the kits.

EXAMPLES

The following examples are offered to illustrate, but not to limit the claimed invention.

Example 1

ER Stress in the Peripheral Nervous System is a Significant Driver of Diabetes Mediated Neuropathic Pain: Reversal by a Chemical Chaperone and Lipid Epoxides Materials and Methods Chemicals and Reagents:

Antibodies for tubulin, p-PERK (Thr980), PERK, p-EIF2α (Ser51), EIF2α, sXBP1, cATF6 and IRE1α, were from Santa Cruz Biotechnology (Santa Cruz, Calif.). Primary antibodies for p38, pp38 (Thr180/Tyr182), BiP, JNK, p-JNK (Thr183/Tyr185), and Cox 2 were obtained from Cell Signaling Technology (Danvers, Mass.). Antibody for p-IRE1α (Ser724) was purchased from Abcam (Cambridge, Mass.). PVDF membranes and protein standards were obtained from BIO-RAD (Hercules, Calif.). The ECL Western blotting system was from Thermo Fisher Scientific Inc. (Piscataway, N.J.). All other reagents were from the highest quality available and were purchased from Sigma (St. Louis, Mo.).

Animals and Animal Care:

All procedures were in agreement with standards for the care of laboratory animals as outlined in the NIH Guide for the Care and Use of Laboratory Animals. All procedures were performed according to institutional guidelines for animal experimentation and were approved by the Animal Resource Services of the University of California, Davis, which is accredited by the American Association for the Accreditation of Laboratory Animal Care. Rats were housed under standard conditions, 12 h light-dark cycle and ad libitum food and water.

Western Blotting:

Tissues were homogenized in radio-immunoprecipitation assay buffer (RIPA, 10 mM Tris-HCl, pH 7.4, 150 mM NaCl, 0.1% w/v sodium dodecylsulfate, 1% w/v Triton X-100, 1% sodium deoxycholate, 5 mM EDTA, 1 mM NaF, 1 mM sodium orthovanadate and protease inhibitors). Homogenates were centrifuged at 13,000×g for 10 min, the supernatant collected, and protein concentrations were determined using a bicinchoninic acid protein assay kit (Pierce Chemical) according to the manufacturer's instructions. Aliquots of total cell lysates containing 25-40 μg protein were denatured with Laemmli buffer, resolved by SDS-PAGE and transferred to PVDF membranes. Membranes were blotted for 1 h in 5% (w/v) bovine serum albumin and subsequently incubated in the presence of corresponding primary antibodies (1:1,000 dilution for all the antibodies except pJNK, JNK, pp38 and p38 which were 1:5000) overnight at 4° C. After incubation for 60 min at room temperature in the presence of the HRP conjugated secondary antibody (1:10,000 dilution) the reacting bands were visualized using the ECL Western blotting system. Pixel intensities of immunoreactive bands were quantified using FluorChem Q Imaging software (Alpha Innotech, San Leandro, Calif.). For phosphorylated proteins data are presented as normalized signal of phosphorylated form to total target protein signal for each animal individually. For non-phosphorylated proteins normalization was performed using Tubulin for each animal individually. The graphs display mean signal intensity±SEM (Bettaieb, et al., *J Biol Chem* (2013) 88(20):14189-14199).

Quantitative RT-PCR:

Total RNA was extracted using TRIzol reagent (Invitrogen). cDNA was generated using a high-capacity cDNA synthesis Kit (Applied Biosystems). Bip, sXbp1 and Atf4 were assessed by SYBR Green quantitative real time PCR using SsoAdvanced™ Universal SYBR® Green Supermix (iCycler, BioRad). Relative gene expression was quantified using the ΔCT method with appropriate primers and normalized to Tata-box binding protein (Tbp). Briefly, the threshold cycle (Ct) was determined and relative gene expression was calculated as follows: fold change=$2^{-\Delta(\Delta Ct)}$, where ΔCt=Ct target gene-Ct Tbp (cycle difference) and Δ(ΔCt)=Ct (treated rats)−/Ct (control rats).

Nociceptive Models and Behavioral Tests:

The STZ (55 mg/kg, i.v.) induced rat neuropathic pain model is extensively described (Aley, et al., *J Pain* (2001) 2(3):146-150). For the tunicamycin and dimethylcelecoxib induced models these compounds were administered by intraplantar injection in a volume of 10 μL saline. Standard nociceptive measurements were performed in all experiments. For the von Frey test an electronic rigid tip instrument was used (IITC, Woodland Hills Calif.). For the thermal nociceptive thresholds the modified Hargreaves' method was used. The baseline withdrawal thresholds before STZ administration were taken as 100% response and all mean nociceptive thresholds were converted to percentage values. Inhibitors were administered by intraperitoneal route after completely dissolving in vehicle PEG400 (1 mL/kg). All data are presented as mean±standard error of mean (Inceoglu, et al., *Proc Natl Acad Sci USA* (2012) 109(28):11390-11395).

Statistical Analyses: Data were analyzed by parametric and non-parametric One-Way ANOVA followed by post hoc tests suggested by the SigmaPlot analysis package (Systat Software, Inc., Chicago, Ill.). Results are depicted as mean±SEM. CompuSyn software package was used to quantify the synergy between drugs.

Determination of inhibitor potency: Enzyme residence time refers to the dissociation rate constant ($k_{off}$) on a target enzyme. Recent work demonstrates that residence time is an important parameter that can better predict in vivo efficacy (Copeland, *Nat Rev Drug Discov* (2006) 5(9):730-739). In particular, we demonstrated that inhibitors of sEH with longer residence time display more efficacy in in vivo tests than those with shorter time of residence in the enzyme, using the diabetes mediated model of neuropathic pain (Lee, et al., *Anal Biochem* (2013) 434(2):259-268; Lee, et al., *J Med Chem* (2014) 57(16):7016-7030). These properties for TPPU used in this study include excellent inhibitory potency with a long enzyme residence time and are displayed in Table 4.

TABLE 4

In vitro potency of 1-(1-propionylpiperidin-4-yl)-3-(4-(trifluoromethoxy) phenyl)urea (TPPU) against recombinant rat and human sEH enzyme

|  | $K_i$ (nM)[a] | $IC_{50}$ (nM)[b] | $t_{1/2}$ (min)[c] |
|---|---|---|---|
| Human | 0.91 | 34 | 11 |
| Rat | Not determined | 29 | 13 |

[a]$K_i$ was determined by FRET-based displacement assay
[b]$IC_{50}$ was determined by enzyme kinetic using [$^{3}H$]-tDPPO as radioactive substrate.
[c]$t_{1/2}$ is defined as the time required for half of the drug being dissociated from the enzyme based on the fluorescence signals.

Results

Active ER Stress Responses in Diabetic PNS Demystify Symptoms of Diabetic Polyneuropathy The sequelae in neuropathy could be driven by ER stress responses. Although ER stress is widely recognized to occur due to failure to fold and stabilize proteins, other drivers are also able to activate ER stress pathways (Stetler 2010 Prog Neurobiol). Among these, chronic high glucose activates the canonical UPR (unfolded protein response) branches in diabetic beta islets. Consistent with this idea we first asked if ER stress mediated pathways are active in the PNS of type I diabetic rats. Streptozocin induced type I diabetes results in high blood glucose and neuropathy measured as increased sensitivity to touch (FIG. 1). Rats that have been diabetic for two weeks and display sensitivity to tactile stimuli also have significantly activated ER stress responses in the glabrous skin of the hind paw and the sciatic nerve (FIG. 2A-D, and FIGS. 3 and 4). Robust increases in activation of PERK (Thr980), Ire1α (Ser727) and ATF6, three key components of the ER stress signaling pathways are observed. Expectedly, the levels of the associated downstream target cascades are elevated suggesting full-scale activation of the ER stress pathways. Consistent with this observation, phosphorylation of eIF2α (Ser51), mediated by phospho-PERK, increased the mRNA levels of its downstream target ATF4. Similarly, phosphorylation of IRE1α led to a significant rise in total protein and mRNA levels of spliced XBP1, as well as the level of the ER chaperone BiP in both tissues. Equally importantly, the levels of pp38 and pJNK1/2 two agreed upon kinase mediators of neuropathic pain are significantly increased, consistent with our conclusions (18). Remarkably, age matched healthy rats have exceedingly low levels of phosphorylated PERK, Ire1α, eIF2α and cleaved cATF demonstrating the selectivity of these ER stress responses.

A hallmark of mounting of ER stress is activation of autophagy pathways in an effort to maintain homeostasis. In diabetic rats, sciatic and skin levels of the autophagy markers LC3 and beclin are significantly increased (FIG. 5). This demonstrates a continuous and organized effort to replenish subcellular structures.

Diverse Agents that Suppress Molecular Markers of ER Stress Response Block Pain

A similar observation on ER stress is described by Lupachyk et al. for the sciatic nerve and spinal cord of type I diabetic rats where pain related behavior is prevented using two distinct chemical chaperones administered for 12 weeks at high doses (19). If there is a causal relationship between diabetes mediated neuropathic pain and ER stress, in particular through rapid phosphorylation, chemical chaperones that reduce ER stress should block pain and reduce the levels of biomarkers of ER stress immediately rather than following lengthy administration. Indeed, when chemical chaperone 4-PBA (4-phenyl butyric acid) is administered to diabetic rats, dose and time dependent antinociception occurs within minutes, whereas 4-PBA is not antinociceptive in healthy rats. (FIGS. 2E and 2F). Surprisingly, systemic delivery of 4-PBA at the highest dose generates full efficacy and rapid onset. This outcome alone provides a rationale for the testing or therapeutic use of FDA approved ER stress blocking drugs against painful neuropathic conditions.

Results from Lupachyk et al. and this study support the idea that hyperglycemia mediated activation of ER stress occurs in the PNS and the CNS of diabetics (19). These observations further support the idea that ER stress is involved in the etiology of diabetic neuropathy. In essence, the finding that one can modulate ER stress within minutes in vivo lends support to the conclusion that pain and ER stress are functionally linked. Therefore, our results open routes to the development of novel probes and drug candidates on multiple targets in and around the cannonical ER stress pathways while reiterating p38 and JNK as feasible therapeutic targets to address complex painful conditions (18).

Next, we asked if a different class of ER stress blocking compound would block neuropathic pain by switching off ER stress sensors. Increasing the levels of epoxy fatty acids (EpFAs) by inhibiting the enzyme sEH effectively accomplishes this goal in the liver and adipose tissue of mice on a high fat diet (17). However, sEH inhibitors are also powerful analgesics, and specifically in diabetic rats, they eliminate pain-related behavior in a time and dose dependent manner (7). Indeed, blood levels of sEH inhibitors, changes in epoxy fatty acids and antinociceptive activity triangulate to full target engagement. Here, a newer and orally available inhibitor, TPPU, displays higher efficacy than earlier sEH inhibitors as would be expected from its higher in vitro potency (measured using baculovirus expressed recombinant rat sEH, FIG. 2G) (20). More to the point, full-blown ER stress and downstream responses are significantly reduced in the skin and largely normalized in the sciatic nerve by TPPU by 30 min post administration (FIG. 2A-D). In the sciatic nerve, phosphorylation of PERK (Thr980), eIF2α (Ser51) and Ire1α (Ser727) as well as the induction of BiP are effectively extinguished by TPPU along with significant decreases in sXBP1 and cleaved ATF6 expression. These follow the drastic decreases in the mRNA levels of BiP, sXBP1 and ATF4. Equally importantly, established kinase mediators of neuropathic pain pp38 and pJNK are similarly normalized by TPPU as early as 30 min reinforcing the role of ER stress in pain. Notably, in healthy animals inhibition of sEH does not lead to changes in ER stress pathways, which is echoed in the absence of nociceptive threshold changes in healthy animals receiving sEH inhibitors.

Equivalent suppression of the three UPR branches place epoxy fatty acids upstream of the ER stress sensors and argue for the use of EpFAs and their mimics and sEH inhibitors as novel probes that modulate ER stress responses. Furthermore, these findings lend support to the conclusion that a major role of EpFAs is modulation of ER stress and the mechanism of analgesia observed by sEH inhibitors is at least partially based on dampening ER stress.

Concurrent Use of sEH Inhibitor and 4-PBA Synergistically Block Pain and ER Stress If sEH inhibition blocks pain by way of preventing the mounting of the ER stress responses, there should be a synergistic reduction in pain when 4-PBA, a chemical chaperone, and sEH inhibitor are co-administered, in particular if these two agents have targets in the same biological cascade (21). Thus the combination of sub-therapeutic doses of 4-PBA (10 mg/kg) and TPPU (0.01, 0.03 and 0.1 mg/kg) were examined in diabetic rats (22). TPPU and 4-PBA synergistically block pain with significant CI (combination index) and DRI (drug reduction index) values (FIG. 6 and Table 5). These findings are consistent with the conclusion that 4-PBA treatment and sEH inhibition block pain by reducing ER stress.

TABLE 5

Parameters of synergistic reduction of pain by combination of 4-PBA and TPPU

|  | at $ED_{50}$ | at $ED_{97}$ |
| --- | --- | --- |
| Combination index (CI) | 0.63* | 0.25** |
| Drug reduction index for TPPU | 4.9 fold | 218 fold |
| Drug reduction index for 4-PBA | 2.2 fold | 3.9 fold |

*CI<1 indicates synergistic interaction,
**CI <0.3 indicates strong synergistic interaction Diverse Agents that Induce ER Stress Concurrently Induce Pain Although these results demonstrate high synchronicity between ER stress in the PNS and the pain modality we asked if inducers of ER stress modulate pain sensation. Two compounds that are well established inducers of ER stress include the glycosylation inhibitor tunicamycin (Tm) and the SERCA modulator dimethyl-celecoxib (DMCx). Both compounds induce a significant degree of pain when administered into the intraplantar region of the hind paw of healthy rats (FIG. 7) (23, 24). The effects are dose and time dependent demonstrating specificity of the interaction of ER stress pathways with the nociceptive system. Tm does not induce any immediate nocifensive behavior however, shortly after injection rats display discomfort, licking, shaking and guarding of the affected paw for a brief period of several minutes after which guarding remains while other behaviors subside. Minimal amount of swelling occurred after Tm, although the mechanical withdrawal threshold is quickly reduced down to 25% of the baseline levels (FIG. 7A). The speed and magnitude of decrease is notably fast and intense. This results in a larger assay dynamic range for quantification of anti-nociceptive compounds. Remarkably, the contralateral paw measurements demonstrate PNS restricted phenotype, at the least during the course of the measurements. To our surprise, Tm administration resulted in rapid and sustained loss of heat responses of the ipsilateral paw while animals become more sensitive to tactile stimuli displaying a diabetic like pain-related behavior profile (FIG. 7C). Next we characterized the pharmacologic profile of this novel pain model. Increased sensitivity to mechanical stimuli is reversed using intermediate doses of TPPU and 4-PBA (FIGS. 7D and 7E). At the same time, we demonstrate that Tm induced hyperalgesia is resistant to celecoxib (FIG. 7F). Overall, these results are consistent with the pharmacologic profile of neuropathic pain that is typically non-responsive to NSAIDs and reversed by sEH inhibition.

Concurrent with the Tm induced phenotypic effects on pain, molecular markers of ER stress are modulated in a predictable way (FIG. 8A-D). All major markers of ER stress are activated either as increased phosphorylated forms or as higher levels of transcripts and translated proteins. The acute sampling time after ER stress induction (30 min after Tm) demonstrates surprisingly synchronous pain and clear ER stress response occurring in an identical time frame. Quantification of contralateral paw ER stress markers concur with the results of pain measurements, a lack of activation on vehicle administered contralateral paw. This is also consistent with the results from sEH inhibitor alone groups where no significant changes occur in the absence of induced pain or neuropathy. Consistent with results in diabetic rats, Tm induced ER stress markers are reduced below detectable levels by inhibition of sEH. Similarly, inhibition of sEH seems to have equipotent effects on all three major branches of the UPR. It is currently unknown if EpFAs are modulating all three branches equally or an upstream event from the activation of these three branches. Surprisingly, the 30 min treatment with Tm is sufficient to initiate apoptotic and autophagic responses, both of which are blocked by inhibition of sEH at the level of skin and sciatic nerve (FIG. 5).

A mechanistically different ER stress inducer, dimethyl celecoxib (DMCx) generated a similar painful phenotype (FIG. 9)(25). DMCx was as potent as Tm but has a marked inflammatory component since celecoxib is partially effective in reversing this pain (FIG. 9C). Unlike Tm, DMCx does not lead to loss of heat sensation even though it is as rapid as Tm in initiating nociceptive responses. Swelling of the ipsilateral paw is also consistent with the inflammatory phenotype of DMCx induced pain. Although molecular markers of ER stress were not investigated in these groups inhibition of sEH was strongly analgesic, consistent with our conclusion.

Activation of ER Stress in the PNS by Suprathreshold Heat Stimuli is not Blocked Under Deep Anesthesia Throughout this study our sampling approach was not tuned to provide detailed information on the spatial origin of the observed effects. In an effort to understand if motor unit activation would lead to ER stress in the sciatic nerve bundle we asked if markers of ER stress are phosphorylated when rats were forced to remain on a 16 rpm rotating rotorod apparatus for 10 min compared to rats that were rested. Even though a delay of about 3 min from the time rats stopped moving and tissues were excised and frozen occur, we anticipated detecting increased phosphorylation if sustained firing of motor neurons lead to activation of ER stress responses. However, in these rats the sciatic tissue did not show an increase in phosphorylated ER stress markers suggesting that these were not activated in response to neuronal activity or low grade motor neuron activity (FIG. 10A). To test if ER stress is a correlate of nociceptive unit activation, all neuronal activity was blocked under deep anesthesia and one hind paw was stimulated with suprathreshold heat exposure (53° C., 10 sec). Under isoflurane anesthesia (>1.5×MAC), this treatment did not result in withdrawal reflex demonstrating that neither motor nor sensory systems were transmitting information. Significant phosphorylation of ER stress markers were seen in the ipsilateral sciatic nerve (FIG. 10B). These results suggest that activation of ER stress responses may be a prerequisite for nociceptors to propagate signal proximally towards the spinal cord. Furthermore, these results argue that the signals on the western blots may largely originate from neuronal sources since one would not expect the Schwann cells supporting the sciatic nerve to be heated with this treatment. Overall we find a remarkable degree of selectivity in activation of ER stress in response to neuronal activity.

Discussion

The novelty reported here is important from a fundamental scientific perspective since a knowledge gap in the mechanism of nerve injury induced pain is filled. It is also important from an applied perspective since neuropathic pain remains a significant unmet clinical need. Painful diabetic neuropathy is one of the most challenging co-morbidities of diabetes (26, 27). Its etiology is complex and poorly understood. Moreover, few therapeutic options exist. Currently approved drugs for neuropathic pain invariably address the increased hyperexcitability of nerves, a time-tested strategy. However understanding the underlying cause of increased hyperexcitability and developing drugs that target these processes is an equally sought after strategy which should bring us steps closer to more selective and efficacious therapeutics that spare normal nerve function.

Activation of the ER stress responses has long been reported in diabetes and metabolic disease models and patients (28,29). Here, we extended these findings to the PNS and distinctively demonstrate a rapidly observable functional change occurring within minutes as a pain phenotype in response to ER stress. In the diabetic PNS, activated ER stress responses are prominent and seem causal to the painful phenotype. The suppression of ER stress using a chemical chaperone or novel EpFA stabilizing sEH inhibitor led to rapid reduction of pain and ER stress. Co-administration of these two types of agents synergistically block pain and ER stress. Activation of ER stress by multiple independent methods, inducing systemic hyperglycemia, artificially by blocking correct protein folding and generating intracellular calcium imbalance in the hind paw tissue invariably result in strong painful phenotypes, although with dissimilar characteristics. We demonstrated anesthetic block did not prevent ER stress responses in the sciatic nerve bundle following exposure of the hind paw to brief but above threshold heat treatment. These results suggest selectivity of the ER stress responses to nociceptive neuronal firing rather than neuronal activity. Accordingly, in healthy animals, 4-PBA or sEH inhibitors do not modulate canonical ER stress markers or baseline nociceptive thresholds. Overall a causal association between ER stress responses and pain is proposed. This outcome, if true, opens routes to examining more than a dozen potential ER stress related therapeutic targets with existing probes to ask if they would also address complex pain problems in human and companion animal patients.

The observed effects on phosphorylation of p38 and its substrate JNK, two well recognized pain modulating kinases add to our confidence regarding the conclusion that ER stress is an underlying mechanism in multiple painful syndromes. The upstream factors that lead to the activation of p38 and JNK have been postulated but not investigated in detail (18). Our finding that they take part in the orchestration of ER stress responses reveals information about their upstream regulators in addition to pinning down ER stress as a common denominator for pain. Aside from these two kinases a large number of players in the ER stress pathways are well characterized (30). Although these targets have not been considered in the context of pain our results strongly argue for their exploration. Specifically for diabetic neuropathy, our findings are consistent with knowledge generated over the past 50 years. A key example of this is morphological changes easily recognized and described early on match activation of autophagic and apoptotic cascades (i.e., dying back of distal ends of primary afferents). It is well known that during diabetes different classes of primary afferents go through a continuum of different stages i.e., cells transmitting heat related information first become more sensitive, and then over time their responses diminish (31). A similar pattern is captured here using Tm (tunicamycin). Unilateral intraplantar injection of a small amount of Tm leads to mechanical hyperalgesia and thermal hypoalgesia and the phenotype is maintained on the ipsilateral side. Both hyperglycemia and Tm lead to increases in not only ER stress markers but also markers of autophagy and apoptosis, reduced by both 4-PBA and sEH inhibition. Autophagy and apoptosis likely progress simultaneously in the diabetic PNS which could be driven by ER stress related pathways. Selective changes that are seen in different types of primary afferents could be because of yet unidentified susceptibility factors or could simply be related to exposure of cells to the stressors. Regardless, the complexity in the etiology of diabetic neuropathy may stem from the diversity of ER stress responses in the different primary afferent classes and cells supporting or communicating with these neurons. Excellent examples of this selectivity and diversity among nociceptors in response to injured adjacent ganglia are reported by several groups (32, 33). In these studies ligation based nerve damage induced pain is associated with selective changes in different types of uninjured C-, Aδ and Aβ nociceptors demonstrating their diverse levels of susceptibility and responses to insult. Overall our observations provide a system wide view of the diabetic PNS where key cellular events, activation of autophagy and apoptosis and key molecular events phosphorylation of p38 and its substrate JNK are simultaneous and driven by ER stress. There is naturally epistemic uncertainty in the two new models of ER stress based pain reported here. However, one remedy for reducing uncertainty is indeed increasing the diversity of the models. Our findings argue that ER stress based models of pain in fact could have more utility than others in evaluating novel compounds. On the other hand many of the currently used models may in fact incorporate a strong ER stress based component as exemplified here with the STZ model.

The epoxy fatty acids are potent and short lived bioactive lipid mediators. Although the discovery of their presence dates back to several decades, initial studies required laborious synthesis and purification steps to obtain sufficient quantities for bioassays which were mostly restricted to in vitro and ex vivo systems (34). Subsequently, the realization that the soluble epoxide hydrolase (sEH) is a major contributor to their short half-life in vivo drove the discovery of inhibitors of sEH with increasing potency and drug like properties over the past decade (35, 36). Current inhibitors, including TPPU, are easy to administer orally or in drinking water, have high rates of exposure and are exceptionally potent on sEH (20). Taking advantage of these selective probes and mass spectroscopy technology to monitor the EpFAs along with a larger panel of other eicosanoids of the ARA cascade, we determined that inhibition of sEH has anti-inflammatory effects (37). Surprisingly, the EpFAs not only block inflammation due to sepsis and pain associated with inflammation but also are independently analgesic, being effective in models of nerve injury and PGE2 induced pain (12). The established kinase mediators of neuropathic pain, p38 and JNK, are effectively blocked by inhibition of sEH as early as 30 min after induction of ER stress. This finding also predicts that inhibition of sEH could lead to efficacious and broad spectrum therapeutics for neuropathic pain. An example of the efficacy of sEHI in non-rodent species was recently published in a horse suffering from terminal laminitis (38). Much of the work performed with the EpFAs and sEHI in our laboratory results in similar outcomes with the exception that sEHI have more profound and sustained activity compared to the EpFAs themselves (13). This is not surprising since sEHI stabilize EpFAs. However, even in the absence of the sEHI the administration of the EpFAs to the site of inflammation or by intraspinal or intracerebroventricular routes also result in direct pain and seizure blocking effects (39). Overall these are very encouraging developments, although bioactive lipids as mediators of analgesia are not well understood. The EpFAs and endocannabionoids certainly do not fit the criteria of neurotransmitters. While the endocannabinoids produce a more recognizable phenotype, the behavioral profile of EpFAs is more subtle and difficult to fit into known classes of compounds. Despite this difficulty in classification, inhibition of sEH have several key advantages in pain therapy, including better efficacy than existing analgesics, lack of narcotic and addictive effects and lack of gastrointestinal and cardiac side effects. There are clear and multiple mechanisms of action of EpFAs and sEHI in reducing pain related behavior. Stronger evidence points towards positive modulation of the GABAergic signaling since sEHI and EpFAs have anticonvulsant effects in models of chemically induced seizures, only when GABA antagonists are used. Furthermore their efficacy is reversible by blockage of the steroid and neurosteroid synthetic pathways at distinct steps. At this point it is unknown if the sEHI augment GABAergic signaling through their ability to block ER stress and render the GABA system functional under neuropathic conditions, which is known to reduce the activity of GABAergic signaling (40). Regardless, investigation of if and how classical pain targets respond to ER stress or its alleviation is an area of future interest.

From a translational point of view development of novel pain therapeutics has been slow compared to other drugs. Remarkably few drug candidates with novel mechanisms of action are currently under development despite significant clinical need for new drugs to treat pain. The discovery that pain is largely regulated by ER stress should raise the hopes of developing a new generation of effective therapeutics in the form of inhibitors of sEH or of other ER stress regulators that potentially address diverse painful state in patients. These compounds in theory may have a lesser degree of mechanistic toxicity if nociceptive neurons are more susceptible to ER stress as argued here.

REFERENCES

1. Kozutsumi Y, Segal M, Normington K, Gething M J, & Sambrook J (1988) The presence of malfolded proteins in the endoplasmic reticulum signals the induction of glucose-regulated proteins. Nature 332:462-464
2. Wang S & Kaufman R J (2012) The impact of the unfolded protein response on human disease. J Cell Biol 197:857-867
3. Doyle K M, et al. (2011) Unfolded proteins and endoplasmic reticulum stress in neurodegenerative disorders. J Cell Mol Med 15:2025-2039
4. Thomas P K & Lascelles R G (1965) Schwann-Cell Abnormalities in Diabetic Neuropathy. Lancet 1:1355-1357
5. Strachan M W J & Price J F (2014) Diabetes: Cognitive decline and T2DM, a disconnect in the evidence? Nat Rev Endocrinol 10:258-260
6. Reske-Nielsen E & Lundbaek K (1968) Pathological changes in the central and peripheral nervous system of young long-term diabetics. Diabetologia 4:34-43
7. Inceoglu B, et al. (2012) Acute augmentation of epoxygenated fatty acid levels rapidly reduces pain-related behavior in a rat model of type I diabetes. P Natl Acad Sci Usa 109:11390-11395
8. Thomas H, Schladt L, Knehr M, & Oesch F (1989) Effect of diabetes and starvation on the activity of rat liver epoxide hydrolases, glutathione S-transferases and peroxisomal beta-oxidation. Biochem Pharmacol 38:4291-4297
9. De Taeye B M, et al. (2010) Expression and regulation of soluble epoxide hydrolase in adipose tissue. Obesity 18:489-498
10. Dewey S, Lai X, Witzmann F A, Sohal M, & Gomes A V (2013) Proteomic analysis of hearts from Akita mice suggests that increases in soluble epoxide hydrolase and antioxidative programming are key changes in early stages of diabetic cardiomyopathy. J Proteome Res 12:3920-3933
11. Inceoglu B, et al. (2006) Inhibition of soluble epoxide hydrolase reduces LPS-induced thermal hyperalgesia and mechanical allodynia in a rat model of inflammatory pain. Life Sci 79:2311-2319
12. Inceoglu B, et al. (2011) Analgesia mediated by soluble epoxide hydrolase inhibitors is dependent on cAMP. P Natl Acad Sci USA 108:5093-5097
13. Inceoglu B, et al. (2013) Epoxy fatty acids and inhibition of the soluble epoxide hydrolase selectively modulate GABA mediated neurotransmission to delay onset of seizures. PLoS One 8(12):e80922.
14. Wagner K, Yang J, Inceoglu B, & Hammock B D (2014) Soluble epoxide hydrolase inhibition is antinociceptive in a mouse model of diabetic neuropathy. J Pain 15:907-914
15. Inceoglu B, et al. (2008) Soluble epoxide hydrolase and epoxyeicosatrienoic acids modulate two distinct analgesic pathways. P Natl Acad Sci USA 105:18901-18906
16. Piomelli D, Hohmann A G, Seybold V, & Hammock B D (2014) A lipid gate for the peripheral control of pain. J Neurosci 34:15184-15191
17. Bettaieb A, et al. (2013) Soluble epoxide hydrolase deficiency or inhibition attenuates diet-induced endoplasmic reticulum stress in liver and adipose tissue. J Biol Chem 288:14189-14199
18. Ji R R, Gereau R Wt, Malcangio M, & Strichartz G R (2009) MAP kinase and pain. Brain Res Rev 60(1):135-148
19. Lupachyk S, Watcho P, Obrosov A A, Stavniichuk R, & Obrosova I G (2013) Endoplasmic reticulum stress contributes to prediabetic peripheral neuropathy. Exp Neurol 247:342-348
20. Rose T E, et al. (2010) 1-Aryl-3-(1-acylpiperidin-4-yl) urea inhibitors of human and murine soluble epoxide hydrolase: structure-activity relationships, pharmacokinetics, and reduction of inflammatory pain. J Med Chem 53:7067-7075
21. Ozcan U, et al. (2006) Chemical chaperones reduce ER stress and restore glucose homeostasis in a mouse model of type 2 diabetes. Science 313:1137-1140
22. Chou T C (2006) Theoretical basis, experimental design, and computerized simulation of synergism and antagonism in drug combination studies. Pharmacol Rev 58:621-681
23. Watowich S S & Morimoto R I (1988) Complex regulation of heat shock- and glucose-responsive genes in human cells. Mol Cell Biol 8:393-405
24. Kardosh A, et al. (2005) Dimethyl-celecoxib, a derivative of celecoxib that lacks cyclooxygenase-2-inhibitory function, potently mimics the anti-tumor effects of celecoxib on Burkitt's lymphoma in vitro and in vivo. Cancer Biol Ther 4:571-582
25. Pyrko P, et al. (2007) Calcium-activated endoplasmic reticulum stress as a major component of tumor cell death induced by 2,5-dimethyl-celecoxib, a non-coxib analogue of celecoxib. Mol Cancer Thera 6:1262-1275
26. Peltier A, Goutman S A, & Callaghan B C (2014) Painful diabetic neuropathy. Bmj 348:g1799.
27. Tesfaye S, Boulton A J, & Dickenson A H (2013) Mechanisms and management of diabetic painful distal symmetrical polyneuropathy. Diab Care 36:2456-2465
28. Ozcan U, et al. (2004) Endoplasmic reticulum stress links obesity, insulin action, and type 2 diabetes. Science 306:457-461
29. Gregor M F, et al. (2009) Endoplasmic reticulum stress is reduced in tissues of obese subjects after weight loss. Diabetes 58:693-700
30. Hetz C, Chevet E, & Harding H P (2013) Targeting the unfolded protein response in disease. Nat Rev Drug Disc 12:703-719
31. Malik R A (2014) Pathology of human diabetic neuropathy. Handb Clin Neurol 126:249-259.
32. Boada M D, et al. (2014) Nerve injury induces a new profile of tactile and mechanical nociceptor input from undamaged peripheral afferents. J Neurophysiol:jn 00506 02014
33. Djouhri L, Fang X, Koutsikou S, & Lawson S N (2012) Partial nerve injury induces electrophysiological changes in conducting (uninjured) nociceptive and nonnociceptive DRG neurons: Possible relationships to aspects of peripheral neuropathic pain and paresthesias. Pain 153:1824-1836
34. Capdevila J, et al. (1981) The oxidative metabolism of arachidonic acid by purified cytochromes P-450. Biochem Biophys Res Comm 101:1357-1363
35. Chacos N, et al. (1983) The reaction of arachidonic acid epoxides (epoxyeicosatrienoic acids) with a cytosolic epoxide hydrolase. Arch Biochem Biophys 223:639-648
36. Morisseau C, et al. (1999) Potent urea and carbamate inhibitors of soluble epoxide hydrolases. P Natl Acad Sci USA 96:8849-8854
37. Schmelzer K R, et al. (2005) Soluble epoxide hydrolase is a therapeutic target for acute inflammation. P Natl Acad Sci USA 102:9772-9777
38. Guedes A G, et al. (2013) Use of a soluble epoxide hydrolase inhibitor as an adjunctive analgesic in a horse with laminitis. Vet Anaesth Analg 40:440-448
39. Morisseau C, et al. (2010) Naturally occurring monoepoxides of eicosapentaenoic acid and docosahexaenoic acid are bioactive antihyperalgesic lipids. J Lipid Res 51:3481-3490
40. Enna S J & McCarson K E (2006) The role of GABA in the mediation and perception of pain. Adv Pharmacol 54:1-27

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing, ameliorating, mitigating, inhibiting and/or reversing pain in a subject in need thereof, comprising co-administering to the subject an agent that increases the production and/or level of epoxygenated fatty acids and an inhibitor of endoplasmic reticulum stress, wherein
the agent that increases the production and/or level of epoxygenated fatty acids is 1-trifluoromethoxyphenyl-3-(1-propionylpiperidin-4-yl) urea (TPPU); and
the inhibitor of endoplasmic reticulum stress is 4-phenyl butyric acid ("PBA").

2. The method of claim 1, wherein the pain comprises inflammatory pain.

3. The method of claim 1, wherein the pain comprises neuropathic pain.

4. The method of claim 3, wherein the neuropathic pain comprises nerve damage induced pain.

5. The method of claim 3, wherein the neuropathic pain is central neuropathic pain.

6. The method of claim 3, wherein the neuropathic pain is peripheral neuropathic pain.

7. The method of claim 1, wherein the reducing, ameliorating, mitigating, inhibiting and/or reversing of the pain is experienced by the subject within 24 hours.

8. The method of claim 1, wherein one or both of the agent that increases the production and/or level of epoxygenated fatty acids and the inhibitor of endoplasmic reticulum stress are administered at a subtherapeutic dose, the subtherapeutic dose being about 75% or less than the amount of the agent that increases the production and/or level of epoxygenated fatty acids and the inhibitor of endoplasmic reticulum stress conventionally administered.

9. The method of claim 1, wherein the agent that increases the production and/or level of epoxygenated fatty acids and the inhibitor of endoplasmic reticulum stress are concurrently or sequentially co-administered.

10. The method of claim 1, wherein the TPPU is co-administered at a subtherapeutic dose, the subtherapeutic dose being about 75% or less than the amount of the TPPU conventionally administered.

11. The method of claim 1, wherein the subject is a human.

\* \* \* \* \*